US005968782A

United States Patent [19]
Stevens

[11] Patent Number: 5,968,782
[45] Date of Patent: Oct. 19, 1999

[54] MAST CELL PROTEASE THAT CLEAVES FIBRINOGEN

[75] Inventor: Richard L. Stevens, Sudbury, Mass.

[73] Assignee: Brigham and Womens's Hospital, Inc., Boston, Mass.

[21] Appl. No.: 08/978,404

[22] Filed: Nov. 25, 1997

Related U.S. Application Data

[60] Provisional application No. 60/032,354, Dec. 4, 1996.
[51] Int. Cl.$^6$ .............................. C12N 15/62; C12N 9/64; C12N 15/67; C12N 15/85
[52] U.S. Cl. ..................... 435/69.7; 435/226; 435/252.3; 435/320.1; 530/413; 536/23.4
[58] Field of Search .................................. 435/69.7, 226, 435/252.3, 320.1; 530/413; 536/23.4

[56] References Cited

U.S. PATENT DOCUMENTS

| | | | |
|---|---|---|---|
| 5,087,564 | 2/1992 | Mai et al. | 435/69.7 |
| 5,187,157 | 2/1993 | Kettner et al. | 514/18 |
| 5,202,239 | 4/1993 | Tarnowski et al. | 435/69 |
| 5,239,058 | 8/1993 | Vlasuk et al. | 530/524 |
| 5,372,812 | 12/1994 | Reed et al. | 424/145.1 |
| 5,385,732 | 1/1995 | Anderson et al. | 424/94.64 |
| 5,405,771 | 4/1995 | Anderson et al. | 435/240 |
| 5,525,623 | 6/1996 | Spear et al. | 514/423 |
| 5,538,863 | 7/1996 | Price | 435/536 |
| 5,541,087 | 7/1996 | Lo et al. | 435/697 |
| 5,567,602 | 10/1996 | Clark et al. | 435/226 |

FOREIGN PATENT DOCUMENTS

| | | |
|---|---|---|
| WO 91/02972 | 3/1991 | WIPO . |
| WO94/16083 | 7/1994 | WIPO . |
| WO94/20527 | 9/1994 | WIPO . |
| WO95/21861 | 8/1995 | WIPO . |
| WO96/09297 | 3/1996 | WIPO . |
| WO98/24886 | 6/1998 | WIPO . |

OTHER PUBLICATIONS

Wang, Z.–M., et al., Biological Chemistry Hoppe–Seyler, vol. 376, "Production of active recombinant human chymase from a construct containing the enterokinase cleavage site of trypsinogen in place of the native propeptide sequence", pp. 681–684, 1995.

Ghildyal, N., et al., "Fate of Two Mast Cell Tryptases . . . ", *J. Exp. Med.*, (1996), 184:1061–1073.

Matsumoto, R., et al., "Packaging of Proteases . . . ".*J. Biol. Chem.*, (1995), 270:33:19524–19531.

Braganza, V., et al., "Tryptase from Rat Skin: . . . ", *Biochemistry*, (1991), 30:4997–5007.

Schwartz, L., "Tryptase, a mediator of . . . ", *J Allergy Clin Immunol*, (1990), 86:4 Pt2:594–598, Abstract.

Alter, S., et al., "Interactions of human mast cell . . . ",*Arch Biochem Biophys*, (1990), 276:1:26–31, Abstract.

Harvima, I., et al., "Effect of human mast . . . ", *Int Arch Allergy Appl Immunol*, (1989), 90:1:104–108, Abstract.

Katumuma, N., et al., "Biological functions . . . ", *J Cell Biochem*, (1988), 38:4:291–301 Abstract.

Schwartz, L., et al., "The fibrinogenolytic activity . . . ", *J Immunol*, (1985), 135:4:2762–2767 Abstract.

Seppa, H., et al., "The role of chrymotrypsin–like . . . ", *Inflammation*, (1980), 4:1:1–8 Abstract.

Pastan, I., et al., "Purification and properties . . . ", *J Biol Chem*, (1996), 241:21:5090–5094 Abstract.

Schwartz, L., et al., "Effect of Tryptase . . . ", *J Allergy Clin Immunol*, (1985), 75 (1 Part 2) Abstract.

Forsberg, G., et al., "An evaluation of . . . ",*J Protein Chem*, (1992), 11:2:201–211 Abstract.

Light, A., et al., "The amino–terminal . . . ",*J. Protien Chem*, (1991), 10:5:475–480 Abstract.

Martinez, A., et al., "Expression of recombinant . . . ", *Biochem J.*, (1995), 306(Pt 2): 589–597 Abstract.

Su, X., et al., "Production of recombinant . . . ", *Biotechniques*, (1992), 12:5:756–762 Abstract.

Kuhn, S., et al., "The baculovirus expression . . . ", *Gene*, (1995), 162:2:225–229 Abstract.

Kroll, D., et al., "A multifunctional prokaryotic . . . ", *DNA Cell Biol*, 12:5:441–453 Abstract 1993.

Dobrynin, V., et al., "Chemical–enzymatic . . . ", *Bioorg Khim*, (1989), 15:9:1232–1238 Abstract.

Scheele, G., et al., "Proteolytic processing . . . ", *J Biol Chem*, 258:3:2005–2009 Abstract.

Bajusz, S., Peptide Inhibitors of Trypsin–Like Enzymes, Symposia Biologica Hungarica 25; pp. 279–298, (1984).

Jouko Lohi et al., Pericellular Substrates of Human Mast Cell Tryptase: 72,000 Dalton Gelatinase and Fibronectin, Journal of Cellular Biochem., 50;337–349 (1992).

Beat Steiner et al., Peptides Derived from a Sequence within $\beta_3$ Integrin Bind to Platelet $\alpha_{IIb}\beta\_$ (GPIIIb–IIIa) and Inhibit Ligand Binding, J. of Biological Chem. 268, No. 10, Apr. 5, 1993, pp. 6870–6873.

Rami Herskoviz et al., Nonpeptidic Analogues of the Arg–Gly–Asp (RGD) Sequence Specifically Inhibit the Adhesion of Human Tenon's Capsule Fibroblasts to Fibronectin, Investigative Opthalmology & Visual Science, vol. 35, No. 5, Apr. 1994, pp. 2585–2591.

Clark, J., et al., Tryptase Inhibitors Block Allergen–induced Airway and Inflammatory Responses in Allergic Sheep, Am J Respir Crit Care Med (1995) 152;2076–2083.

McNeil et al., Isolation, characterization, and transcription of the gene encoding mouse mast cell protease protease 7,Proc. Natl. Acad. Sci. USA 89:11174–11178, 1992.

(List continued on next page.)

*Primary Examiner*—Robert A. Wax
*Assistant Examiner*—William W. Moore
*Attorney, Agent, or Firm*—Wolf, Greenfield & Sacks, P.C.

[57] ABSTRACT

Compositions containing a Trypson-like serine protease from mast cells ("tryptase-7") are provided. The compositions are useful for treating blood clot formation in vitro and in in vitro. Also provided is a novel bioengineering method to produce the tryptase-7 and other serine proteases in active form and in large quantities.

11 Claims, No Drawings

OTHER PUBLICATIONS

Gruber, B., et al., "The Mast Cell as an Effector of Connective Tissue Degradation: A Study of Matrix Susceptibility to Human Mast Cells", *Biochem & Biophys Res Com,* (1990), 171;3;1272–1278.

Cairns, J., et al., "Mast Cell Tryptase Is a Mitogen for Epithelial Cells", *J Immun,* (1996), 156;275–283.

Kielty, C., et al., "Catabolism of Intact Type VI Collagen Microfibrils: Susceptibility To Degradation By Serine Proteinases", *Biochem & Biophys Res Com.* (1993), 191;3;1230–1236.

Kovanen, P., et al., "Infiltrates of Activated Mast Cells at the Site of Coronary Atheromatous Erosion or Rupture in Myocardial Infarction", *Circulation,* (1995), 92;5;1084–1088.

Saarinen, J., et al., "Activation of Human Interstitial Procollagenase through Direct Cleavage of the $Leu^{83}$–$Thr^{84}$ Bond by Mast Cell Chymase", *J Bio Chem,* (1994), 269;27;18134–18140.

DuBuske, L., et al., "Granule–Associated Serine Neutral Proteases of the Mouse Bone Marrow–Derived Mast Cell That Degrade Fibronectin: Their Increase After Sodium Butyrate Treatment of the Cells", *J Immun. ,* (1984), 133;3;1535–1541.

Constantinides, P., et al., Infiltrates of Activated Mast Cellsa t the site of Coronary Atheromatous Erosion or Rupture in Myocardial Infarction, Circulation (1995) 92;1083.

SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
      (A) LENGTH: 1031 base pairs
      (B) TYPE: nucleic acid
      (C) STRANDEDNESS: single
      (D) TOPOLOGY: linear (xi) SEQUENCE DESCRIPTION: SEQ ID NO:1:

```
CCCGCACTAC TCCTCACTGT GTCCAAATGC TAAAGCTGCT GCTGCTCACG CTGCCCCTCC      60

TGTCCAGCCT GGTGCATGCA GCCCCCGGTC CAGCTATGAC ACGAGAAGGC ATTGTGGGGG     120

GACAGGAGGC ACATGGGAAC AAGTGGCCCT GGCAGGTGAG CCTGCGTGCC AATGACACCT     180

ACTGGATGCA TTTCTGCGGT GGCTCCCTCA TCCACCCACA GTGGGTGCTC ACTGCGGCAC     240

ACTGTGTGGG ACCGGATGTT GCTGACCCCA ACAAGGTCAG AGTACAGCTC CGTAAGCAGT     300

ACCTCTATTA CCATGACCAC CTGATGACTG TGAGCCAGAT CATCACACAC CCCGACTTCT     360

ACATCGTCCA GGATGGGGCA GACATTGCCC TGCTGAAACT CACAAACCCT GTGAACATTT     420
```

```
CTGACTATGT CCACCCTGTC CCCCTACCTC CTGCCTCAGA GACCTTCCCC TCAGGAACGT      480

TGTGCTGGGT GACAGGCTGG GGTAACATCG ACAATGGTGT AAACCTGCCG CCACCATTTC      540

CTTTGAAGGA GGTGCAAGTT CCCATTATAG AAAACCACCT TTGTGACTTG AAGTATCACA      600

AAGGTCTCAT CACAGGTGAC AATGTCCACA TTGTCCGAGA TGACATGCTG TGTGCTGGGA      660

ATGAAGGACA TGACTCCTGC CAGGGCGACT CCGGAGGACC TCTGGTCTGC AAGGTAGAAG      720

ACACCTGGCT GCAGGCAGGC GTGGTCAGCT GGGGTGAGGG CTGTGCACAG CCCAACAGGC      780

CTGGCATCTA CACCCGGGTC ACCTATTACT TGGACTGGAT CCACCACTAT GTCCCCAAGG      840

ACTTCTGAGT CACATCCAGG ATGACCTCCG TTCCTCCCAG CATGCTGCTT CCTGCCCGGG      900

TGGCATCCCT GCCTTCCTCT CCTGCTCCCC ATCCTGAGTC CCAATTCTTC TGCCTTCCAC      960

TCAAGTAGCT ACACTGAGCA GGCGCCGCTC TCTGCTATGC CTCAATAAAA TGCGTTAAAG     1020

CAAAAAAAAA A                                                          1031
```

(2) INFORMATION FOR SEQ ID NO:2:

(i) SEQUENCE CHARACTERISTICS:
        (A) LENGTH: 2397 base pairs
        (B) TYPE: nucleic acid
        (C) STRANDEDNESS: single
        (D) TOPOLOGY: linear (xi) SEQUENCE DESCRIPTION: SEQ ID NO:2:

```
TGGATTGGAG GGTGTCATGC CCTTCCTCCC ACCCCACCCT GTTCTGGGAG GATAAGTGGA       60

GAGGGAACTT GAGACTGGGT AGAGAAGATT GAAGACTGCT AAAGTGATCT CTCCTGGACC      120

CTGAAGCAGA GTGGCCAAGC CATTAGAGAC CTCGGGCTGT TGGAATGAAC CTACCTTCCT      180

GCTCCCAGGT TCCTGGCTTG TGCGCCCCAC AACCTGTTGG GCCTAGACTA GCCCTCACCT      240

CCAACTGGGC CCGCACTACT CCTCACTGTG TCCAAATGCT AAAGCTGCTG CTGCTCACGC      300

TGCCCCTCCT GTCCAGCCTG GTGCATGCAG CCCCCGGTGA GTTCTCCCCT GGGCCCTCCC      360

TGTCCCTCTT CCTGACCCTC TTAGCTCGCA GGCCAAGGTA TTAAAATTAG TCCTGTCCTA      420

TCCCCAGGTC CAGCTATGAC ACGAGAAGGC ATTGTGGGGG ACAGGAGGC ACATGGGAAC       480

AAGTGGCCCT GGCAGGTGAG CCTGCGTGCC AATGACACCT ACTGGATGCA TTTCTGCGGT      540

GGCTCCCTCA TCCACCCACA GTGGGTGCTC ACTGCGGCAC ACTGTGTGGG ACCGTGAGTC      600

TACCTGGGCT TGGCAGAGTG GGACAAGGAA TGGGTAGGAG AGTGGGGTAA GATGGGATCA      660

TCACACACCA TCTCTGGGTT TCTGGAAGTG ACACAGGCCT CCTAAATGAA TATCTCTTCT      720

CTTTAGGGAT GTTGCTGACC CCAACAAGGT CAGAGTACAG CTCCGTAAGC AGTACCTCTA      780

TTACCATGAC CACCTGATGA CTGTGAGCCA GATCATCACA CACCCCGACT TCTACATCGT      840

CCAGGATGGG GCAGACATTG CCCTGCTGAA ACTCACAAAC CCTGTGAACA TTTCTGACTA      900

TGTCCACCCT GTCCCCCTAC CTCCTGCCTC AGAGACCTTC CCCTCAGGAA CGTTGTGCTG      960

GGTGACAGGC TGGGGTAACA TCGACAATGG TGGTATGTAG TAGAGACAAC TGAGGTTAGA     1020

CAGGTGAGGG AGCGGCCACG CCCATCCACA GCACAGGGCT TCCCTCCAAC TTTGTAGGAT     1080

GGAAAGCTGA AGACCTCGGA AGTGGAAAGG CATCAGGACA TCAGGGATTT CAGGGTCCAT     1140

AAGCCAGGAT ACCCCAGGGT AGCTACCATA AGTCATTCGA CCCCTCTAAT CTCAGACACT     1200

TCATGTCTGA AGGGACCACA GTATGCTTGT ATTTCGGAGA TTTGATTGAG AAAGAGTCCG     1260

ATCACACTTA CCAACAATGT CTCCAGCAGC ACTTCATGGG CTGTGGTATT GTGTAGGGCT     1320

AGATTGCTCC CTTGGGAGCC TCCAGCACCA GTTTGCCTTC TCCCTAGTGG TCTTACTTCA     1380

TTTCTTTTGA CAACTCAGAG TAGAGCTTTA GGGATAGGGC CATGAGCAGG CAGACCCTGG     1440
```

```
CTGCAGACCA CAGGAAGGAT CCAGTCTCTC TGTACACAGA GGTGGGGCAG GAGAATAGTG  1500

TCCAACCAGG GCTCCACTGG AATCCTCTAT CCAGCCTAGG CCAGAGCCAG CGGTGCTGAG  1560

GGAGATAACT ACCTCTGCCC CTGCCCGTCA CTGACCAGAT GGCCCACTAA AGACCCTCTG  1620

GGCTGTCCTC CTTCTCTGAA TAAGGTCGGA AATCCAGGTC CAGCCTGGAG GAAAAAGCCA  1680

GGTTGGCAGA GCTGAATGCC ATGGGCCGGA CTCAAAGAGG GACTTGTGAG CAGAACTATC  1740

CTCAGAGAAC GGGGTTAGCT GAGCCCATCC CAGCTTGCCA ACCTGAGACT CTGCCCACAA  1800

AATGGTCTTT CTTTCACCTA CAGTAAACCT GCCGCCACCA TTTCCTTTGA AGGAGGTGCA  1860

AGTTCCCATT ATAGAAAACC ACCTTTGTGA CTTGAAGTAT CACAAAGGTC TCATCACAGG  1920

TGACAATGTC CACATTGTCC GAGATGACAT GCTGTGTGCT GGGAATGAAG GACATGACTC  1980

CTGCCAGGTG AACTCCTGTC CCCTCACCCT GCCACCCCTA CCCAGCCTTT ACAGGAGTAC  2040

TGACCCCTAT CCTCTCTAGG GCGACTCCGG AGGACCTCTG GTCTGCAAGG TAGAAGACAC  2100

CTGGCTGCAG GCAGGCGTGG TCAGCTGGGG TGAGGGCTGT GCACAGCCCA ACAGGCCTGG  2160

CATCTACACC CGGGTCACCT ATTACTGGA CTGGATCCAC CACTATGTCC CCAAGGACTT  2220

CTGAGTCACA TCCAGGATGA CCTCCGTTCC TCCCAGCATG CTGCTTCCTG CCCGGGTGGC  2280

ATCCCTGCCT TCCTCTCCTG CTCCCCATCC TGAGTCCCAA TTCTTCTGCC TTCCACTCAA  2340

GTAGCTACAC TGAGCAGGCG CCGCTCTCTG CTATGCCTCA ATAAAATGCG TTAAAGC     2397
```

(2) INFORMATION FOR SEQ ID NO:3:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

```
Met Leu Lys Leu Leu Leu Leu Thr Leu Pro Leu Ser Ser Leu Val
 1               5                  10                  15

His Ala Ala Pro Gly Pro Ala Met Thr Arg Glu Gly Ile Val Gly Gly
            20                  25                  30

Gln Glu Ala His Gly Asn Lys Trp Pro Trp Gln Val Ser Leu Arg Ala
        35                  40                  45

Asn Asp Thr Tyr Trp Met His Phe Cys Gly Gly Ser Leu Ile His Pro
    50                  55                  60

Gln Trp Val Leu Thr Ala Ala His Cys Val Gly Pro Asp Val Ala Asp
65                  70                  75                  80

Pro Asn Lys Val Arg Val Gln Leu Arg Lys Gln Tyr Leu Tyr Tyr His
                85                  90                  95

Asp His Leu Met Thr Val Ser Gln Ile Ile Thr His Pro Asp Phe Tyr
            100                 105                 110

Ile Val Gln Asp Gly Ala Asp Ile Ala Leu Leu Lys Leu Thr Asn Pro
        115                 120                 125

Val Asn Ile Ser Asp Tyr Val His Pro Val Pro Leu Pro Pro Ala Ser
    130                 135                 140

Glu Thr Phe Pro Ser Gly Thr Leu Cys Trp Val Thr Gly Trp Gly Asn
145                 150                 155                 160

Ile Asp Asn Gly Val Asn Leu Pro Pro Phe Pro Leu Lys Glu Val
                165                 170                 175
```

```
Gln Val Pro Ile Ile Glu Asn His Leu Cys Asp Leu Lys Tyr His Lys
            180                 185                 190

Gly Leu Ile Thr Gly Asp Asn Val His Ile Val Arg Asp Asp Met Leu
        195                 200                 205

Cys Ala Gly Asn Glu Gly His Asp Ser Cys Gln Gly Asp Ser Gly Gly
    210                 215                 220

Pro Leu Val Cys Lys Val Glu Asp Thr Trp Leu Gln Ala Gly Val Val
225                 230                 235                 240

Ser Trp Gly Glu Gly Cys Ala Gln Pro Asn Arg Pro Gly Ile Tyr Thr
                245                 250                 255

Arg Val Thr Tyr Tyr Leu Asp Trp Ile His His Tyr Val Pro Lys Asp
            260                 265                 270

Phe
```

(2) INFORMATION FOR SEQ ID NO:4:

(i) SEQUENCE CHARACTERISTICS:
        (A) LENGTH: 1097 base pairs
        (B) TYPE: nucleic acid
        (C) STRANDEDNESS: single
        (D) TOPOLOGY: linear (xi) SEQUENCE DESCRIPTION: SEQ ID NO:4:

```
GGAGAGAGGA GCCGAGACAG CCAAGATGCT GAAGCTGCTG CTGCTGCTGG CACTGTCCCC    60

CCTGGCTAGT CTGGTGCACG CGGCCCCTTG CCCAGTCAAG CAGCGAGTGG GCATTGTGGG   120

AGGACGAGAG GCTTCTGAAA GTAAGTGGCC CTGGCAGGTG AGCCTGAGAT TTAAATTCAG   180

CTTCTGGATG CATTTCTGTG GCGGCTCCCT CATTCACCCA CAGTGGGTGC TCACTGCGGC   240

ACACTGTGTG GGACTGCACA TCAAAAGCCC AGAGCTCTTC CGTGTACAGC TTCGTGAGCA   300

GTATCTATAC TATGCGGACC AGCTACTGAC TGTGAACGG ACCGTTGTGC ACCCCCACTA    360

CTACACAGTC GAGGATGGGG CAGACATTGC CCTGCTGGAG CTTGAGATCC CTGTGAATGT   420

CTCCACCCAT ATCCACCCCA TATCCCTGCC CCCTGCCTCG GAGACCTTCC CCTCGGGGAC   480

TTCTTGCTGG GTAACAGGCT GGGGCGACAT TGATAGTGAC GAGCCTCTCC TGCCACCTTA   540

TCCTCTGAAG CAAGTGAAGG TCCCCATTGT GGAAAACAGC CTGTGTGATC GGAAGTACCA   600

CACTGGCCTC TACACAGGAG ATGATGTTCC CATTGTCCAG GATGGCATGC TGTGTGCTGG   660

AAATACCAGG AGCGACTCCT GCCAGGGAGA CTCAGGGGGC CCACTGGTCT GCAAAGTGAA   720

GGGTACCTGG CTGCAAGCAG GAGTGGTCAG CTGGGGTGAG GGCTGCGCAG AGGCCAATCG   780

TCCTGGCATT TACACCCGGG TGACGTACTA CCTGGACTGG ATTCACCGCT ATGTCCCTCA   840

GCGTTCCTGA GACCCATCCA GGGTCAGGGA AGAACCAGGC ACCTGCTGTC TTTAACTCAC   900

TGCTTCCTGG CCAGATGGAA CCCTGGCCTT CTTTGTACTC TGTCTCCCCT GTCTACCGGG   960

TGTCCCTCTG AGCCCCCACT TTGTTCCACC TTGAGTCCCT CGCCACTCCT GTCCCCTCTG  1020

CCTCCCACCA CAACACAGCT GCACTGTGCG GCTCCCTCTT TTCTGTGGCT CATTAAAGTA  1080

TGTGAAAATT TTGCTCC                                                 1097
```

(2) INFORMATION FOR SEQ ID NO:5:

(i) SEQUENCE CHARACTERISTICS:
        (A) LENGTH: 274 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

Met Leu Lys Leu Leu Leu Leu Ala Leu Ser Pro Leu Ala Ser Leu
1               5                   10                  15

Val His Ala Ala Pro Cys Pro Val Lys Gln Arg Val Gly Ile Val Gly
        20                  25                  30

Gly Arg Glu Ala Ser Glu Ser Lys Trp Pro Trp Gln Val Ser Leu Arg
        35                  40                  45

Phe Lys Phe Ser Phe Trp Met His Phe Cys Gly Gly Ser Leu Ile His
        50                  55                  60

Pro Gln Trp Val Leu Thr Ala Ala His Cys Val Gly Leu His Ile Lys
65                  70                  75                  80

Ser Pro Glu Leu Phe Arg Val Gln Leu Arg Glu Gln Tyr Leu Tyr Tyr
                85                  90                  95

Ala Asp Gln Leu Leu Thr Val Asn Arg Thr Val Val His Pro His Tyr
                100                 105                 110

Tyr Thr Val Glu Asp Gly Ala Asp Ile Ala Leu Leu Glu Leu Glu Ile
                115                 120                 125

Pro Val Asn Val Ser Thr His Ile His Pro Ile Ser Leu Pro Pro Ala
        130                 135                 140

Ser Glu Thr Phe Pro Ser Gly Thr Ser Cys Trp Val Thr Gly Trp Gly
145                 150                 155                 160

Asp Ile Asp Ser Asp Glu Pro Leu Leu Pro Pro Tyr Pro Leu Lys Gln
                165                 170                 175

Val Lys Val Pro Ile Val Glu Asn Ser Leu Cys Asp Arg Lys Tyr His
                180                 185                 190

Thr Gly Leu Tyr Thr Gly Asp Asp Val Pro Ile Val Gln Asp Gly Met
                195                 200                 205

Leu Cys Ala Gly Asn Thr Arg Ser Asp Ser Cys Gln Gly Asp Ser Gly
210                 215                 220

Gly Pro Leu Val Cys Lys Val Lys Gly Thr Trp Leu Gln Ala Gly Val
225                 230                 235                 240

Val Ser Trp Gly Glu Gly Cys Ala Glu Ala Asn Arg Pro Gly Ile Tyr
                245                 250                 255

Thr Arg Val Thr Tyr Tyr Leu Asp Trp Ile His Arg Tyr Val Pro Gln
                260                 265                 270

Arg Ser (2) INFORMATION FOR SEQ ID NO:6:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

Met Leu Lys Leu Leu Leu Thr Leu Pro Leu Leu Ser Ser Leu Val
1               5                   10                  15

His Ala Ala Pro Ser Leu Ala Met Pro Arg Glu Gly Ile Val Gly Gly
        20                  25                  30

Gln Glu Ala Ser Gly Asn Lys Trp Pro Trp Gln Val Ser Leu Arg Val
        35                  40                  45

Asn Asp Thr Tyr Trp Met His Phe Cys Gly Gly Ser Leu Ile His Pro
        50                  55                  60

-continued

```
Gln Trp Val Leu Thr Ala Ala His Cys Val Gly Pro Asn Lys Ala Asp
 65                  70                  75                  80

Pro Asn Lys Leu Arg Val Gln Leu Arg Lys Gln Tyr Leu Tyr Tyr His
                 85                  90                  95

Asp His Leu Leu Thr Val Ser Gln Ile Ile Ser His Pro Asp Phe Tyr
            100                 105                 110

Ile Ala Gln Asp Gly Ala Asp Ile Ala Leu Leu Lys Leu Thr Asn Pro
        115                 120                 125

Val Asn Ile Thr Ser Asn Val His Thr Val Ser Leu Pro Pro Ala Ser
130                 135                 140

Glu Thr Phe Pro Ser Gly Thr Leu Cys Trp Val Thr Gly Trp Gly Asn
145                 150                 155                 160

Ile Asn Asn Asp Val Ser Leu Pro Pro Phe Pro Leu Glu Glu Val
                165                 170                 175

Gln Val Pro Ile Val Glu Asn Arg Leu Cys Asp Leu Lys Tyr His Lys
            180                 185                 190

Gly Leu Asn Thr Gly Asp Asn Val His Ile Val Arg Asp Asp Met Leu
        195                 200                 205

Cys Ala Gly Asn Glu Gly His Asp Ser Cys Gln Gly Asp Ser Gly Gly
    210                 215                 220

Pro Leu Val Cys Lys Val Glu Asp Thr Trp Leu Gln Ala Gly Val Val
225                 230                 235                 240

Ser Trp Gly Glu Gly Cys Ala Gln Pro Asn Arg Pro Gly Ile Tyr Thr
                245                 250                 255

Arg Val Thr Tyr Tyr Leu Asp Trp Ile Tyr Arg Tyr Val Pro Lys Tyr
            260                 265                 270

Phe
```

(2) INFORMATION FOR SEQ ID NO:7:

(i) SEQUENCE CHARACTERISTICS:
        (A) LENGTH: 1219 base pairs
        (B) TYPE: nucleic acid
        (C) STRANDEDNESS: single
        (D) TOPOLOGY: linear (xi) SEQUENCE DESCRIPTION: SEQ ID NO:7:

```
GAGCAGGTTC AAAGACAACC AAGGTGGCCC CCCTCCCAGA GCCTCTGACG TCTGCATGCT    60

GGCCAAGCTG ACTCGAACTC CCGCAATTGG ACCTACCTTC CTGCTCCCTG GTTCCTGGCC   120

TGTTCTGCAC CCGACAATCT GTTGACCCTA GCCAGCCTT TACCTCCAAC TAGGCTCACA    180

CTACTCACTG TTTCCAAATG CTGAAGCTGC TGCTGCTGGC ACTGCCCCTG TTCAGCCTGA   240

TGCATCGGTC CCCGCTGTGC CAAGAGTGGG GCATTGTTGG GGGACAGGAG GCACCTGGGA   300

ACAAGTGGCC CTGGCAGGTG AGCCTTCGTG CCAATGAAAC CTACTGGAGG CATTTCTGCG   360

GCGGCTCCCT CATCCACCCA CAGTGGGTGC TCACCGCGGC ACACTGTGTG GACCGACTA    420

TTGCTGATCC CAACAAGGTC AGAGTACAGC TTCGAAAGCA GTACCTCTAT TACCACGACC   480

ACCTGCTGGC TGTGAGCCGG ATCATCACAC ACCCGACATT CTATGCCACC CAGAATGGGG   540

CGGACATCGC CCTACTTGAG CTCAAGAACC CTGTAAACAT TTCCAGCCAT GTCCACCCCG   600

TCTCCCTGCC TCCTGCCTCA GAGACCTTCC CCTCAGGAAC ATTGTGCTGG GTGACAGGCT   660

GGGGAAACAT CGACAATGAT GTGAGCCTGC CACCGCCATT TCCCTTGAAG GAGGTGCAAG   720

TTCCCGTCGT GGAAAACCAG CTTTGTGACC TGAAGTATCA CAAAGGTGTC TACACAGGGG   780

ACAACATCCA CATTGTCCGA GACGACATGC TGTGTGCTGG GAACGAAGGA CACGACTCCT   840
```

```
GCCAGGGTGA CTCCGGAGGA CCTCTGGTCT GCAAGGTAAA CGGTACCTGG CTGCAGGCAG      900

GTGTGGTCAG CTGGGGTGAG GGCTGTGCTC TGCCCAACAG GCCTGGCATC TACACTCGGG      960

TCACCTATTA CTTGGACTGG ATCCACCGCT ATGTCCCCAA GGACTTCTGA ATCACCTCCA     1020

GAGTCAAGGG AGAACCAGAT CTCTGCTGTC CCCTACACGC TGCTTCCTGC CAGGGCGGAT     1080

CCTTGCTTGC TCTCCTACCA CCTCCCCATC CCTGTGGTGC TCCTCCTGAG CCCCTGGCCA     1140

CTCCTGTCCC TTCCCCTCCA GGCAGCCCCA CTATGTAGCC AGCCATCCTT TGCTATGGCT     1200

CATTAAAATG CACGAAAGC                                                  1219
```

(2) INFORMATION FOR SEQ ID NO:8:

(i) SEQUENCE CHARACTERISTICS:
        (A) LENGTH: 270 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Met Leu Lys Leu Leu Leu Ala Leu Pro Leu Phe Ser Leu Met His
 1               5                  10                  15

Arg Ser Pro Leu Cys Gln Glu Trp Gly Ile Val Gly Gly Gln Glu Ala
            20                  25                  30

Pro Gly Asn Lys Trp Pro Trp Gln Val Ser Leu Arg Ala Asn Glu Thr
        35                  40                  45

Tyr Trp Arg His Phe Cys Gly Ser Leu Ile His Pro Gln Trp Val
    50                  55                  60

Leu Thr Ala Ala His Cys Val Gly Pro Thr Ile Ala Asp Pro Asn Lys
65                  70                  75                  80

Val Arg Val Gln Leu Arg Lys Gln Tyr Leu Tyr Tyr His Asp His Leu
                85                  90                  95

Leu Ala Val Ser Arg Ile Ile Thr His Pro Thr Phe Tyr Ala Thr Gln
            100                 105                 110

Asn Gly Ala Asp Ile Ala Leu Leu Glu Leu Lys Asn Pro Val Asn Ile
        115                 120                 125

Ser Ser His Val His Pro Val Ser Leu Pro Pro Ala Ser Glu Thr Phe
    130                 135                 140

Pro Ser Gly Thr Leu Cys Trp Val Thr Gly Trp Gly Asn Ile Asp Asn
145                 150                 155                 160

Asp Val Ser Leu Pro Pro Pro Phe Pro Leu Lys Glu Val Gln Val Pro
                165                 170                 175

Val Val Glu Asn Gln Leu Cys Asp Leu Lys Tyr His Lys Gly Val Tyr
            180                 185                 190

Thr Gly Asp Asn Ile His Ile Val Arg Asp Asp Met Leu Cys Ala Gly
        195                 200                 205

Asn Glu Gly His Asp Ser Cys Gln Gly Asp Ser Gly Gly Pro Leu Val
    210                 215                 220

Cys Lys Val Asn Gly Thr Trp Leu Gln Ala Gly Val Val Ser Trp Gly
225                 230                 235                 240

Glu Gly Cys Ala Leu Pro Asn Arg Pro Gly Ile Tyr Thr Arg Val Thr
                245                 250                 255

Tyr Tyr Leu Asp Trp Ile His Arg Tyr Val Pro Lys Asp Phe
            260                 265                 270
```

(2) INFORMATION FOR SEQ ID NO:9:

(i) SEQUENCE CHARACTERISTICS:
    (A) LENGTH: 1095 base pairs
    (B) TYPE: nucleic acid
    (C) STRANDEDNESS: single
    (D) TOPOLOGY: linear (xi) SEQUENCE DESCRIPTION: SEQ ID NO:9:

| | | | | | |
|---|---|---|---|---|---|
| GAATTCCAGC | TTGGACTTAA | CCAGGCTGAA | CTTGCTCAAA | AGGTGGGGAC TACCCAGCAG | 60 |
| TCTATAGAGC | AGCTCGAAAA | CGGTAAAACT | AAGCGACCAC | GCTTTTTACC AGAACTTGCG | 120 |
| TCACGTCTTG | GCGTAAGTGT | TGACTGGCTG | CTCAATGGCA | CCTCTGATTC GAATGTTAGA | 180 |
| TTTGTTGGGC | ACGTTGAGCC | CAAAGGTGGG | CATCGTGGGG | GGCTGCAAGG TGCCAGCCAG | 240 |
| GAGGTACCCG | TGGCAGGTCA | GCCTGAGGTT | CCATGGCATG | GGTAGCGGCC AGTGGCAGCA | 300 |
| CATCTGCGGA | GGCTCCCTCA | TCCACCCCCA | GTGGGTGCTG | ACCGCGGCCC ACTGCGTGGA | 360 |
| GCTGGAGGGC | TTGGAGGCTG | CTACCCTCAG | GGTCCAAGTC | GGGCAGCTGA GACTCTACGA | 420 |
| CCACGACCAG | CTGTGCAACG | TGACCGAGAT | CATCCGCCAC | CCCAACTTCA ACATGAGCTG | 480 |
| GTATGGCTGG | ACACGGCGG | ACATCGCCCT | GCTGAAGCTG | GAGGCCCCCC TGACGCTCTC | 540 |
| CGAGGACGTC | AACCTGGTGT | CCCTCCCGTC | TCCCTCCCTG | ATTGTCCCCC CGGGGATGCT | 600 |
| ATGCTGGGTG | ACCGGCTGGG | GAGACATTGC | AGACCACACG | CCACTGCCCC CACCCTACCA | 660 |
| CCTGCAGGAG | GTGGAGGTCC | CCATCGTGGG | GAACAGGGAG | TGTAATTGTC ACTATCAGAC | 720 |
| CATTCTTGAG | CAAGACGATG | AGGTCATCAA | GCAGGACATG | CTGTGTGCCG GGAGCGAGGG | 780 |
| CCACGACTCC | TGCCAGATGG | ACTCCGGGGG | CCCCCTCGTG | TGCAGATGGA AGTGCACCTG | 840 |
| GATCCAAGTG | GGGGTCGTGA | GCTGGGGCTA | TGGCTGCGGT | TACAACCTCC CTGGGGTGTA | 900 |
| TGCCCGCGTG | ACGAGCTACG | TGTCCTGGAT | CCACCAGCAC | ATCCCTCTGT CCCCCGGACC | 960 |
| CTAGAAGGGA | CACACGTCAG | TCTTCCTTGT | CTCATCACTG | CGTGTTCCTG CGCGGTGGCA | 1020 |
| GGGGGAGCGG | GGAGAAGTCC | GGGGTCTCGG | ATGCCTGCTT | GGAATTGGAT TCTTATTAAA | 1080 |
| CATGCTGGGA | AAACC | | | | 1095 |

(2) INFORMATION FOR SEQ ID NO:10:

(i) SEQUENCE CHARACTERISTICS:
        (A) LENGTH: 269 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

Met Ala Pro Leu Ile Arg Met Leu Asp Leu Leu Gly Thr Leu Ser Pro
 1               5                  10                  15

Lys Val Gly Ile Val Gly Gly Cys Lys Val Pro Ala Arg Arg Tyr Pro
                20                  25                  30

Trp Gln Val Ser Leu Arg Phe His Gly Met Gly Ser Gly Gln Trp Gln
            35                  40                  45

His Ile Cys Gly Gly Ser Leu Ile His Pro Gln Trp Val Leu Thr Ala
        50                  55                  60

Ala His Cys Val Glu Leu Glu Gly Leu Glu Ala Ala Thr Leu Arg Val
65                  70                  75                  80

Gln Val Gly Gln Leu Arg Leu Tyr Asp His Asp Gln Leu Cys Asn Val
                85                  90                  95

Thr Glu Ile Ile Arg His Pro Asn Phe Asn Met Ser Trp Tyr Gly Trp
                100                 105                 110

```
Asp Thr Ala Asp Ile Ala Leu Leu Lys Leu Glu Ala Pro Leu Thr Leu
        115                 120                 125

Ser Glu Asp Val Asn Leu Val Ser Leu Pro Ser Pro Ser Leu Ile Val
    130                 135                 140

Pro Pro Gly Met Leu Cys Trp Val Thr Gly Trp Gly Asp Ile Ala Asp
145                 150                 155                 160

His Thr Pro Leu Pro Pro Tyr His Leu Gln Glu Val Glu Val Pro
            165                 170                 175

Ile Val Gly Asn Arg Glu Cys Asn Cys His Tyr Gln Thr Ile Leu Glu
                180                 185                 190

Gln Asp Asp Glu Val Ile Lys Gln Asp Met Leu Cys Ala Gly Ser Glu
        195                 200                 205

Gly His Asp Ser Cys Gln Met Asp Ser Gly Gly Pro Leu Val Cys Arg
210                 215                 220

Trp Lys Cys Thr Trp Ile Gln Val Gly Val Val Ser Trp Gly Tyr Gly
225                 230                 235                 240

Cys Gly Tyr Asn Leu Pro Gly Val Tyr Ala Arg Val Thr Ser Tyr Val
            245                 250                 255

Ser Trp Ile His Gln His Ile Pro Leu Ser Pro Gly Pro
        260                 265
```

(2) INFORMATION FOR SEQ ID NO:11:

(i) SEQUENCE CHARACTERISTICS:
        (A) LENGTH: 1154 base pairs
        (B) TYPE: nucleic acid
        (C) STRANDEDNESS: single
        (D) TOPOLOGY: linear (xi) SEQUENCE DESCRIPTION: SEQ ID NO:11:

```
GGAATTCCGT GGCCAGGATG CTGAGCCTGC TGCTGCTGGC GCTGCCCGTC CTGGCGAGCC    60

GCGCCTACGC GGCCCCTGCC CCAGTCCAGG CCCTGCAGCA AGCGGGTATC GTCGGGGGTC   120

AGGAGGCCCC CAGGAGCAAG TGGCCCTGGC AGGTGAGCCT GAGAGTCCGC GACCGATACT   180

GGATGCACTT CTGCGGGGGC TCCCTCATCC ACCCCCAGTG GGTGCTGACC GCGGCGCACT   240

GCCTGGGACC GGACGTCAAG GATCTGGCCA CCCTCAGGGT GCAACTGCGG GAGCAGCACC   300

TCTACTACCA GGACCAGCTG CTGCCAGTCA GCAGGATCAT CGTGCACCCA CAGTTCTACA   360

TCATCCAGAC TGGAGCGGAT ATCGCCCTGC TGGAGCTGGA GGAGCCCGTG AACATCTCCA   420

GCCGCGTCCA CACGGTCATG CTGCCCCCTG CCTCGGAGAC CTTCCCCCCG GGGATGCCGT   480

GCTGGGTCAC TGGCTGGGGC GATGTGGACA ATGATGAGCC CTCCCACCG CCATTTCCCC   540

TGAAGCAGGT GAAGGTCCCC ATAATGGAAA ACCACATTTG TGACGCAAAA TACCACCTTG   600

GCGCCTACAC GGGAGACGAC GTCCGCATCA TCCGTGACGA CATGCTGTGT GCCGGGAACA   660

GCCAGAGGGA CTCCTGCAAG GGCGACTCTG GAGGGCCCCT GGTGTGCAAG GTGAATGGCA   720

CCTGGCTACA GGCGGGCGTG GTCAGCTGGG ACGAGGGCTG TGCCCAGCCC AACGGCCTG   780

GCATCTACAC CCGTGTCACC TACTACTTGG ACTGGATCCA CCACTATGTC CCCAAAAAGC   840

CGTGAGTCAG GCCTGGGTGT GCCACCTGGG TCACTGGAGG ACCAACCCCT GCTGTCCAAA   900

ACACCACTGC TTCCTACCCA GGTGGCGACT GCCCCCCACA CCTTCCCTGC CCCGTCCTGA   960

GTGCCCCTTC CTGTCCTAAG CCCCCTGCTC TCTTCTGAGC CCCTTCCCCT GTCCTGAGGA  1020

CCCTTCCCCA TCCTGAGCCC CCTTCCCTGT CCTAAGCCTG ACGCCTGCAC TGCTCCGGCC  1080

CTCCCCTGCC CAGGCAGCTG GTGGTGGGCG CTAATCCTCC TGAGTGCTGG ACCTCATTAA  1140
```

AGTGCATGGA AATC                                                    1154

(2) INFORMATION FOR SEQ ID NO:12:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

Met Leu Ser Leu Leu Leu Ala Leu Pro Val Leu Ala Ser Arg Ala
 1               5                  10                  15

Tyr Ala Ala Pro Ala Pro Val Gln Ala Leu Gln Gln Ala Gly Ile Val
            20                  25                  30

Gly Gly Gln Glu Ala Pro Arg Ser Lys Trp Pro Trp Gln Val Ser Leu
        35                  40                  45

Arg Val Arg Asp Arg Tyr Trp Met His Phe Cys Gly Gly Ser Leu Ile
    50                  55                  60

His Pro Gln Trp Val Leu Thr Ala Ala His Cys Leu Gly Pro Asp Val
65                  70                  75                  80

Lys Asp Leu Ala Thr Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
        115                 120                 125

Glu Pro Val Asn Ile Ser Ser Arg Val His Thr Val Met Leu Pro Pro
    130                 135                 140

Ala Ser Glu Thr Phe Pro Pro Gly Met Pro Cys Trp Val Thr Gly Trp
145                 150                 155                 160

Gly Asp Val Asp Asn Asp Glu Pro Leu Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Ile Arg Asp Asp
        195                 200                 205

Met Leu Cys Ala Gly Asn Ser Gln Arg Asp Ser Cys Lys Gly Asp Ser
210                 215                 220

Gly Gly Pro Leu Val Cys Lys Val Asn Gly Thr Trp Leu Gln Ala Gly
225                 230                 235                 240

Val Val Ser Trp Asp Glu Gly Cys Ala Gln Pro Asn Arg Pro Gly Ile
            245                 250                 255

Tyr Thr Arg Val Thr Tyr Tyr Leu Asp Trp Ile His His Tyr Val Pro
        260                 265                 270

Lys Lys Pro
        275

(2) INFORMATION FOR SEQ ID NO:13:

(i) SEQUENCE CHARACTERISTICS:
        (A) LENGTH: 1137 base pairs
        (B) TYPE: nucleic acid
        (C) STRANDEDNESS: single
        (D) TOPOLOGY: linear (xi) SEQUENCE DESCRIPTION: SEQ ID NO:13:

```
TGAATCTGCT GCTGCTGGCG CTGCCCGTCC TGGCGAGCCG CGCCTACGCG GCCCCTGCCC      60

CAGGCCAGGC CCTGCAGCGA GTGGGCATCG TCGGGGGTCA GGAGGCCCCC AGGAGCAAGT     120

GGCCCTGGCA GGTGAGCCTG AGAGTCCACG GCCCATACTG GATGCACTTC TGCGGGGGCT     180

CCCTCATCCA CCCCCAGTGG GTGCTGACCG CAGCGCACTG CGTGGGACCG GACGTCAAGG     240

ATCTGGCCGC CCTCAGGGTG CAACTGCGGG AGCAGCACCT CTACTACCAG GACCAGCTGC     300

TGCCGGTCAG CAGGATCATC GTGCACCCAC AGTTCTACAC CGCCCAGATC GGAGCGGACA     360

TCGCCCTGCT GGAGCTGGAG GAGCCGGTGA ACGTCTCCAG CCACGTCCAC ACGGTCACCC     420

TGCCCCCTGC CTCAGAGACC TTCCCCCCGG GGATGCCGTG CTGGGTCACT GGCTGGGGCG     480

ATGTGGACAA TGATGAGCGC CTCCCACCGC CATTTCCTCT GAAGCAGGTG AAGGTCCCCA     540

TAATGGAAAA CCACATTTGT GACGCAAAAT ACCACCTTGG CGCCTACACG GGAGACGACG     600

TCCGCATCGT CCGTGACGAC ATGCTGTGTG CCGGGAACAC CCGGAGGGAC TCATGCCAGG     660

GCGACTCCGG AGGGCCCCTG GTGTGCAAGG TGAATGGCAC CTGGCTGCAG GCGGGCGTGG     720

TCAGCTGGGG CGAGGGCTGT GCCCAGCCCA ACCGGCCTGG CATCTACACC CGTGTCACCT     780

ACTACTTGGA CTGGATCCAC CACTATGTCC CCAAAAAGCC GTGAGTCAGG CCTGGGTTGG     840

CCACCTGGGT CACTGGAGGA CCAACCCCTG CTGTCCAAAA CACCACTGCT TCCTACCCAG     900

GTGGCGACTG CCCCCACAC CTTCCCTGCC CCGTCCTGAG TGCCCCTTCC TGTCCTAAGC     960

CCCCTGCTCT CTTCTGAGCC CCTTCCCCTG TCCTGAGGAC CCTTCCCTAT CCTGAGCCCC    1020

CTTCCCTGTC CTAAGCCCTGA CGCCTGCACC GGGCCCTCCA GCCCTCCCCT GCCCAGATAG    1080

CTGGTGGTGG GCGCTAATCC TCCTGAGTGC TGGACCTCAT TAAAGTGCAT GGAAATC      1137

(2) INFORMATION FOR SEQ ID NO:14:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Asn Leu Leu Leu Ala Leu Pro Val Leu Ala Ser Arg Ala Tyr Ala
1               5                   10                  15

Ala Pro Ala Pro Gly Gln Ala Leu Gln Arg Val Gly Ile Val Gly Gly
            20                  25                  30

Gln Glu Ala Pro Arg Ser Lys Trp Pro Trp Gln Val Ser Leu Arg Val
        35                  40                  45

His Gly Pro Tyr Trp Met His Phe Cys Gly Gly Ser Leu Ile His Pro
    50                  55                  60

Gln Trp Val Leu Thr Ala Ala His Cys Val Gly Pro Asp Val Lys Asp
65                  70                  75                  80

Leu Ala Ala Leu Arg Val Gln Leu Arg Glu Gln His Leu Tyr Tyr Gln
                85                  90                  95

Asp Gln Leu Leu Pro Val Ser Arg Ile Ile Val His Pro Gln Phe Tyr
            100                 105                 110

Thr Ala Gln Ile Gly Ala Asp Ile Ala Leu Leu Glu Leu Glu Glu Pro
        115                 120                 125

Val Asn Val Ser Ser His Val His Thr Val Thr Leu Pro Pro Ala Ser
    130                 135                 140

Glu Thr Phe Pro Pro Gly Met Pro Cys Trp Val Thr Gly Trp Gly Asp
145                 150                 155                 160
```

Val Asp Asn Asp Glu Arg Leu Pro Pro Phe Pro Leu Lys Gln Val
            165                 170                 175

Lys Val Pro Ile Met Glu Asn His Ile Cys Asp Ala Lys Tyr His Leu
            180                 185                 190

Gly Ala Tyr Thr Gly Asp Asp Val Arg Ile Val Arg Asp Asp Met Leu
            195                 200                 205

Cys Ala Gly Asn Thr Arg Arg Asp Ser Cys Gln Gly Asp Ser Gly Gly
            210                 215                 220

Pro Leu Val Cys Lys Val Asn Gly Thr Trp Leu Gln Ala Gly Val Val
225                 230                 235                 240

Ser Trp Gly Glu Gly Cys Ala Gln Pro Asn Arg Pro Gly Ile Tyr Thr
            245                 250                 255

Arg Val Thr Tyr Tyr Leu Asp Trp Ile His His Tyr Val Pro Lys Lys
            260                 265                 270

Pro (2) INFORMATION FOR SEQ ID NO:15:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (xi) SEQUENCE DESCRIPTION: SEQ ID NO:15:

```
GCTGAATCTG CTGCTGCTGG CGCTGCCCGT CCTGGCGAGC CGCGCCTACG CGGCCCCTGC    60

CCCAGGCCAG GCCCTGCAGC GAGTGGGCAT CGTTGGGGGT CAGGAGGCCC CCAGGAGCAA   120

GTGGCCCTGG CAGGTGAGCC TGAGAGTCCA CGGCCCATAC TGGATGCACT TCTGCGGGGG   180

CTCCCTCATC CACCCCCAGT GGGTGCTGAC CGCAGCGCAC TGCGTGGGAC CGGACGTCAA   240

GGATCTGGCC GCCCTCAGGG TGCAACTGCG GGAGCAGCAC CTCTACTACC AGGACCAGCT   300

GCTGCCGGTC AGCAGGATCA TCGTGCACCC ACAGTTCTAC ACCGCCCAGA TCGGAGCGGA   360

CATCGCCCTG CTGGAGCTGG AGGAGCCGGT GAAGGTCTCC AGCCACGTCC ACACGGTCAC   420

CCTGCCCCCT GCCTCAGAGA CCTTCCCCCC GGGGATGCCG TGCTGGGTCA CTGGCTGGGG   480

CGATGTGGAC AATGATGAGC GCCTCCCACC GCCATTTCCT CTGAAGCAGG TGAAGGTCCC   540

CATAATGGAA AACCACATTT GTGACGCAAA ATACCACCTT GGCGCCTACA CGGGAGACGA   600

CGTCCGCATC GTCCGTGACG ACATGCTGTG TGCCGGGAAC ACCCGGAGGG ACTCATGCCA   660

GGGCGACTCC GGAGGGCCCC TGGTGTGCAA GGTGAATGGC ACCTGGCTGC AGGCGGGCGT   720

GGTCAGCTGG GGCGAGGGCT GTGCCCAGCC CAACCGGCCT GGCATCTACA CCCGTGTCAC   780

CTACTACTTG GACTGGATCC ACCACTATGT CCCCAAAAAG CCGTGAGTCA GGCCTGGGTT   840

GGCCACCTGG GTCACTGGAG GACCAACCCC TGCTGTCCAA ACACCACTG CTTCCTACCC   900

AGGTGGCGAC TGCCCCCCAC ACCTTCCCTG CCCCGTCCTG AGTGCCCCTT CCTGTCCTAA   960

GCCCCCTGCT CTCTTCTGAG CCCCTTCCCC TGTCCTGAGG ACCCTTCCCC ATCCTGAGCC  1020

CCCTTCCCTG TCCTAAGCCT GACGCCTGCA CCGGGCCCTC CGGCCCTCCC CTGCCCAGGC  1080

AGCTGGTGGT GGGCGCTAAT CCTCCTGAGT GCTGGACCTC ATTAAAGT              1128
```

(2) INFORMATION FOR SEQ ID NO:16:

(i) SEQUENCE CHARACTERISTICS:
        (A) LENGTH: 274 amino acids
        (B) TYPE: amino acid
        (C) STRANDEDNESS: single (D) TOPOLOGY: linear (ii) MOLECULE TYPE: None (xi) SEQUENCE DESCRIPTION: SEQ ID NO:16:

```
Leu Asn Leu Leu Leu Ala Leu Pro Val Leu Ala Ser Arg Ala Tyr
  1               5                  10                  15

Ala Ala Pro Ala Pro Gly Gln Ala Leu Gln Arg Val Gly Ile Val Gly
                 20                  25                  30

Gly Gln Glu Ala Pro Arg Ser Lys Trp Pro Trp Gln Val Ser Leu Arg
             35                  40                  45

Val His Gly Pro Tyr Trp Met His Phe Cys Gly Gly Ser Leu Ile His
         50                  55                  60

Pro Gln Trp Val Leu Thr Ala Ala His Cys Val Gly Pro Asp Val Lys
 65                  70                  75                  80

Asp Leu Ala Ala Leu Arg Val Gln Leu Arg Glu Gln His Leu Tyr Tyr
                 85                  90                  95

Gln Asp Gln Leu Leu Pro Val Ser Arg Ile Ile Val His Pro Gln Phe
            100                 105                 110

Tyr Thr Ala Gln Ile Gly Ala Asp Ile Ala Leu Leu Glu Leu Glu Glu
        115                 120                 125

Pro Val Lys Val Ser Ser His Val His Thr Val Thr Leu Pro Pro Ala
130                 135                 140

Ser Glu Thr Phe Pro Pro Gly Met Pro Cys Trp Val Thr Gly Trp Gly
145                 150                 155                 160

Asp Val Asp Asn Asp Glu Arg Leu Pro Pro Pro Phe Pro Leu Lys Gln
                165                 170                 175

Val Lys Val Pro Ile Met Glu Asn His Ile Cys Asp Ala Lys Tyr His
            180                 185                 190

Leu Gly Ala Tyr Thr Gly Asp Asp Val Arg Ile Val Arg Asp Asp Met
        195                 200                 205

Leu Cys Ala Gly Asn Thr Arg Arg Asp Ser Cys Gln Gly Asp Ser Gly
210                 215                 220

Gly Pro Leu Val Cys Lys Val Asn Gly Thr Trp Leu Gln Ala Gly Val
225                 230                 235                 240

Val Ser Trp Gly Glu Gly Cys Ala Gln Pro Asn Arg Pro Gly Ile Tyr
                245                 250                 255

Thr Arg Val Thr Tyr Tyr Leu Asp Trp Ile His His Tyr Val Pro Lys
            260                 265                 270

Lys Pro
```

(2) INFORMATION FOR SEQ ID NO:17:

(i) SEQUENCE CHARACTERISTICS:
        (A) LENGTH: 1081 base pairs
        (B) TYPE: nucleic acid
        (C) STRANDEDNESS: single
        (D) TOPOLOGY: linear (xi) SEQUENCE DESCRIPTION: SEQ ID NO:17:

```
GCTGCCCGTC CTGGCGAGCC GCGCCTACGC GGCCCCTGCC CCAGGCCAGG CCCTGCAGCG    60

AGTGGGCATC GTTGGGGGTC AGGAGGCCCC CAGGAGCAAG TGGCCCTGGC AGGTGAGCCT   120

GAGAGTCCGC GACCGATACT GGATGCACTT CTGCGGGGGC TCCCTCATCC ACCCCCAGTG   180

GGTGCTGACC GCAGCGCACT GCGTGGGACC GGACGTCAAG GATCTGGCCG CCCTCAGGGT   240

GCAACTGCGG GAGCAGCACC TCTACTACCA GGACCAGCTG CTGCCGGTCA GCAGGATCAT   300
```

-continued

```
CGTGCACCCA CAGTTCTACA CCGCCCAGAT CGGAGCGGAC ATCGCCCTGC TGGAGCTGGA      360

GGAGCCGGTG AAGGTCTCCA GCCACGTCCA CACGGTCACC CTGCCCCCTG CCTCAGAGAC      420

CTTCCCCCCG GGGATGCCGT GCTGGGTCAC TGGCTGGGGC GATGTGGACA ATGATGAGCG      480

CCTCCCACCG CCATTTCCTC TGAAGCAGGT GAAGGTCCCC ATAATGGAAA ACCACATTTG      540

TGACGCAAAA TACCACCTTG GCGCCTACAC GGGAGACGAC GTCCGCATCG TCCGTGACGA      600

CATGCTGTGT GCCGGGAACA CCCGGAGGGA CTCATGCCAG GGCGACTCCG GAGGGCCCCT      660

GGTGTGCAAG GTGAATGGCA CCTGGCTGCA GGCGGGCGTG GTCAGCTGGG GCGAGGGCTG      720

TGCCCAGCCC AACCGGCCTG GCATCTACAC CCGTGTCACC TACTACTTGG ACTGGATCCA      780

CCACTATGTC CCCAAAAAGC CGTGAGTCAG GCCTGGGGTG TCCACCTGGG TCACTGGAGG      840

ACCAGCCCCT CCTGTCCAAA ACACCACTGC TTCCTACCCA GGCGGCGACT GCCCCCCACA      900

CCTTCCCTGC CCCGTCCTGA GTGCCCCTTC CTGTCCTAAG CCCCCTGCTC TCTTCTGAGC      960

CCCTTCCCCT GTCCTGAGGA CCCTTCCCCA TCCTGAGCCC CCTTCCCTGT CCTAAGCCTG     1020

ACGCCTGCAC CGGGCCCTCC GGCCCTCCCC TGCCCAGGCA GCTGGTGGTG GGCGCTAATC     1080

C                                                                    1081
```

(2) INFORMATION FOR SEQ ID NO:18:

(i) SEQUENCE CHARACTERISTICS:
       (A) LENGTH: 267 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:18:

```
Leu Pro Val Leu Ala Ser Arg Ala Tyr Ala Ala Pro Ala Pro Gly Gln
  1               5                  10                  15

Ala Leu Gln Arg Val Gly Ile Val Gly Gln Glu Ala Pro Arg Ser
                 20                  25                  30

Lys Trp Pro Trp Gln Val Ser Leu Arg Val Arg Asp Arg Tyr Trp Met
             35                  40                  45

His Phe Cys Gly Gly Ser Leu Ile His Pro Gln Trp Val Leu Thr Ala
         50                  55                  60

Ala His Cys Val Gly Pro Asp Val Lys Asp Leu Ala Ala Leu Arg Val
 65                  70                  75                  80

Gln Leu Arg Glu Gln His Leu Tyr Tyr Gln Asp Gln Leu Leu Pro Val
                 85                  90                  95

Ser Arg Ile Ile Val His Pro Gln Phe Tyr Thr Ala Gln Ile Gly Ala
            100                 105                 110

Asp Ile Ala Leu Leu Glu Leu Glu Glu Pro Val Lys Val Ser Ser His
            115                 120                 125

Val His Thr Val Thr Leu Pro Pro Ala Ser Glu Thr Phe Pro Pro Gly
        130                 135                 140

Met Pro Cys Trp Val Thr Gly Trp Gly Asp Val Asp Asn Asp Glu Arg
145                 150                 155                 160

Leu Pro Pro Pro Phe Pro Leu Lys Gln Val Lys Val Pro Ile Met Glu
                165                 170                 175

Asn His Ile Cys Asp Ala Lys Tyr His Leu Gly Ala Tyr Thr Gly Asp
            180                 185                 190

Asp Val Arg Ile Val Arg Asp Asp Met Leu Cys Ala Gly Asn Thr Arg
            195                 200                 205
```

```
Arg Asp Ser Cys Gln Gly Asp Ser Gly Gly Pro Leu Val Cys Lys Val
210                 215                 220

Asn Gly Thr Trp Leu Gln Ala Gly Val Val Ser Trp Gly Glu Gly Cys
225                 230                 235                 240

Ala Gln Pro Asn Arg Pro Gly Ile Tyr Thr Arg Val Thr Tyr Tyr Leu
                245                 250                 255

Asp Trp Ile His His Tyr Val Pro Lys Lys Pro
            260                 265
```

(2) INFORMATION FOR SEQ ID NO:19:

(i) SEQUENCE CHARACTERISTICS:
        (A) LENGTH: 3757 base pairs
        (B) TYPE: nucleic acid
        (C) STRANDEDNESS: single
        (D) TOPOLOGY: linear (xi) SEQUENCE DESCRIPTION: SEQ ID NO:19:

```
GACGACCACT GCCAGGGACG AAAGTGCAAT GCGGCATACC TCAGTGGCGT GGAGTGCAGG      60

TATACAGATT AATCCGGCAG CGTCCGTCGT TGTTGATATT GCTTATGAAG GCTCCGGCAG     120

TGGCGACTGG CGTACTGACG GATTCATCGT TGGGGTCGGT TATAAATTCT GATTAGCCAG     180

GTAACACAGT GTTATGACAG CCCGCCGGAA CCGGTGGGCT TTTTTGTGGG GTGAATATGG     240

CAGTAAAGAT TTCAGGAGTC CTGAAAGACG GCACAGGAAA ACCGGTACAG AACTGCACCA     300

TTCAGCTGAA AGCCAGACGT AACAGCACCA CGGTGGTGGT GAACACGGTG GGCTCAGAGA     360

ATCCGGATGA AGCCTGCTTT TTTATACTAA GTTGGCATTA TAAAAAAGCA TTGCTTATCA     420

ATTTGTTGCA ACGAACAGGT CACTATCAGT CAAAATAAAA TCATTATTTG ATTTCAATTT     480

TGTCCCACTC CCTGCCTCTG TCATCACGAT ACTGTGATGC CATGGTGTCC GACTTATGCC     540

CGAGAAGATG TTGAGCAAAC TTATCGCTTA TCTGCTTCTC ATAGAGTCTT GCAGACAAAC     600

TGCGCAACTC GTGAAAGGTA GGCGGATCTG GGTCGACCTG CAGGTCAACG GATCCTCTCC     660

AGTGGAAAGC TGAGCCCAAC CCTGAGGACT CAGAGGATGC AAGATGAACG ACGCTGTTAC     720

CCATTGTGCT CTGCTCCTTG GGATGGCTCA CAGACACCAT CATCTCCTGT CCTGTCTCAC     780

TCTTGGGAAA TGTGTTAGAG TGTGTCAATA TGTCATGCTA GGGTGACACT GAGCCAGGAG     840

CCTTCTTGAG ACCTCTATAT CCCTGGGATG GGATCCCCAT CCCAATAGTT GGAAGGAGCA     900

GCGGCTCGGT GATGCAGAGC ACTCAACTGA GAGGCATCCT CAGTATGCGG TGCTCTGCCC     960

ACAGTGGACA GAGCAGACCT GGTGGAGGCA GAGCAGAGTA ACATCCTGAG CAGATGGGGG    1020

CCACGCCTGC CCAGGTCTCC TGATGTGGAG GGCTGCTTGT GGGACATCTG GCAAGCTCAG    1080

CATTTCCTTG GGCATTTCAC CGCTGAGGAA CAAGACATGA GGAGGAGGCA AATCTGAGAA    1140

GAGGCTACCA GCCTCCCCTC AGAAGATACC CCTTTCCAGG GAGGGCTGGG GATGACCACT    1200

GTCCTGCCAG CCCATCCACC CCACTACCTG ACTCTCCTAT CCTGGACCCA GAGCAGTTGC    1260

ATCTCTTAAC TCTGCCTTCC ATAGCCTGAA ATACCAAGAC TCTGTGTGTG TGTGTGTGTG    1320

TGTGTGTGTG TGTGTGTGTG TGTGTGTGTG TGTATGTGTA TGTGTGTGTG TATGACTGGT    1380

CCTCTCATTG TGCACTCAAC CGTGTGACCT GTGGTCATCA GAAGGGCATC TGGGTGGTGG    1440

GGACACATGT TACATGGAGG CCTTTGATCT AAATCACTAT TTCCTTTGTA TCTGGATTGG    1500

CGGGTGCTGT GTCCCTCCTC TCATGCACTC TGGTCTGGAG AATTAAAAAG GCAGAGGACA    1560

GCAGGCCAAG GAGAGAGGAG CAGAGACAGC TAAGGTAAAG TCCTGGTGTC TATATGTCAT    1620

CCTGAAGCAG AGTAACCAAG CTTGTGACCT TTGTAACCTG GTGCACCAAG CCCGCAGACT    1680

CCTGGGATGA ACCTGCCCTC CATCTCATGG GCCCTGGTTC CATTCTGGAC TTGATATTCT    1740
```

```
GCCAGCCCCA GTCCAGCCCT GTCTTCTAGC TGGACTCAGG CTGTGCTCCT CTCTGCTTCC    1800

AGATGCTGAA GCGGCGGCTG CTGCTGCTGT GGGCACTGTC CCTCCTGGCT AGTCTGGTGT    1860

ACTCAGCCCC TCGTAAGTTG TCTTGAGCCC TCCCTGTCTC TCCCTCACCT TCACAGGCCA    1920

CAGGAATGGG GAGTCTAGAG AATCCCAGGG TTAGCTCCAA TTCAGGAGGG GGCAAGGCAG    1980

GGCACAGAGG TTGCTTCTTG TCTCTCTCCA GGCCCAGCCA ATCAGCGAGT GGGCATCGTG    2040

GGAGGACATG AGGCTTCTGA GAGTAAGTGG CCCTGGCAGG TGAGCCTGAG ATTTAAATTA    2100

AACTACTGGA TACATTTCTG CGGAGGCTCT CTCATCCACC CACAGTGGGT GCTCACTGCG    2160

GCACACTGTG TGGGACCGTG AGTCTCCCTG GGCCTGGCAT GGTGGGACGG GATCTAGATT    2220

ATTCCCACCA TCCCCAGTGT TCCCGAGGAT GTGCCCATCC TGGCTGGAGC CTTCTGAGCA    2280

TGATTATACT CTTCTAGGCA CATCAAAAGC CCACAGCTCT TCCGGGTGCA GCTTCGTGAG    2340

CAGTATCTAT ACTATGGGGA CCAGCTCCTC TCTTTGAACC GGATCGTGGT GCACCCCCAC    2400

TATTACACGG CCGAGGGTGG GGCAGACGTT GCCCTGCTGG AGCTTGAGGT CCCTGTGAAT    2460

GTCTCCACCC ATATCCACCC CATATCCCTG CCCCCTGCCT CGGAGACCTT CCCCCCTGGG    2520

ACATCGTGCT GGGTGACAGG CTGGGCGAC ATTGATAATG ACGGTATGTG GCAAGGATAG    2580

CTGACAGTTA GGCAGGGACT AAGTCTCCTC CAATCCCAGC ATTGGAGGGT GGGCAGGGAT    2640

TCCAGTGGCT GGTTACTCTT GAGCCTCCCT CAAAGGCTGC ACTTGTCCCA CCCCAGAGCC    2700

TCTCCCACCT CCTTATCCTC TGAAGCAAGT GAAGGTTCCC ATTGTGGAAA ACAGCCTGTG    2760

TGACCGGAAG TACCACACTG GCCTCTACAC GGGAGATGAT TTTCCCATTG TCCATGATGG    2820

CATGCTGTGT GCTGGAAATA CCAGGAGAGA CTCCTGCCAG GTAGGTCCTG TGTCCTCCCT    2880

GCACCACACC CCATCTGGTC TCCATACTGT GTGCTGACCC CTGTCTTCTT CAGGGCGATT    2940

CAGGGGGGCC ACTGGTCTGC AAAGTGAAGG GTACCTGGCT GCAGGCAGGA GTGGTCAGCT    3000

GGGGTGAGGG CTGCGCACAG CCCAACAAGC CTGGCATCTA CACCCGGGTG ACATACTACT    3060

TAGACTGGAT CCACCGCTAT GTCCCTGAGC ATTCCTGAGA CCTATCCAGG GTCAGGCAAG    3120

AACCAGGGCC GTGCTGTCTT TAACTCACTG CTTCCTGGTC AGGTGGAACC CTTGCCTTCC    3180

TTGTCCTCTG TCTCCCCTGT CTACTAGGTG TCCCTCTGAG GCCCCCACCC CCCAGTTCCG    3240

TCTTGAGTCC CTAGCCATTC CGGTTCCCTC TTGCCTCCCA CCACATAATA GTTGCATTGT    3300

GTGGCTCCCT CTCTTCTGTG GCTCATTAAA GTACTTGAAA ACAGCTATTG GAGTTGCTTC    3360

AAGAGTTCAA GGTCATCCTT GTCTATGTAT TGAGGTCGAG GCCAGTCTGG GATATGTGAG    3420

GCACCATCCC AAGACCATAA AGATCAAAAA TAAGTTCATG CAGCGGCACA TTTGCCTGCT    3480

ACAGTACACA ACATCACATC TGGCTGCTCC AGTCATGCAG TGGTACATCT GGCTGCTCCA    3540

GTCACATAGG AGCACATCTG GCTGCTCCAG TCATGCAGTG GTACATCTGG CTGCTCCAGT    3600

CACATAGGAG CACATCTGGC TGCTCCAGTC ACTTTGCTTT GGGTATTCTC ATTTGAGCCT    3660

CTTGGCCCTT GGGTGCTCAT GGCCATTCCT GCACACACAC ATATGCTTAT ATCTGGAACT    3720

TTCTGCTGAA GGGAGCTGTT GGTTCATGAA TAGGCCC                             3757
```

(2) INFORMATION FOR SEQ ID NO:20:

(i) SEQUENCE CHARACTERISTICS:
        (A) LENGTH: 1108 base pairs
        (B) TYPE: nucleic acid
        (C) STRANDEDNESS: single
        (D) TOPOLOGY: linear (xi) SEQUENCE DESCRIPTION: SEQ ID NO:20:

```
ATCCAATTGA AGAGAGGAGC AGAGACAGCT AAGATGCTGA AGCGGCGGCT GCTGCTGCTG        60

TGGGCACTGT CCCTCCTGGC TAGTCTGGTG TACTCAGCCC CTCGCCCAGC CAATCAGCGA       120

GTGGGCATCG TGGGAGGACA TGAGGCTTCT GAGAGTAAGT GGCCCTGGCA GGTGAGCCTG       180

AGATTTAAAT TAAACTACTG GATACATTTC TGCGGAGGCT CTCTCATCCA CCCACAGTGG       240

GTGCTCACTG CGGCACACTG TGTGGGACCG CACATCAAAA GCCCACAGCT CTTCCGGGTG       300

CAGCTTCGTG AGCAGTATCT ATACTATGGG GACCAGCTCC TCTCTTTGAA CCGGATCGTG       360

GTGCACCCCC ACTATTACAC GGCCGAGGGT GGGGCAGACG TTGCCCTGCT GGAGCTTGAG       420

GTCCCTGTGA ATGTCTCCAC CCATATCCAC CCCATATCCC TGCCCCCTGC CTCGGAGACC       480

TTCCCCCCTG GGACATCGTG CTGGGTGACA GGCTGGGGCG ACATTGATAA TGACGAGCCT       540

CTCCCACCTC CTTATCCTCT GAAGCAAGTG AAGGTTCCCA TTGTGGAAAA CAGCCTGTGT       600

GACCGGAAGT ACCACACTGG CCTCTACACG GGAGATGATT TTCCCATTGT CCATGATGGC       660

ATGCTGTGTG CTGGAAATAC CAGGAGAGAC TCCTGCCAGG GCGATTCAGG GGGGCCACTG       720

GTCTGCAAAG TGAAGGGTAC CTGGCTGCAG GCAGGAGTGG TCAGCTGGGG TGAGGGCTGC       780

GCACAGCCCA ACAAGCCTGG CATCTACACC CGGGTGACAT ACTACTTAGA CTGGATCCAC       840

CGCTATGTCC CTGAGCATTC CTGAGACCTA TCCAGGGTCA GGCAAGAACC AGGGCCGTGC       900

TGTCTTTAAC TCACTGCTTC CTGGTCAGGT GGAACCCTTG CCTTCCTTGT CCTCTGTCTC       960

CCCTGTCTAC TAGGTGTCCC TCTGAGGCCC CCACCCCCCA GTTCCGTCTT GAGTCCCTAG      1020

CCATTCCGGT TCCCTCTTGC CTCCCACCAC ATAATAGTTG CATTGTGTGG CTCCCTCTCT      1080

TCTGTGGCTC ATTAAAGTAC TTGAAAAC                                        1108
```

(2) INFORMATION FOR SEQ ID NO:21:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:21:

```
Met Leu Lys Arg Arg Leu Leu Leu Leu Trp Ala Leu Ser Leu Leu Ala
 1               5                  10                  15

Ser Leu Val Tyr Ser Ala Pro Arg Pro Ala Asn Gln Arg Val Gly Ile
                20                  25                  30

Val Gly Gly His Glu Ala Ser Glu Ser Lys Trp Pro Trp Gln Val Ser
            35                  40                  45

Leu Arg Phe Lys Leu Asn Tyr Trp Ile His Phe Cys Gly Gly Ser Leu
        50                  55                  60

Ile His Pro Gln Trp Val Leu Thr Ala Ala His Cys Val Gly Pro His
65                  70                  75                  80

Ile Lys Ser Pro Gln Leu Phe Arg Val Gln Leu Arg Glu Gln Tyr Leu
                85                  90                  95

Tyr Tyr Gly Asp Gln Leu Leu Ser Leu Asn Arg Ile Val Val His Pro
            100                 105                 110

His Tyr Tyr Thr Ala Glu Gly Gly Ala Asp Val Ala Leu Leu Glu Leu
        115                 120                 125

Glu Val Pro Val Asn Val Ser Thr His Ile His Pro Ile Ser Leu Pro
    130                 135                 140

Pro Ala Ser Glu Thr Phe Pro Pro Gly Thr Ser Cys Trp Val Thr Gly
145                 150                 155                 160
```

```
Trp Gly Asp Ile Asp Asn Asp Glu Pro Leu Pro Pro Pro Tyr Pro Leu
            165                 170                 175

Lys Gln Val Lys Val Pro Ile Val Glu Asn Ser Leu Cys Asp Arg Lys
            180                 185                 190

Tyr His Thr Gly Leu Tyr Thr Gly Asp Asp Phe Pro Ile Val His Asp
            195                 200                 205

Gly Met Leu Cys Ala Gly Asn Thr Arg Arg Asp Ser Cys Gln Gly Asp
            210                 215                 220

Ser Gly Gly Pro Leu Val Cys Lys Val Lys Gly Thr Trp Leu Gln Ala
225                 230                 235                 240

Gly Val Val Ser Trp Gly Glu Gly Cys Ala Gln Pro Asn Lys Pro Gly
            245                 250                 255

Ile Tyr Thr Arg Val Thr Tyr Tyr Leu Asp Trp Ile His Arg Tyr Val
            260                 265                 270

Pro Glu His Ser
            275

(2) INFORMATION FOR SEQ ID NO:22:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:22:

Ala Pro Gly Pro Ala Met Thr Arg Glu Gly
1               5                   10

(2) INFORMATION FOR SEQ ID NO:23:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:23:

Asp Tyr Lys Asp Asp Asp Lys
1               5

(2) INFORMATION FOR SEQ ID NO:24:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:24:

Asp Asp Asp Asp Lys Ile
1               5

(2) INFORMATION FOR SEQ ID NO:25:

(i) SEQUENCE CHARACTERISTICS:
         (A) LENGTH: 4 amino acids
         (B) TYPE: amino acid
         (C) STRANDEDNESS: single
```

(D) TOPOLOGY: linear (ii) MOLECULE TYPE: None (xi) SEQUENCE DESCRIPTION: SEQ ID NO:25:

Ile Val Gly Gly
 1

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Leu Gly Ala Tyr Thr Gly Asp Asp Val Arg Ile Val Arg Asp
 1               5                  10

(2) INFORMATION FOR SEQ ID NO:27:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

Leu Gly Ala Tyr Thr Gly Asp Asp Val Arg Ile Ile Arg Asp
 1               5                  10

(2) INFORMATION FOR SEQ ID NO:28:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

Thr Gly Leu Tyr Thr Gly Asp Asp Phe Pro Ile Val His Asp
 1               5                  10

(2) INFORMATION FOR SEQ ID NO:29:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

Lys Gly Leu Ile Thr Gly Asp Asn Val His Ile Val Arg Asp
 1               5                  10

(2) INFORMATION FOR SEQ ID NO:30:

(i) SEQUENCE CHARACTERISTICS:
        (A) LENGTH: 18 amino acids
        (B) TYPE: amino acid
        (C) STRANDEDNESS: single (D) TOPOLOGY: linear (ii) MOLECULE TYPE: None (xi) SEQUENCE DESCRIPTION: SEQ ID NO:30:

Met Leu Lys Leu Leu Leu Leu Thr Leu Pro Leu Leu Ser Ser Leu Val
 1               5                  10                  15

His Ala (2) INFORMATION FOR SEQ ID NO:31:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:31:

Met Leu Lys Arg Arg Leu Leu Leu Leu Trp Ala Leu Ser Leu Leu Ala
 1               5                  10                  15

Ser Leu Val Thr Ser
            20

(2) INFORMATION FOR SEQ ID NO:32:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:32:

Met Leu Ser Leu Leu Leu Leu Ala Leu Pro Val Leu Ala Ser Arg Ala
 1               5                  10                  15

Thr Ala Ala Pro
            20

(2) INFORMATION FOR SEQ ID NO:33:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:33:

Met Leu Asn Leu Leu Leu Leu Ala Leu Pro Val Leu Ala Ser Arg Ala
 1               5                  10                  15

Tyr Ala Ala Pro
            20

(2) INFORMATION FOR SEQ ID NO:34:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:34:

```
Ala Pro Gly Pro Ala Met Thr Arg Glu Gly
  1               5                  10
```

(2) INFORMATION FOR SEQ ID NO:35:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:35:

```
Ala Pro Arg Pro Ala Asn Gln Arg Val Gly
  1               5                  10
```

(2) INFORMATION FOR SEQ ID NO:36:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:36:

```
Ala Pro Val Gln Ala Leu Gln Gln Ala Gly
  1               5                  10
```

(2) INFORMATION FOR SEQ ID NO:37:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:37:

```
Ala Pro Gly Gln Ala Leu Gln Arg Val Gly
  1               5                  10
```

(2) INFORMATION FOR SEQ ID NO:38:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:38:

GACGACGATG ACAAG                                              15

(2) INFORMATION FOR SEQ ID NO:39:

(i) SEQUENCE CHARACTERISTICS:
       (A) LENGTH: 55 base pairs
       (B) TYPE: nucleic acid
       (C) STRANDEDNESS: single
       (D) TOPOLOGY: linear (xi) SEQUENCE DESCRIPTION: SEQ ID NO:39:

CGGCCGACTA CAAGGACGAC GATGACAAGN NNNNNNNNNN NARGNNNNNN NNNGC    55

(2) INFORMATION FOR SEQ ID NO:40:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:40:

GGCCGCNNNN NNNNNCYTNN NNNNNNNNNN CTTGTCATCG TCGTCCTTGT AGTCGGCCGG    60

CT                                                                  62

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:41:

CCCAGCCGGC CGACTACAAG GACG                                          24

(2) INFORMATION FOR SEQ ID NO:42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:42:

TGTTCCTTTC TATGCGGCCC AGC                                           23

(2) INFORMATION FOR SEQ ID NO:43:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

Met Lys Met Ser Arg Leu Cys Leu Ser Val Ala Leu Leu Val Leu Leu
1               5                  10                  15

Gly Thr Leu Ala Ala Ser Thr Pro Gly Cys Asp Thr Ser Asn Gln Ala
            20                  25                  30

Lys Ala Gln Arg Pro Asp Phe Cys Leu Glu Pro Pro Tyr Thr Gly Pro
        35                  40                  45

Cys Lys Ala Arg Ile Ile Arg Tyr Phe Tyr Asn Ala Lys Ala Gly Leu
    50                  55                  60

Cys Gln Thr Phe Val Tyr Gly Gly Cys Arg Ala Lys Arg Asn Asn Phe
65                  70                  75                  80

Lys Ser Ala Glu Asp Cys Met Arg Thr Cys Gly Gly Ala Ile Gly Pro
                85                  90                  95

Trp Glu Asn Leu
            100

(2) INFORMATION FOR SEQ ID NO:44:

(i) SEQUENCE CHARACTERISTICS:
        (A) LENGTH: 246 amino acids
        (B) TYPE: amino acid
        (C) STRANDEDNESS: single -continued (D) TOPOLOGY: linear (ii) MOLECULE TYPE: None (xi) SEQUENCE DESCRIPTION: SEQ ID NO:44:

Met Ser Ala Leu Leu Ile Leu Ala Leu Val Gly Ala Ala Val Ala Phe
 1               5                  10                  15

Pro Leu Glu Asp Asp Lys Ile Val Gly Gly Tyr Thr Cys Pro Glu
            20                  25                  30

His Ser Val Pro Tyr Gln Val Ser Leu Asn Ser Gly Tyr His Phe Cys
        35                  40                  45

Gly Gly Ser Leu Ile Asn Asp Gln Trp Val Val Ser Ala Ala His Cys
 50                  55                  60

Tyr Lys Ser Arg Ile Gln Val Arg Leu Gly Glu His Asn Ile Asn Val
65                   70                  75                  80

Leu Glu Gly Asp Glu Gln Phe Ile Asn Ala Ala Lys Ile Ile Lys His
            85                  90                  95

Pro Asn Tyr Ser Ser Trp Thr Leu Asn Asn Asp Ile Met Leu Ile Lys
            100                 105                 110

Leu Ser Ser Pro Val Lys Leu Asn Ala Arg Val Ala Pro Val Ala Leu
            115                 120                 125

Pro Ser Ala Cys Ala Pro Ala Gly Thr Gln Cys Leu Ile Ser Gly Trp
130                 135                 140

Gly Asn Thr Leu Ser Asn Gly Val Asn Asn Pro Asp Leu Leu Gln Cys
145                 150                 155                 160

Val Asp Ala Pro Val Leu Ser Gln Ala Asp Cys Glu Ala Ala Tyr Pro
                165                 170                 175

Gly Glu Ile Thr Ser Ser Met Ile Cys Val Gly Phe Leu Glu Gly Gly
            180                 185                 190

Lys Asp Ser Cys Gln Gly Asp Ser Gly Gly Pro Val Val Cys Asn Gly
            195                 200                 205

Gln Leu Gln Gly Ile Val Ser Trp Gly Tyr Gly Cys Ala Leu Pro Asp
210                 215                 220

Asn Pro Gly Val Tyr Thr Lys Val Cys Asn Phe Val Gly Trp Ile Gln
225                 230                 235                 240

Asp Thr Ile Ala Ala Asn
            245

(2) INFORMATION FOR SEQ ID NO:45:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:45:

Ile Ile Gly Gly Arg Glu Cys Glu Lys Asn Ser His Pro Trp Gln Val
 1               5                  10                  15

Ala Ile Tyr His Tyr Ser Ser Phe Gln Cys Gly Gly Val Leu Val Asn
            20                  25                  30

Pro Lys Trp Val Leu Thr Ala Ala His Cys Lys Asn Asp Asn Tyr Glu
            35                  40                  45

Val Trp Leu Gly Arg His Asn Leu Phe Glu Asn Glu Asn Thr Ala Gln
            50                  55                  60

```
Phe Phe Gly Val Thr Ala Asp Phe Pro His Pro Gly Phe Asn Leu Ser
 65                  70                  75                  80

Ala Asp Gly Lys Asp Tyr Ser His Asp Leu Met Leu Leu Arg Leu Gln
                 85                  90                  95

Ser Pro Ala Lys Ile Thr Asp Ala Val Lys Val Leu Glu Leu Pro Thr
            100                 105                 110

Gln Glu Pro Glu Leu Gly Ser Thr Cys Glu Ala Ser Gly Trp Gly Ser
            115                 120                 125

Ile Glu Pro Gly Pro Asp Asx Phe Glu Phe Pro Asp Glu Ile Gln Cys
            130                 135                 140

Val Gln Leu Thr Leu Leu Gln Asn Thr Phe Cys Ala Asx Ala His Pro
145                 150                 155                 160

Asx Lys Val Thr Glu Ser Met Leu Cys Ala Gly Tyr Leu Pro Gly Gly
                165                 170                 175

Lys Asp Thr Cys Met Gly Asp Ser Gly Gly Pro Leu Ile Cys Asn Gly
                180                 185                 190

Met Trp Gln Gly Ile Thr Ser Trp Gly His Thr Pro Cys Gly Ser Ala
                195                 200                 205

Asn Lys Pro Ser Ile Tyr Thr Lys Leu Ile Phe Tyr Leu Asp Trp Ile
210                 215                 220

Asn Asx Thr Ile Thr Glu Asn Pro
225                 230
```

(2) INFORMATION FOR SEQ ID NO:46:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:46:

```
Met Thr Leu Gly Arg Arg Leu Ala Cys Leu Phe Leu Ala Cys Val Leu
  1               5                  10                  15

Pro Ala Leu Leu Leu Gly Gly Thr Ala Leu Ala Ser Glu Ile Val Gly
                 20                  25                  30

Gly Arg Arg Ala Arg Pro His Ala Trp Pro Phe Met Val Ser Leu Gln
             35                  40                  45

Leu Arg Gly Gly His Phe Cys Gly Ala Thr Leu Ile Ala Pro Asn Phe
         50                  55                  60

Val Met Ser Ala Ala His Cys Val Ala Asn Val Asn Val Arg Ala Val
 65                  70                  75                  80

Arg Val Val Leu Gly Ala His Asn Leu Ser Arg Arg Glu Pro Thr Arg
                 85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
            115                 120                 125

Ile Asn Ala Asn Val Gln Val Ala Gln Leu Pro Ala Gln Gly Arg Arg
            130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175
```

```
Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His
                260                 265
```

(2) INFORMATION FOR SEQ ID NO:47:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:47:

```
Met Gln Ala Leu Leu Phe Leu Met Ala Leu Leu Pro Ser Gly Ala
1               5                   10                  15

Gly Ala Glu Glu Ile Ile Gly Gly Val Glu Ser Ile Pro His Ser Arg
            20                  25                  30

Pro Tyr Met Ala His Leu Asp Ile Val Thr Glu Lys Gly Leu Arg Val
        35                  40                  45

Ile Cys Gly Gly Phe Leu Ile Ser Arg Gln Phe Val Leu Thr Ala Ala
    50                  55                  60

His Cys Lys Gly Arg Glu Ile Thr Val Ile Leu Gly Ala His Asp Val
65                  70                  75                  80

Arg Lys Arg Glu Ser Thr Gln Gln Lys Ile Lys Val Glu Lys Gln Ile
                85                  90                  95

Ile His Glu Ser Tyr Asn Ser Val Pro Asn Leu His Asp Ile Met Leu
                100                 105                 110

Leu Lys Leu Glu Lys Lys Val Glu Leu Thr Pro Ala Val Asn Val Val
            115                 120                 125

Pro Leu Pro Ser Pro Ser Asp Phe Ile His Pro Gly Ala Met Cys Trp
        130                 135                 140

Ala Ala Gly Trp Gly Lys Thr Gly Val Arg Asp Pro Thr Ser Tyr Thr
145                 150                 155                 160

Leu Arg Glu Val Glu Leu Arg Ile Met Asp Glu Lys Ala Cys Val Asp
                165                 170                 175

Tyr Arg Tyr Tyr Glu Tyr Lys Phe Gln Val Cys Val Gly Ser Pro Thr
                180                 185                 190

Thr Leu Arg Ala Ala Phe Met Gly Asp Ser Gly Gly Pro Leu Leu Cys
            195                 200                 205

Ala Gly Val Ala His Gly Ile Val Ser Tyr Gly His Pro Asp Ala Lys
        210                 215                 220

Pro Pro Ala Ile Phe Thr Arg Val Ser Thr Tyr Val Pro Trp Ile Asn
225                 230                 235                 240

Ala Val Ile Asn Thr Ser Ser
                245
```

(2) INFORMATION FOR SEQ ID NO:48:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:48:

```
Thr Asp Thr Glu Asp Lys Gly Glu Phe Leu Ser Glu Gly Gly Val
1               5                   10                  15

Arg Gly Pro Arg Val Val Glu Arg
            20
```

(2) INFORMATION FOR SEQ ID NO:49:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:49:

```
Thr Val Ala Thr Arg Asp Asn Cys Cys Ile Leu Asp Glu
1               5                   10
```

(2) INFORMATION FOR SEQ ID NO:50:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:50:

```
Ile Val Gly Gly Gln Xaa Ala Xaa Gly Asn Lys
1               5                   10
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:51:

```
Thr Asp Thr Glu Asp Lys Gly Glu Phe Leu
1               5                   10
```

(2) INFORMATION FOR SEQ ID NO:52:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:52:

Tyr Val Ala Thr Arg Asp Asn Xaa Xaa Ile Leu Asp Glu
1               5                   10

(2) INFORMATION FOR SEQ ID NO:53:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:53:

Arg Lys Glu Glu Pro Pro Ser Leu Arg Pro Ala Pro Pro
1               5                   10

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:54:

Ser Leu Ser Ser Arg Gln Ser Pro
1               5

(2) INFORMATION FOR SEQ ID NO:55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:55:

Cys Thr Ser Ser Arg Pro Ser Gly
1               5

(2) INFORMATION FOR SEQ ID NO:56:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:56:

Ser Gly Phe Gly Arg Leu Ser Asp
1               5

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:57:

Arg Ser Gln Thr Arg Lys Ser Lys
1               5

(2) INFORMATION FOR SEQ ID NO:58:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:58:

Lys Lys Gln Gly Arg Asp Ser Thr
1               5

(2) INFORMATION FOR SEQ ID NO:59:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:59:

Arg Lys Gln Lys Arg Arg Thr Glu
1               5

(2) INFORMATION FOR SEQ ID NO:60:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:60:

Pro Pro Ser Phe Arg Arg Ser Ser
1               5

(2) INFORMATION FOR SEQ ID NO:61:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:61:

Leu Pro Tyr Gly Arg Ala Thr Thr
1               5

(2) INFORMATION FOR SEQ ID NO:62:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:62:

```
Asn Thr Pro Thr Lys Leu Ser Pro
1               5
```

(2) INFORMATION FOR SEQ ID NO:63:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:63:

```
Arg Arg Pro Thr Lys Lys Asn Thr
1               5
```

(2) INFORMATION FOR SEQ ID NO:64:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:64:

```
Arg Gly Glu Lys Arg Ser Lys Ser
1               5
```

(2) INFORMATION FOR SEQ ID NO:65:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:65:

```
Met Leu Leu Ile Arg Thr Trp Glu
1               5
```

(2) INFORMATION FOR SEQ ID NO:66:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:66:

```
Val Thr Tyr Ala Arg Leu Cys Thr
1               5
```

(2) INFORMATION FOR SEQ ID NO:67:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:67:

```
Leu Ser Tyr Arg Lys Leu Arg Phe
1               5
```

(2) INFORMATION FOR SEQ ID NO:68:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:68:

```
Gly Thr Arg Arg Arg Glu Glu His
1               5
```

(2) INFORMATION FOR SEQ ID NO:69:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:69:

```
Asp Arg Lys Gly Arg Gln Gln Gln
1               5
```

(2) INFORMATION FOR SEQ ID NO:70:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:70:

```
Arg Tyr Pro Cys Arg Tyr Gly Leu
1               5
```

(2) INFORMATION FOR SEQ ID NO:71:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:71:

```
Lys Glu Glu Asn Arg Lys Asn Asn
1               5
```

(2) INFORMATION FOR SEQ ID NO:72:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:72:

```
Phe His Pro Ser Arg His Pro Pro
 1               5
```

(2) INFORMATION FOR SEQ ID NO:73:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:73:

```
Ile Ala Arg Glu Lys Gly Gln Gln
 1               5
```

(2) INFORMATION FOR SEQ ID NO:74:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:74:

```
Ile Cys Pro Pro Arg Leu Leu Gln
 1               5
```

MAST CELL PROTEASE THAT CLEAVES FIBRINOGEN

RELATED APPLICATIONS

This application claims priority under 35 USC §119(e) from U.S. Provisional patent application Ser. No. 60/032, 354, filed on Dec. 4, 1996, entitled MAST CELL PROTEASE THAT CLEAVES FIBRINOGEN. The contents of the provisional application are hereby expressly incorporated by reference.

GOVERNMENT SUPPORT

This work was funded in part by grant numbers AI-23483 and HL-36 110 from the National Institutes of Health. Accordingly, the United States Government may have certain rights to this invention.

FIELD OF THE INVENTION

This invention relates to compositions containing a mast cell protease and its derivatives, and methods for use thereof. The mast cell protease selectively cleaves fibrinogen in vitro and in vivo. Accordingly, the compositions of the invention are useful for modulating fibrin and platelet-mediated clot formation. This invention also relates to methods for preparing nearly any recombinant serine protease in an enzymatically inactive pseudo-zymogen form that can be purified and then activated when needed.

BACKGROUND OF THE INVENTION

The initiating event in many myocardial infarctions (heart attacks) is the formation of a blood clot (thrombus) formed primarily of fibrin and blood platelets in the coronary artery. Formation of a fibrin/platelet blood clot in the coronary or other artery has serious clinical consequences. If the clot is large and/or remains in position for an extended period of time, extensive damage in the infarct zone (i.e., the area of coagulation necrosis which results from an obstruction of blood circulation) may result. Accordingly, the current treatment for myocardial infarction involves rapidly dissolving the occluding thrombus by administering a thrombolytic agent (i.e., an agent that is capable of lysing the thrombus) and, thereby, restoring blood flow through the affected blood vessel. Due in part to the urgent need to restore blood flow in an occluded vessel, the principal focus for treating conditions that are mediated by thrombus formation has been the discovery of new and better thrombus-dissolving drugs, e.g., urokinase, streptokinase, and tissue-type plasminogen activator (t-PA). Significantly less effort has been directed to the discovery and/or development of drugs that prevent or inhibit thrombus formation in the first instance.

The formation of a thrombus involves the conversion of a soluble plasma protein (fibrinogen) into an insoluble protein (fibrin). The conversion of fibrinogen to fibrin is catalyzed by the enzyme thrombin, in accordance with a mechanism that is known in the art. Platelets adhere to fibrinogen via their $\alpha_{IIb}\beta_3$ integrin receptors and therefore contribute to thrombus which is initiated by the formation of cross-linked fibrin. Thus, in general, the strategies proposed for preventing fibrin/platelet clot formation have involved either the administration of a "maintenance" level of a thrombolytic agent (e.g., t-PA) to reduce the likelihood of reocclusion following treatment of acute infarction and/or the administration of anticoagulants (e.g., heparin glycosaminoglycan) to inhibit or prevent fibrin clot formation in parts of the circulatory system by increasing the rate of inactivation of thrombin by anti-thrombin III.

In view of the demonstrated utility of blood clot dissolving agents in treating conditions that are mediated by thrombus formation and in view of the many side effects of heparin glycosaminoglycan, a need still exists to develop new and useful agents that inhibit or prevent thrombus formation in the first instance. Preferably, such agents would selectively inhibit thrombus formation at its earliest stages, thereby requiring administration of relatively low doses of the agent and minimizing the likelihood of side reactions that may be associated with the administration of a high dosage of the therapeutic agent.

SUMMARY OF THE INVENTION

The invention involves in one respect the discovery that fibrinogen is the physiological substrate for mouse mast cell protease 7 ("mMCP-7") and that this and the homologs of mMCP-7 in other species (e.g., rat, gerbil, dog, human) can be used to prevent or inhibit fibrin clot formation in vitro or in vivo. Although not intending to be bound to a particular mechanism of action, it is believed that the tryptase proteins of the invention inhibit thrombus formation by reducing the circulating level of fibrinogen that can be processed by thrombin to form a fibrin clot and/or by modulating platelet aggregation since intact fibrinogen is needed for platelet aggregation. Accordingly, the tryptase proteins of the invention are useful for treating a variety of disorders that are mediated by undesirable thrombus clot formation. Such disorders include myocardial infarct and reocclusion following angioplasty. The tryptases are also useful for all surgical procedures that require that blood not clot.

As used herein, a "tryptase-7" protein refers to the enzymatically active "mature" mMCP-7 protein, its naturally occurring alleles, and homologs of the foregoing proteins in other species. The tryptase-7 proteins, like other serine proteases, are synthesized in cells as zymogens (i.e., in an enzymatically inactive precursor form) which include a hydrophobic "pre" peptide sequence (also referred to as a "signal sequence" or "signal peptide") and a "pro" sequence (also referred to as a "pro-peptide sequence") attached to the N-terminal portion of the mature protein. The nucleic acid and encoded protein sequence of the mMCP-7 zymogen from BALB/c mice are provided as SEQ ID NOS. 1, 2 and 3, and have been accorded GenBank Accession Nos. L00653 and L00654 (see also Hunt et al., J. Biol. Chem. 1996, 271:2851–2855 and McNeil et al., PNAS, 1992, 89:11174–11178). The GenBank accession numbers and reference citations for these and other mast cell protease nucleic acids and/or proteins are provided in Table 1, just before the Sequence Listing. In particular, Table 1 identifies the nucleic acid and encoded protein sequence of the following homologs of the mMCP-7 zymogen: rat (SEQ ID NOS. 4 and 5), gerbil (SEQ ID NOS. 7 and 8), and dog (SEQ ID NOS. 9 and 10). The protein sequences for the "mature" tryptase-7 proteins from mouse, rat, gerbil, and dog are as follows. Mouse: the protein encoded by nucleotides 111–845 of SEQ ID NO. 1, or amino acids 28–273 of SEQ ID NO. 3; rat: the protein encoded by nucleotides 83–847 of SEQ ID NO. 4, or amino acids 19–274 of SEQ ID NO. 5, or amino acids 18–273 of SEQ ID NO. 6; gerbil: the protein encoded by nucleotides 273–1007 of SEQ ID NO. 7, or amino acids 25–270 of SEQ ID NO. 8; dog: the protein encoded by nucleotides 104–838 of SEQ ID NO. 9, or amino acids 30–269 of SEQ ID NO. 10. By "mature", it is meant that the sequence represents the serine protease which is the enzymatically active form of the protein.

According to one aspect of the invention, a composition containing a tryptase-7 protein of the invention is provided.

The composition includes a therapeutically effective amount of a "tryptase-7" and a pharmaceutically acceptable carrier. The therapeutically effective amount is that amount necessary to decrease fibrinogen activity in the subject. Preferably, the therapeutically effective amount is that amount necessary to treat (inhibit or prevent) coagulation in a subject. In the preferred embodiments, 1 μg of recombinant mMCP-7 will degrade 10 μg of fibrinogen in 15 minutes or less time, even in the presence of serum proteins. In contrast to earlier reports describing a mast cell serine protease from human lung (Schwartz et al., J. Immunol. 1985, 135:2762–2767), the tryptase-7 proteins of the invention do not require a negatively-charged glycosaminoglycan (e.g., heparin) as a cofactor for enzymatic activity. Further, the tryptase-7 proteins of the invention selectively cleave fibrinogen with a specific enzyme activity that is at least 10-fold greater than the specific enzyme activity reported for a tryptase purified from human lung tryptase. In addition, the tryptase-7 proteins of the invention are capable of selectively cleaving fibrinogen in the presence of all serum proteins.

In the preferred embodiments, the tryptase-7 protein is encoded by an isolated nucleic acid sequence selected from the group consisting of: (a) a nucleic acid molecule having the sequence of SEQ ID NO. 1 (the sequence for the mMCP-7 cDNA) or 2 (the sequence for the mMCP-7 genomic DNA); (b) nucleic acid molecules having sequences that are allelic variants of the nucleic acid molecules of (a); (c) nucleic acid molecules that encode a tryptase-7 but that differ from the nucleic acid molecule of (a) and (b) due to the degeneracy of the genetic code; (d) a nucleic acid molecule having the sequence of SEQ ID NO. 4 (the sequence for the rat homolog of mMCP-7); (e) nucleic acid molecules that are allelic variants of the nucleic acid molecule of (d); (f) nucleic acid molecules that encode a tryptase-7 but that differ from the nucleic acid molecule of (d) and (e) due to the degeneracy of the genetic code; (g) a nucleic acid molecule having the sequence of SEQ ID NO. 7 (the sequence for the gerbil homolog of mMCP-7); (h) nucleic acid molecules that are allelic variants of the nucleic acid molecule of (g); (i) nucleic acid molecules that encode a tryptase-7 but that differ from the nucleic acid molecule of (g) and (h) due to the degeneracy of the genetic code; (j) a nucleic acid molecule having, the sequence of SEQ ID NO. 9 (the sequence for the dog homolog of mMCP-7); (k) nucleic acid molecules that are allelic variants of the nucleic acid molecule of (j); and (l) nucleic acid molecules that encode a tryptase-7 but that differ from the nucleic acid molecule of (j) and (k) due to the degeneracy of the genetic code. Thus, the tryptase-7 proteins of the invention embrace the naturally occurring murine tryptase-7, the naturally occurring rat, gerbil, and dog homologs of the murine tryptase-7, allelic variants of the foregoing, and other variants that are encoded by nucleotide sequences that differ from the sequences encoding the naturally-occurring tryptase-7 proteins due to the degeneracy of the genetic code.

In an alternative embodiment, the tryptase-7 proteins of the invention include chimeric proteins that contain (a) the amino acid sequence of a known human tryptase for all but the active site region of the protease and (b) the amino acids that reside in the substrate-binding pocket of mouse tryptase-7 and its varied homologs. The exemplary human tryptases include: (1) human mast cell tryptase α having GenBank Accession No. M30038 (SEQ 11) NOS. 11 and 12); (2) human mast cell tryptase I having GenBank Accession No. M33491 (SEQ ID NOS. 13 and 14); (3) human mast cell tryptase II/β having GenBank Accession No. M33492 (SEQ ID NOS. 15 and 16); and (4) human mast cell tryptase III having GenBank Accession No. M33493 (SEQ ID NOS. 17 and 18). The "active site region" in reference to the human tryptases and the amino acids that reside in the substrate-binding pocket of mMCP-7 are described in detail below. Of course, 1, 2, 3, 4, or 5 amino acids on either side of these active site region sequences can additionally be substituted in the human tryptase without adversely affecting the ability of the chimeric protein to selectively cleave fibrinogen. These "humanized" tryptase-7 proteins are capable of selectively cleaving fibrinogen in vitro and in vivo and are particularly useful in applications that require repetitive administration of the tryptase-7 to a human subject.

The tryptase-7 proteins of the invention further embrace proteins that are encoded by an isolated nucleic acid consisting essentially of the "mature" peptide portion of the initially translated protein. In the preferred embodiments, these mature proteins are placed in a pharmaceutically acceptable carrier that is suitable for administration to a human subject. With respect to mMCP-7, the entire cDNA is about 1300 nucleotides, including the polyA tail. The mature portion of mMCP-7 is encoded by about 740 nucleotides of the mRNA.

According to yet another aspect of the invention, the above-described tryptase-7 proteins to which a FLAG peptide is attached to its C terminus (and nucleic acids encoding same) are provided. Attachment of the FLAG peptide facilitates purification of the recombinant tryptase-7 using an anti-FLAG affinity chromatography column (See Example).

According to yet another aspect of the invention, a method for treating a blood clot (preventing the formation of a clot or inhibiting the further enlargement of the clot) in a subject is provided. The method involves administering to a subject in need of such treatment an isolated nucleic acid molecule that codes for a tryptase-7 or an expression product thereof, in an amount effective to cleave fibrinogen in said subject and, thereby, decrease fibrinogen activity to a clinically significant extent. Thus, the claimed invention embraces administering a nucleic acid encoding a humanized form of tryptase-7 to treat, for example, genetic conditions that are manifested by a predisposition to excessive clotting, as well as administering the encoded tryptase-7 protein to treat (prevent or inhibit) the formation of fibrin clot formation in a subject. Such a subject might be susceptible to, or afflicted with, a clinically undesirable fibrin clot, e.g., a subject experiencing or having a medical history that includes a myocardial infarct or a predisposition to an excessive clotting disorder. The nucleic acid containing molecule encoding tryptase-7 (preferably, the humanized tryptase-7) or the expression product thereof is administered to the subject in accordance with standard methods known to one of ordinary skill in the art for delivering nucleic acid or protein molecules to the vasculature. Preferably, the humanized tryptase-7 is the above-described chimeric protein that combines the amino acid sequence of a human tryptase (excluding the active site region) with the relevant amino acids that form the substrate-binding site of mMCP-7. Exemplary pharmaceutically acceptable carriers and modes of administration for the delivery of a nucleic acid or protein for treating a blood clot-associated disorder are known in the art. For example, pharmaceutically acceptable carriers and modes of administration for delivering a protein product (e.g., a thrombolytic agent) to treat a condition that is mediated by a clinically undesirable fibrin clot in a subject are described in at least the following United States patents:

U.S. Pat. No. 5,372,812, issued to Reed et al.; U.S. Pat. No. 5,385,732, issued to Anderson et al.; U.S. Pat. No. 5,239,058, issued to Vlasuk et al.; and U.S. Pat. No. 5,405,771, issued to Anderson et al.

According to yet another aspect of the invention, an expression cassette including a nucleic acid encoding a mature serine protease is provided. The expression cassettes of the invention are useful for purifying recombinant serine proteases (particularly, mast cell serine proteases) that are difficult to obtain in an isolated form from cells in culture. The expression cassettes of the invention include a nucleic acid encoding, from its 5' to 3' direction: (a) a "pre" sequence of a serine protease or other secreted protein; (b) a "pro" sequence of the same or a different serine protease; (c) an endopeptidase (e.g., enterokinase) cleavage domain; and (d) the mature serine protease. Preferably, the pro sequence is the endogenous pro sequence of the zymogen from which the mature serine protein is derived. Preferably, the pro sequence in the expression cassette for obtaining the pseudo-zymogen form of mMCP-7 should be A-P-G-P-A-M-T-R-E-G (SEQ ID NO. 22), whereas the pro sequence in the expression cassette for obtaining the pseudo-zymogen forms of the chromosome 14 family of serine proteases (e.g., mast cell chymases, cathepsin G, and certain granzymes) preferably should be E-E. The selection of the pre sequence is less critical; however, it is preferred that the pre sequence and pro sequence are endogenous to the zymogen from which the mature serine protein is expressed. A second expression cassette contains, in addition, the FLAG peptide (D-Y-K-D-D-D-K, SEQ ID NO. 23) at the C-terminus of the mature recombinant tryptase to facilitate its purification using an anti-FLAG-Ig affinity column. Preferably, the mature serine protease formed after enterokinase cleavage of the pro peptide possesses an N-terminal isoleucine residue that plays an important role in folding the mature serine protease into its enzymatically active conformation. In the preferred embodiments, the serine protease is a mast cell protease such as the murine tryptase-7, the rat homolog of the murine tryptase-7 ("rat tryptase-7"), the gerbil homolog of the murine tryptase-7 ("gerbil tryptase-7"), the dog homolog of the murine tryptase-7 ("dog tryptase-7"), or alleles of the foregoing proteins.

The enterokinase susceptibility domain is a preferred cleavage domain for use in accordance with the compositions and methods of the invention. The enterokinase susceptibility domain is well known in the art and refers to the amino acid sequence, Asp-Asp-Asp-Asp-Lys-Ile (SEQ ID NO. 24) or a similar sequence such as those described in Light et al., Anal. Biochem. 106:199 (1980) (a cluster of negatively charged amino acids followed by a positively charged amino acid), that is selectively cleaved by an enterokinase. The cloning and expression of various enzymatically active enterokinases and exemplary conditions for using these enzymes are described in International Application No. PCT/US94/00616 (Publication No. WO 94/16083), entitled "Cloning of Enterokinase and Method of Use" (Applicant Genetics Institute). Inclusion of the enterokinase susceptibility domain in the expression cassette facilitates isolation of the mature protein in an enzymatically active form.

The expression cassette is useful for producing the recombinant tryptase-7 proteins of the invention, as well as for producing other naturally secreted serine proteases that are otherwise difficult to isolate and/or express. The method for producing a recombinant serine protease involves the following steps: (1) culturing a host cell which expresses the polynucleotide of the above-described expression cassette in a medium under conditions that promote expression and secretion of the inactive pseudo-zymogen; (2) collecting and purifying the serine protease (e.g., by contacting the cleaved serine protease with an immobilized antibody that is capable of selectively absorbing the released serine protease from the culture medium or other solutes, followed by desorbing the adsorbed protease from the immobilized antibody); and (3) cleaving the enterokinase-susceptibility domain (e.g., by contacting the host cell expression product with an enterokinase at a pH from about 4.0 to about 6.0, preferably about pH 5.2). The mMCP-7 protein in its pseudo-zymogen form also can be purified using a heparin-Sepharose affinity column (See, e.g., Matsumato et al., J. Biol. Chem. 1995, 270:19524–19531). Such alternative purification procedures can be used to purify the tryptase-7 proteins described herein. Optionally, the method further includes the step of activating the cleaved (released) serine protease by, for example, increasing the pH of the medium to a neutral pH, typically about pH 7.0.

These and other aspects of the invention, as well as various advantages and utilities will be more apparent with reference to the detailed description of the preferred embodiments and the example.

All references, patents and patent publications identified in this document are incorporated in their entirety herein by reference.

DETAILED DESCRIPTION OF THE INVENTION

The present invention in one aspect involves the discovery that the physiological substrate for mouse mast cell protease 7 ("mMCP-7") is fibrinogen and that this and other "tryptase-7" proteins can be used to prevent or inhibit fibrin/platelet clot formation in vitro or in vivo. Although not intending to be bound to any particular mechanism or theory, it is believed that the tryptase-7 proteins inhibit clot formation by degrading fibrinogen and, thereby, reducing the concentration of fibrinogen that can be processed by thrombin to form a fibrin clot. It is also believed that the breakdown of fibrinogen results in decreased platelet aggregation. Accordingly, the tryptase-7 proteins of the invention are useful for treating a variety of disorders that are mediated by undesirable fibrin/platelet clot formation. Such disorders include myocardial infarct and reocclusion following angioplasty. The tryptases are also useful for all surgical procedures that require decreased blood clots. Lastly, recombinant mMCP-7 and its derivatives can be used to obtain protease inhibitors that are specific for this tryptase.

The tryptase-7 proteins of the invention are members of the serine protease superfamily. In particular, the tryptase-7 proteins are members of the trypsin-like serine protease family of proteins that are the major constituents of the secretory granules of mouse, rat, gerbil, dog, and human mast cells. Lung, heart, and skin mast cells in the BALB/c mouse express at least two tryptases [designated mouse mast cell protease 6 ("mMCP-6") and 7 ("mMCP-7")] which are 71% identical in terms of their overall amino acid sequences. This tryptase family of mast cell proteases has been implicated in the pathobiology of FcεRI-elicited responses in airways. Linkage analysis has implicated the region of chromosome 17 where the mMCP-6 and mMCP-7 genes reside as one of the candidate loci for the inheritance of intrinsic airway hyper responsiveness. In addition, the finding that the C57BL/6 mouse cannot express mMCP-7 because its gene possesses a point mutation at its exon 2/intron 2 splice site has been proposed as one of the reasons why the airway responsiveness of the C57BL/6 mouse to acetylcholine and 5-hydroxytryptamine is lower than that in other mouse strains. Although these results suggest an important role for the mMCP-7 protein in the pathobiology of FcεRI-elicited responses in airways, the inability to definitively identify the physiological substrate for mMCP-7 has prevented the development of therapeutic agents that mediate conditions attributable to an under- or overabundance of the mMCP-7 protein or its physiological substrate. mMCP-6 and mMCP-7 are stored in acidic granules in their mature, enzymatically active forms ionically bound to the glycosaminoglycan side chains of serglycin proteoglycans. (See, e.g., Ghildyal, et al., J. Exp. Med. 1996; 184:1061–1073). Although mMCP-6 and mMCP-7 are negatively charged at neutral pH, the two exocytosed tryptases differ in their ability to dissociate from serglycin proteoglycans outside of the mast cell. Thus, these proteases are metabolized quite differently in mice undergoing passive systemic anaphylaxis. Tongue, skin, spleen, and heart mast cells of normal BALB/c mice and spleen and liver mast cells of V3 mastocytosis mice contain substantial amounts of mMCP-6 and mMCP-7 in their secretory granules. Ten minutes after antigen is administered to IgE-sensitized mice, protease/proteoglycan macromolecular complexes appear in the extracellular matrix adjacent to the tissue mast cells. These complexes can be readily stained by anti-mMCP-6 Ig but not by anti-mMCP-7 Ig. In the case of IgE/antigentreated V3 mastocytosis mice, exocytosed mMCP-7 rapidly makes its way into the blood where it circulates for greater than one hour. This plasma form of mMCP-7 has an intact N-terminus, is properly-folded, enzymatically active, and not degraded. Despite the fact that as much as 20% of the proteins in the blood are protease inhibitors, plasma localized mMCP-7 does not rapidly form covalent complexes with any protease inhibitor in the blood of V3 mastocytosis mice.

It appears that mMCP-7 is initially targeted to the secretory granule of the mast cell in its inactive zymogen form possessing a pro-peptide. However, N-terminal amino acid analyses of the varied proteins in the granules of varied mouse mast cells have indicated that mMCP-7 is stored in its mature form lacking the pro-peptide. Thus, only mature enzymatically-active mMCP-7 is released when the mast cell is activated through it high affinity IgF receptors. Modeling and site-directed mutagenesis analysis of recombinant pro-mMCP-7 (i.e., the expressed protein with its normal "pro-peptide" sequence) suggest that the mature tryptase readily dissociates from serglycin proteoglycans when the protease/proteoglycan macromolecular complex is exocytosed into a pH 7.0 environment because the glycosaminoglycan-binding domain on the surface of mMCP-7 consists of a cluster of His residues rather than Lys or Arg residues, as found in mMCP-6 and all mast cell chymases. Although not intending to be limited to a particular mechanism of action, we believe that the prolonged retention of exocytosed mMCP-6 in the extracellular matrix around activated tissue mast cells is associated with a local activity for this tryptase, whereas the rapid dissipation of mMCP-7 from tissues and its poor ability to be inactivated by circulating protease inhibitors suggests that this distinct, but homologous, tryptase cleaves proteins at more distal sites. The present invention is based upon the discovery that the physiological substrate for mMCP-7 is fibrinogen and that this protease also is capable of selectively cleaving human fibrinogen.

The sequences of the mMCP-7 gene and cDNA (from mouse) are presented as SEQ ID NOS. 1, 2 and 3 (GenBank accession nos. for the mMCP-7 gene- cDNA and genomic DNA- and deduced protein are L00653 and L00654). The deduced amino acid sequence of this gene's "mature " (enzymatically active) protein product is encoded by nucleotides 111–845 of SEQ ID NO. 1, or amino acids 28–273 of SEQ ID NO. 3. The nucleic acid and deduced amino acid sequences of the rat, gerbil, and dog homologs of the mMCP-7 gene are presented as SEQ ID NOS. 4–10, and the predicted amino acid sequences for the "mature" protein product for the rat, gerbil, and dog homologs are: the protein encoded by nucleotides 83–847 of SEQ ID NO. 4, or amino acids 19–274 of SEQ ID NO. 5, or amino acids 18–273 of SEQ ID NO. 6 for the rat homolog; the protein encoded by nucleotides 273–1007 of SEQ ID NO. 7, or amino acids 25–270 of SEQ ID NO. 8 for the gerbil homolog; and the protein encoded by nucleotides 104–838 of SEQ ID NO. 9, or amino acids 30–269 of SEQ ID NO. 10 for the dog homolog. Searches of GenBank for similar related proteins show that the mMCP-7 shares some limited, localized homology and sequence motifs to known proteins with serine protease activity in the trypsin-like serine protease family. The common structural motif for this family includes the conserved N-terminus and charge-relay amino acids. Some of the particular structural features of the mMCP-7 tryptase that are known in the art are summarized below.

The structural features of mMCP-7 which indicate that it is a serine protease possessing tryptic specificity are described in the McNeil (Proc. Natl. Acad. Sci. USA 1992; 89:11174–11178), Matsumato et al. (J. Biol. Chem. 1995; 270:19524–19531) and Ghildyal et al. (J. Exp. Med. 1996; 184:1061–1073) references. A comparison of their amino acid sequences revealed that pancreatic trypsin has 223 amino acids, whereas mMCP-7 has 245 amino acids. While 7 insertions and 2 deletions must be placed in mMCP-7 to properly align it with pancreatic trypsin, most of these changes correspond to the loops on the surface that modify and/or restrict the substrate specificity of the enzyme. Based upon the structure of its gene and cDNA, mMCP-7 is translated as a 30–32 kDa zymogen that has a 18-residue hydrophobic signal peptide followed by a 10-amino acid activation pro-peptide. The pro-peptide ends in the sequence Arg-Glu-Gly, which is similar to the Arg-Val-Gly sequence found in the zymogen forms of mMCP-6 and human tryptases I, II/β, and III. Like pancreatic trypsin and other mast cell tryptases, the N-terminus of the mature form of mMCP-7 is Ile-Val-Gly-Gly (SEQ ID NO. 25). The three-dimensional model of mature mMCP-7 suggests that this protease has a trypsin-like fold including two domains with the active site located in the cleft at the interface between the domains. The backbone structure of the mMCP-7 model is virtually indistinguishable from that of pancreatic trypsin. Like all other serine proteases, mMCP-7 has the His/Asp/Ser charge-relay amino acids. An Asp residue that is critical for general tryptic-like activity also resides at the base of the substrate-binding pocket of mMCP-7. Recombinant mMCP-7 readily cleaves the trypsin-susceptible substrate tosyl-Gly-Pro-Lys-p-nitroanilide.

The compositions of the invention include the following preferred tryptase-7 proteins: mature mouse mMCP-7 is encoded by nucleotides 11 1–845 of SEQ ID NO. 1, or amino acids 28–273 of SEQ ID NO. 3, the rat homolog of mature mMCP-7 encoded by nucleotides 83–847 of SEQ ID NO. 4, or amino acids 19–274 of SEQ ID NO. 5, or amino acids 18–273 of SEQ ID NO. 6, the gerbil homolog of mature mMCP-7 encoded by nucleotides 273- 1007 of SEQ ID NO. 7, or amino acids 25–270 of SEQ ID NO. 8, the dog homolog of mature mMCP-7 encoded by nucleotides 104–838 of SEQ ID NO. 9, or amino acids 30–269 of SEQ ID NO. 10, alleles of the foregoing proteases, and the above-described chimeric tryptase-7 proteins that combine portions of a human tryptase (excluding the active site region) with an active site region of the foregoing non-human tryptases. The preferred tryptase-7 nucleic acids of the invention are nucleic acids which encode the foregoing tryptase-7 proteins.

In the preferred embodiments, recombinant mMCP-7 has a specific activity that is at least 10-fold greater than that reported for a tryptase purified from human lung. Even in the presence of serum, 1 µg of recombinant mMCP-7 degrades 10 µg of fibrinogen in 15 min or less. In contrast to most known serine proteases, the tryptase-7 molecules of the invention are not readily inhibited by protease inhibitors that are present in murine or human blood. Moreover, the tryptases of the invention do not require a negatively charge glycosaminoglycan (e.g., heparin) for enzymatic activity. In addition, SDS-PAGE/immunoblot analysis has revealed that plasma mMCP-7 is about 32 kDa in its monomeric form, is not covalently bound to a protease inhibitor and appears to be present as a tetramer with a molecular weight of approximately 150 kDa. Thus, mMCP-7 may be sterically resistant to inactivation by endogenous protease inhibitors because it circulates in the plasma as a multimeric complex rather than as a monomer.

Monomeric mMCP-7 possesses some unique structural features that may hinder its covalent entrapment by protease inhibitors. For example, the lower preponderance of Lys residues on the surface of mMCP-7, coupled with its high degree of glycosylation, may prevent the formation of covalent bonds with the reactive γ-Glu residues of α-macroglobulins.

Homology modeling and electrostatic potential calculations of the mature mMCP-7 and site-directed mutagenesis analysis of recombinant pro-mMCP-7 have revealed that mMCP-7 has a His-rich region on its surface (described in Ghildyal et al., J. Exp. Med., 1996, 184: 1–13). This His-rich region appears to enable mMCP-7 to interact with serglycin proteoglycans inside the mast cell granule which possesses a pH of about pH 5.5. However, in extracellular spaces at pH ≧7.0, the His residues are neutral in charge, thereby permitting mMCP-7 to dissociate from the serglycin proteoglycan and diffuse away from the exocytosed granule core. In contrast, mMCP-6 retains a high surface charge of positively charged Arg or Lys residues on its surface and remains positively charged at pH>7.0, thereby preventing the dissociation of mMCP-6 from the exocytosed macromolecular complex.

Preferably, the tryptase-7 is a murine tryptase-7 or the above-described chimeric tryptase-7 that combines a human tryptase sequence with the active site region of mMCP-7 or a homology of mMCP-7. More preferably, the tryptase-7 is the murine tryptase-7 that is encoded by an isolated nucleic acid selected from the group consisting of: (a) a nucleic acid molecule having the sequence of SEQ ID NO. 1 or 2 (the cDNA or genomic DNA of mMCP-7); (b) alleles of the foregoing nucleic acid molecule; and ( c) nucleic acid molecules that differ from the nucleic acid molecules of (a) and (b) due to the degeneracy of the genetic code. In the preferred embodiments, the murine tryptase-7 is encoded by the isolated nucleic acid consisting essentially of SEQ ID NO. 1. The invention further embraces tryptase-7 proteins that include one, two, or three conservative amino acid substitutions in the active site of the above-noted tryptase-7 proteins, as well as tryptase-7 proteins in which up to 28 amino acids are cleaved from the C-terminal portion of protein. Preferably, the amino acids are cleaved only from the C-terminal portion of the protein. For example, mature mMCP-7 consists of 245 amino acids. Based on studies of other serine proteases, nearly all of these amino acids are needed for the enzyme to exhibit maximal proteolytic activity. However, Benfy and coworkers have reported that the two amino acid residues at the C-terminus are not essential for activity of a rat mast cell chymase (J. Biol. Chem. 1987, 262:5377–5384).

Smaller unique fragments also may be useful for blocking receptor-mediated clearance of mMCP-7 (or other tryptase-7 protein of the invention) from the circulation to prolong the half-life of the active enzyme in vivo. Preferably, the unique fragment codes for a protein that selectively cleaves fibrinogen and/or blocks receptor-mediated clearance. The selection of the unique tryptase-7 fragments is based upon in vitro and in vivo assays that demonstrate the ability of the enzyme to selectively cleave fibrinogen and/or block binding of a mature tryptase (e.g. mMCP-7) to its receptor. These assays are predictive of the ability of the tryptase-7 molecules of the invention to selectively cleave fibrinogen and/or block receptor-binding in humans. In particular, the Example describes a high throughput, spectrophotometric assay that is useful for detecting tryptase-7 catalyzed fibrinogen cleavage activity by determining the ability of a putative tryptase-7 protein to selectively cleave a synthetic peptide substrate. This in vitro assay is predictive of an in vivo fibrinogen cleavage activity.

The tryptase-7 proteins of the invention also embrace the homologs of mMCP-7 of other species, in particular, the homologs that have been identified in rat, gerbil and dog. Thus according to one aspect of the invention, the tryptase-7 proteins embrace an enzyme that is encoded by an isolated nucleic acid selected from the group consisting of: (1) a nucleic acid molecule having the sequence of SEQ ID NOS. 4, 7 and 9 (the sequence nos. for rat, gerbil, dog (cDNAs) homologs of mature mMCP-7); (b) alleles of the rat, gerbil or dog homologs; and (c) nucleic acid molecules that differ from the nucleic acid molecules of (a) and (b) in codon sequence due to the degeneracy of the genetic code. Preferably, the rat, gerbil and dog tryptase-7 is encoded by an isolated nucleic acid consisting essentially of SEQ ID NOS. 4, 7 and 9, respectively (the nucleic acid sequences encoding the rat, gerbil, dog homologs of mMCP-7). The rat, gerbil and dog tryptase-7 proteins also embrace proteins which include the conservative amino acid substitutions and internal insertions/ C-terminal deletions as described above in reference to the murine tryptase-7 proteins. The invention also embraces a tryptase-7 protein that is encoded by an isolated nucleic acid consisting essentially of a unique fragment of the above-described mature tryptase-7 proteins, provided that the unique fragment codes for a tryptase-7 that selectively cleaves fibrinogen, preferably, human fibrinogen, and/or blocks binding of a mature tryptase-7 (e.g., mMCP-7) to its receptor. Thus, the invention provides tryptase-7 proteins, genes encoding those proteins, functional modifications and variants of the foregoing useful unique fragments of the foregoing, as well as therapeutics and diagnostics containing the foregoing tryptase-7 molecules. Tryptase-7 enzymatic activity can be assayed in vitro and/or in vivo. An exemplary spectrophotometric in vitro assay for determining the ability of a tryptase-7 molecule to cleave a synthetic peptide substrate is provided in the Example. This assay is predictive of the ability of the tryptase-7 protein to selectively cleave fibrinogen in vitro and in vivo.

In an alternative embodiment, the tryptase-7 is a "humanized tryptase-7" that also selectively cleaves fibrinogen so that it can be administered chronically (or often). As noted above, mMCP-7 appears to be different from all cloned human tryptases. However, in view of the substantial amino acid sequence homology of the backbones of mMCP-7 and the human tryptases and the discovery of the physiological substrate for mMCP-7, we believe that a chimeric tryptase-7 can be made, for example, by altering a human mast cell tryptase (e.g. tryptase II/β) so that it exhibits the substrate specificity of mMCP-7. As used herein, a "humanized tryptase-7" refers to a recombinant enzyme that selectively cleaves fibrinogen and that consists essentially of: (1) a non-catalytic amino acid sequence that is the amino acid sequence (excepting the active site region sequence) of a human tryptase that does not cleave fibrinogen and (2) an active site region possessing the amino acid sequence of mMCP-7, homologs of mMCP-7 in other species (e.g., rat, gerbil or dog), or alleles of the foregoing. The particular amino acid sequences that are contributed by the human and mouse (or other fibrinogen-cleaving tryptase) are described in detail below.

The enzymatic specificity of each serine protease is defined by a series of loops consisting of 4 to 14 amino acids that extend into the substrate-binding cleft. (See, e.g., Perona and Craik, "Structural basis of substrate specificity in the serine proteases", Protein Sci. 1995; 4:2337–360, for a general review of serine protease substrate specificity.) The crystallographic structure of a mast cell tryptase has not been determined. Nevertheless, based on a comparison of the crystallographic structure of homologous pancreatic trypsin, it has been predicted that seven loops consisting of ~60 amino acids form the substrate-binding cleft of each mast cell tryptase. These loops consist of residues 19 to 29, 43 to 48, 83 to 89, 140 to 143, 164 to 176, 187 to 195, and 211 to 218 of mMCP-7 and human tryptase II/β. To change the substrate specificity of human mast cell tryptase II/β to that of mMCP-7, one would have to change only 13 of the 245 residues in the human enzyme. Residues 20 to 23 in the human tryptase would have to be 30 changed to the sequence Ala-Asn-Asp-Thr. Other changes would be $Thr^{85}$ to Ile. $Ala^{86}$ to Val, $Ile^{88}$ to Asp, $Leu^{164}$ to Lys; $Ala^{166}$ to Leu; $Try^{167}$ to Ile, $Asp^{171}$ to Asn, $Arg^{173}$ to His, and $Arg^{187}$ to His.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which desirably influence tryptase-7 activity. When it is desired to decrease tryptase-7 activity, then any amount which results in inhibition of tryptase-7 activity is regarded as a therapeutically effective amount. When it is desired to increase tryptase-7 activity, then any amount which results in enhancement of tryptase-7 activity is regarded as a therapeutically effective amount. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days. It is preferred that the selection of the administered dose of tryptase-7 be based, at least in part, on the circulating level of fibrinogen in the patient or animal. In general, it is preferred that the dose of tryptase-7 be selected to be 10 to 100 fold lower than the circulating level of fibrinogen. In view of the tight regulation of all enzymatic systems, an over-abundance or over-production of mMCP-7 may be deleterious in certain situations. For example, in mastocytosis patients or patients undergoing systemic anaphylaxis, the level of fibrinogen can decrease to a dangerously low level as found in the blood of the V3 mastocytosis mouse model. Moreover, the proteolytic fragments of fibrinogen themselves also may exhibit potent biologic activity. Accordingly, the tryptase-7 proteins described herein also can be used to screen varied combinatorial libraries to isolate inhibitors that selectively inhibit tryptase-7 enzymatic activity. Such screening methods are described below.

According to one approach, mMCP-7 (or an equivalent tryptase-7 protein of the invention) is immobilized in a gel or support medium and then incubated with a phage display peptide library to select those phage that bind to the recombinant mMCP-7 with high affinity and which also inhibit its ability to cleave fibrinogen (See the Example). After the pH or ionic strength is altered, the liberated phage is allowed to bind to an anti-FLAG Ig column such as the column described in the Example. Enterokinase-activated mMCP-7 is added, the column is sealed, incubated at 37° C., and then washed extensively to remove those phage that are highly susceptible to cleavage by recombinant mMCP-7. In theory, those phage that remain associated with the column possess protease-resistant domains even though the previous selection process demonstrated that they exhibit high affinity binding to mMCP-7. Some of these phage should possess peptide sequences in their altered pIII surface proteins that are active-site inhibitors. The pH or ionic strength of the elution buffer then is altered to recover this select group of phase. DNA analysis of the sequence that encodes the altered pIII protein on the surface of each cloned phage provides insight as to which amino acid sequences are candidate protease inhibitors.

In a second approach analogous to that described by Fang and coworkers (Biochem. Biophys. Res. Commun. 1996; 220:53–56), those phage that bind to mMCP-7 with high affinity are isolated. Thereafter, these clones are examined to identify those which inhibit the ability of recombinant mMCP-7 (or other tryptase-7 protein of the invention) to degrade its susceptible substrate tosyl-Gly-Pro-Lys-p-nitroanilide. Those phage clones that inhibit the enzymatic activity are further characterized.

In a third approach analogous to that described by Willard and coworkers (Eur. J. Med. Chem. 1996; 31:87–98), commercially-prepared libraries consisting of varied combinations of synthetic peptides linked to an inert polymer are used to isolate those peptides that inhibit the enzymatic activity of recombinant mMCP-7 (or other tryptase-7 protein of the invention) to a statistically significant extent. Such commercially-prepared libraries are available from Selectide Corporation, Tucson, Ariz.

The therapeutics of the invention can be administered by any conventional route, including injection or by gradual infusion over time. The administration may, for example, be oral, intravenous, intraperitoneal, intramuscular, intra cavity, subcutaneous, or transdermal. Generally, such systems should utilize components which will not significantly impair the biological properties of the proteins, (see, for example, *Remington's Pharmaceutical Sciences,* 18th edition, 1990; incorporated by reference). Those of skill in the art can readily determine the various parameters and conditions for producing such pharmaceutical preparations without resort to undue experimentation. When using the tryptase-7 protein preparations of the invention, intravenous administration is preferred.

An alternative, preferred route of administration of the therapeutics of the invention is by pulmonary aerosol. Techniques for preparing aerosol delivery systems containing proteins are well known to those of skill in the art. Generally, such systems utilize components which will not significantly impair the biological properties of the proteins. (See, e.g., Sciarra and Cutie, "Aerosols," in Remington's Pharmaceutical Sciences, 18th edition, 1990, pp 1694–1712.) Those of skill in the art can readily determine the various parameters and conditions for producing protein aerosols without resort to undue experimentation.

Preparations for parenteral administration include sterile aqueous or non-aqueous solutions, suspensions, and emulsions. Although mMCP-7 is active in aqueous solutions, a non-aqueous solution might prolong its retention in tissue sites. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, or lactated Ringer's. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The tryptase-7 proteins of the invention can be administered in accordance with known methods for administering thrombolytic agents to a patient. Exemplary pharmaceutically acceptable carriers and modes of administration for delivering a protein product (e.g., a thrombolytic agent) to treat a condition that is mediated by a clinically undesirable fibrin clot in a subject are described in at least the following United States patents: U.S. Pat. No. 5,372,812, issued to Reed et al.; U.S. Pat. No. 5,385,732, issued to Anderson et al.; U.S. Pat. No. 5,239,058, issued to Vlasuk et al.; and U.S. Pat. No. 5,405,771, issued to Anderson et al. In general, the concentration range of the tryptase-7 protein which defines a therapeutically effective amount of the active agent is approximately the same concentration range of a clinically known thrombolytic agent (e.g., t-PA, streptokinase, urokinase) which defines a therapeutically effective amount of these agents.

As would be apparent to those of ordinary skill in the art, the tryptase-7 proteins and nucleic acids of the invention alternatively can be delivered using controlled release drug delivery systems. Preferably, such systems are biodegradable and bioerodible. More preferably the pH is acidic within all or part of the delivery system to mimic the pH of the mast cell granule (pH ~5.5) and, thereby, minimize autolysis. In the most preferred embodiments, the tryptase-7 protein is bound to serglycin proteoglycan in the controlled release delivery system.

In one particular embodiment, the preferred pharmaceutical composition is contained in an implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/03307 describes a biocompatible, preferably biodegradable polymeric matrix for containing an exogenous gene under the control of an appropriate promotor. The polymeric matrix is used to achieve sustained release of the exogenous gene in the patient. In accordance with the instant invention, the tryptase-7 compositions described herein are encapsulated or dispersed within the biocompatible, preferably biodegradable polymeric matrix disclosed in PCT/US/03307. The polymeric matrix preferably is in the form of a micro particle such as a micro sphere (wherein the tryptase-7 composition is dispersed throughout a solid polymeric matrix) or a microcapsule (wherein the tryptase-7 composition is stored in the core of a polymeric shell). Other forms of the polymeric matrix for containing the tryptase-7 composition include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a mucosal or other surface. The matrix composition also can be selected not to degrade, but rather, to release by diffusion over an extended period of time.

Both non-biodegradable and biodegradable polymeric matrices can be used to deliver the tryptase-7 compositions of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the tryptase-7 compositions of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthlate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in *Macromolecules,* 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described tryptases for use as a medicament, methods for preparing the medicament and methods for the sustained release of the medicament in vivo.

The invention includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also includes homologs and alleles of the mMCP-7 protein. Homologs and alleles of the tryptase-7 genes of the invention can be identified by conventional techniques. Thus, an aspect of the invention is those nucleic acid sequences which code for tryptase-7 proteins and which hybridize to a nucleic acid molecule consisting of SEQ ID NO. 1 or 2 under stringent conditions. The term "stringent conditions" as used herein refers to parameters with which the art is familiar. More specifically, "stringent conditions" as used herein, refers to hybridization at 65° C. in hybridization buffer (3.5×SSC, 0.02% Ficoll, 0.02% Polyvinyl pyrolidone, 0.02% bovine serum albumin, 2.5 mM $NaH_2PO_4$ (pH 7), 0.5% SDS 2mM EDTA). SSC is 0.15M sodium chloride/0.15M sodium citrate, pH 7; SDS is sodium dodecyl sulphate and EDTA is ethylenediaminetetracetic acid. After hybridization, the membrane upon which the DNA is transferred is washed at 2×SSC at room temperature and then at 0.1×SSC/0.1×SDS at 65° C.

There are other conditions, reagents, and so forth which can be used, which result in a similar degree of stringency. The skilled artisan will be familiar with such conditions, and accordingly, such conditions are not provided herein. It will be understood, however, that the skilled artisan will be able to manipulate the conditions in a manner to permit the clear identification of homologs and alleles of the tryptase-7 proteins of the invention. The skilled artisan also is familiar with methodology for screening cells and libraries for expression of such molecules which then are isolated in accordance with the methods provided herein, and sequenced.

In general, homologs and alleles typically will share at least about 70 percent nucleotide identity and/or at least 70 percent amino acid identity to SEQ ID NO. 1 or 2. In some instances, homologs and alleles of the tryptase-7 will share at least 80 percent nucleotide identity and/or at least 80 percent amino acid identity and in still other instances, will share at least 90 percent nucleotide identity and/or at least 90 percent amino acid identity to the tryptase-7 molecules disclosed herein. Watson-Crick complements of the foregoing nucleic acids also are embraced by the present invention. In screening for the tryptase-7 family members in other species, a southern block may be performed using the foregoing conditions, together with a radioactive probe. After washing the membrane to which the DNA is finally transferred, the membrane can be placed against X-ray film to detect the radioactive signal.

The invention also provides isolated unique fragments of SEQ ID NO. 1 or 2 (the mMCP-7 nucleic acid), SEQ ID NOS. 4, 7 and 9 (the rat, gerbil and dog nucleic acid homologs of mMCP-7), or complements of these sequences. A unique fragment is one that is a 'signature' for the larger nucleic acid. It, for example, is long enough to assure that its precise sequence is not found in molecules outside of the above-described tryptase-7 protein family. Unique fragments can be used as probes in Southern blot assays to identify family members or can be used in amplification assays such as those employing PCR. As known to those skilled in the art, large probes such as 200 base pair (bp) or more are preferred for certain uses such as Southern blots, while smaller fragments will be preferred for uses such as PCR. Unique fragments also can be used to produce fusion proteins for generating antibodies or for generating immunoassay components. Likewise, unique fragments can be employed to produce fragments of the tryptase-7 protein such as only the extracellular portion, useful, for example, in immunoassays or as a competitive inhibitor of the substrate of the tryptase-7 protein in therapeutic or diagnostic applications. Unique fragments further can be used as antisense molecules to inhibit the expression of the tryptase-7 proteins of the invention, particularly for therapeutic purposes or animal models of disease such as described in greater detail below.

As will be recognized by those skilled in the art, the size of the unique fragment will depend upon its conservancy in the genetic code. Thus, some regions of SEQ ID NO. 1 and their complements will require longer segments to be unique while others will require only short segments, typically between 12 and 32 bp (e.g. 12, 13, 14, 15, 16, 17, 18, 19, 20, 21, 22, 23, 24 25, 26, 27, 28, 29, 30, 31 and 32 bases long). Virtually any segment of SEQ ID NO. 1 or 2, or their complements, that is 18 or more nucleotides in length will be unique. Those skilled in the art are well versed in methods for selecting such sequences, typically on the basis of the ability of the unique fragment to selectively distinguish the sequence of interest from non-family members. A comparison of the sequence of the fragment to those on known data bases typically is all that is necessary, although in vitro confirmatory hybridization and sequencing analysis may be performed.

The invention further embraces antisense oligonucleotides that selectively bind to a nucleic acid molecule encoding a tryptase-7, to decrease tryptase-7 activity in certain species. This is desirable in virtually any medical condition where a reduction in tryptase-7 activity is desirable. Alternatively, or additionally, the antisense molecules of the invention can be used to prepare knockout animals (knockout rats or baboons) to establish the further physiological significance of tryptase-7. Antisense oligonucleotides are useful, for example, for preparing an animal model of conditions that are characterized by excessive fibrinogen cleavage and/or a reduced ability to form fibrin clots in vivo. Such animal models can be used in screening assays for identifying therapeutic drugs which prevent or reduce excessive fibrinogen cleavage.

As used herein, the term "antisense oligonucleotide" or "antisense" describes an oligonucleotide which hybridizes under physiological conditions to DNA comprising a particular gene or to an RNA transcript of that gene and, thereby, inhibits the transcription of that gene and/or the translation of the mRNA. The antisense molecules are designed so as to hybridize with the target gene or target gene product and thereby, interfere with transcription or translation of the target mammalian cell gene. Those skilled in the art will recognize that the exact length of the antisense oligonucleotide and its degree of complementarily with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 and, more preferably, at least 15 consecutive bases which are complementary to the target. Most preferably, the antisense oligonucleotides comprise a complementary sequence of 20–30 bases. Reduction in transcription or translation of the nucleic acid molecule is desirable in preparing an animal model for further defining the role played by the mammalian target cell nucleic acid in modulating an adverse medical condition.

The invention also contemplates expressing the tryptase-7 nucleic acids in vitro and in vivo. The tryptase-7 nucleic acid, in one embodiment, is operably linked to a gene expression sequence which directs the expression of the tryptase-7 nucleic acid within a eukaryotic or insect cell. The "gene expression sequence" is any regulatory nucleotide sequence, such as a promoter sequence or promoter-enhancer combination, which facilitates the efficient transcription and translation of the tryptase-7 nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Preferably, the tryptase-7 nucleic acid of the invention is linked to a gene expression sequence which permits expression of the tryptase-7 nucleic acid in a mast cell. More preferably, the gene expression sequence permits expression of the tryptase-7 nucleic acid in a human mast cell. A sequence which permits expression of the tryptase-7 nucleic acid in a human mast cell is one which is selectively active in mast cells and thereby causes the expression of the tryptase-7 nucleic acid in these cells. mMCP-7 is expressed in the population of mast cells that also express carboxypeptidase A (mMC-CPA). Thus, the promoter of the mMC-CPA gene can be used to express the tryptase-7 nucleic acid in human mast cells (Zon et al., J. Biol. Chem. 1991, 266:22948–22953). Those of ordinary skill in the art will be able to easily identify alternative promoters that are capable of expressing a tryptase-7 nucleic acid in a mast cell.

The tryptase-7 nucleic acid sequence and the gene expression sequence are said to be "operably linked" when they are covalently linked in such a way as to place the transcription and/or translation of the tryptase-7 coding sequence under the influence or control of the gene expression sequence. If it is desired that the tryptase-7 sequence be translated into a functional protein, two DNA sequences are said to be operably linked if induction of a promoter in the 5' flanking region of the gene expression sequence results in the transcription of the tryptase-7 sequence and if the nature of the linkage between the two DNA sequences does not (1) result in the introduction of a frame-shift mutation, (2) interfere with the ability of the promoter region to direct the transcription of the tryptase-7 sequence, or (3) interfere with the ability of the corresponding RNA transcript to be translated into a protein. Thus, a gene expression sequence would be operably linked to a tryptase-7 nucleic acid sequence if the gene expression sequence were capable of effecting transcription of that tryptase-7 nucleic acid sequence such that the resulting transcript might be translated into the desired protein or polypeptide.

The tryptase-7 nucleic acid of the invention can be delivered to the mast cell alone or in association with a vector. In its broadest sense, a "vector" is any vehicle capable of facilitating: (1) delivery of a tryptase-7 molecule to a target cell or (2) uptake of a tryptase-7 molecule by a target cell. Preferably, the vectors transport the tryptase-7 molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a tryptase-7 nucleic acid or a tryptase-7 protein) can be selectively delivered to a mast cell in vivo.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

Thus, cells (e.g., mast cells, their progenitor cells, and other relevant hematopoietic cells, such as cytotoxic lymphocytes and neutrophils that have the machinery to properly process granule proteases) which lack a functional tryptase-7 protein are provided with a non-defective nucleic acid encoding a tryptase-7 protein. In particular, such gene therapy is appropriate for hereditary conditions attributable to absent or defective tryptase-7 protein genes. For example, mast cells can be obtained in vitro from bone marrow stem cells isolated from a subject who is a candidate for such gene therapy, e.g., mast cells can be derived by culturing isolated bone marrow cells from the subject in the presence of c-kit ligand. Candidates can be identified by screening for abnormal tryptase-7 function that results from an absent or defective tryptase-7 protein. Then, such cells can be genetically engineered ex vivo with DNA (RNA) encoding a normal tryptase-7 protein. The genetically engineered cells then are returned to the patient.

According to one aspect of the invention, the tryptase-7 proteins and nucleic acids of the invention are useful in a method for treating a blood clot in a subject. The method involves administering to the subject in need of such treatment, an isolated nucleic acid molecule that codes for a tryptase-7 or an expression product thereof. The nucleic acid molecule or expression product thereof is administered to the subject in a therapeutically effective amount to decrease fibrinogen activity in the subject. The tryptase nucleic acid and/or encoded protein can be administered alone or together with other thrombolytic agents to treat a blood clot in a subject. As used herein, the term "thrombolytic agents" refers to any agent that is capable of either dissolving a fibrin/platelet clot or inhibiting the formation of such a clot, provided that inhibiting the formation of such a clot does not involve fibrinogen cleavage. Exemplary thrombolytic agents include streptokinase, prourokinase, urokinase, and tissue-type plasminogen activator (t-PA). Blood clots which may be treated in accordance with the methods of the invention include, but are not limited to, those associated with pulmonary thromboembolism, deep vein thrombosis, cerebral embolism, renal vein and peripheral arterial thrombosis, and the like. Thus, the compositions and methods of the invention are useful for reducing fibrin/platelet clot formation in vivo and, thereby, preventing the reocclusion of an affected artery following primary thrombolytic therapy.

No human homolog of mMCP-7 has been isolated so far. Thus, for human therapeutic applications, the preferred tryptase-7 proteins of the invention are chimeric proteins that contain (a) the amino acid sequence of a known human tryptase for all but the active site region of the protein and (b) the amino acids that comprise the substrate binding pocket of mMCP-7 or of its homologs from, e.g., mouse, rat, gerbil, or dog). Four human tryptase cDNAs (designated tryptase α, I, β/II, and III) reportedly have been isolated by two groups of investigators using two different cDNA libraries (Miller et al., J. Clin. Invest. 1989; 84:1188–1195; Miller et al., J. Clin. Invest. 1990; 86:64–870; Vanderslice et al., Proc. Natl. Acad. Sci. USA 1990; 87:3811–3815). Miller's cDNA library was prepared using RNA isolated from a human lung preparation that contained only 30% mast cells, whereas Vanderslice's cDNA library was prepared using RNA isolated from human skin that contained only 1% mast cells. Despite the presence of so many contaminating cells in the starting preparations and despite the fact that mature mast cells are mRNA deficient (Benfey et al., J. Biol. Chem. 1987; 262:5377–5384; Tantravahi et al., Proc. Natl. Acad. Sci. USA 1986; 83:9207–9210), Miller and Vanderslice report that all of their isolated tryptase cDNAs originated from the small number of MC in the tissue preparations. Since the isolated human cDNAs encode enzymes that are >90% identical in their overall amino acid sequences, since humans are not inbred, and since the genes and the region of the chromosome where the tryptase genes reside have not yet been sequenced, the actual number of human mast cell tryptase genes is still unknown. There may be one gene in the human possessing multiple alleles or there may be four or more tryptase genes, some of which are nearly identical.

The enzymatic specificity of each serine protease is defined by a series of loops consisting of 4 to 14 amino acids that extend into the substrate-binding cleft. The crystallographic structure of a mast cell tryptase has not been determined. Nevertheless, based on a comparison of the crystallographic structure of homologous pancreatic trypsin, it is predicted that seven loops consisting of ~60 amino acids form the substrate-binding cleft of each mast cell tryptase. The amino acid residues in 6 of the 7 putative loops are 100% identical in human mast cell tryptases I, II/β, and III. This finding is consistent with the other data which suggested that these human tryptases represent varied alleles of the same gene. The substrate specificity of recombinant mMCP-7 is very different from that of recombinant mMCP-6. Because mMCP-7 has different amino sequences in 4 of the 7 loops, it is likely that this mouse tryptase also has a substrate specificity that is very different from human mast cell tryptases α, I, II/β, and III. A comparison of the residues 164 to 176 that form the largest and most variable loop that likely resides in the substrate-binding cleft is shown below. Note that many of the changes should alter the nature of this loop considerably. For example, residue 164 is a hydrophobic Leu (L) in all human tryptases but is a basically charged Lys (K) in mMCP-7.

Mast Cell Tryptase Amino Acid Sequences of Loop 3*

| | | |
|---|---|---|
| h tryptase I | L–G–A–Y–T–G D D V R I V R D | (SEQ ID NO. 26) |
| h tryptase II/β | L–G–A–Y–T–G–D–D–V–R–I–V–R–D | (SEQ ID NO. 26) |
| h tryptase III | L–G–A–Y–T–G–D–D–V–R–I–V–R–D | (SEQ ID NO. 26) |
| h tryptase α | L–G–A–Y–T–G–D–D–V–R–I–*I*–R–D | (SEQ ID NO. 27) |
| mMCP-6 | T–G–L–Y–T–G–D–D–F–P–I–V–H–D | (SEQ ID NO. 28) |
| mMCP-7 | K–G–L–I–T–G–D–N–V–H–I–V–R–D | (SEQ ID NO. 29) |

*The single letter code for each amino acid is used in the above comparisons. Residues that are *italicized* and in bold indicate amino acids that are not found in human mast cell tryptase I, II/β and III.

In view of the foregoing, we believe that "humanized" tryptase-7 proteins can be designed that selectively cleave fibrinogen in vitro and in vivo. Such humanized tryptase-7 proteins preferably contain at least 90% (more preferably ≧95%) of the amino acid sequence of a human mast cell tryptase and are particularly useful in applications that require repetitive administration of the tryptase-7 to a human subject. The embodiments described below illustrate such humanized tryptase-7 proteins.

According to a first embodiment, the entire loop 3 of a human mast cell tryptase is replaced by the corresponding loop 3 of mMCP-7 or loop 3 of an mMCP-7 homolog from another species. In a particularly preferred embodiment, the chimeric tryptase-7 has the amino acid sequence of a human mast cell tryptase (e.g., α, I, II/β or III) with the exception that the loop 3 of the human mast cell tryptase is replaced with loop 3 of mMCP-7. Alternatively, the chimeric tryptase-7 has the amino acid sequence of a human mast cell tryptase with the exception that the loop 3 of the human mast cell tryptase is replaced with the loop 3 of the rat, gerbil or dog homolog of mMCP-7. Such chimeric proteins can be produced in accordance with routine recombinant procedures known to one of ordinary skill in the art.

According to a second embodiment, from one to six (preferably, from 1–4) amino acids in the loop 3 of a human mast cell tryptase are replaced by the corresponding amino acid in the loop 3 of mMCP-7 or in the loop 3 of an mMCP-7 homolog. In a particularly preferred embodiment, the chimeric tryptase-7 has the amino acid sequence of a human mast cell tryptase with the exception that residue 164 is a basically charged amino acid (preferably Lys (K)) instead of Leu (L). Further, this chimeric tryptase-7 may include up to four additional amino acid substitutions of mMCP-7 loop 3 specific amino acid residues for the corresponding amino acid residues of the human mast cell protease (see table, above).

In addition to the above-noted active site region differences between mMCP-7 and the human mast cell tryptases, mMCP-7 also differs significantly from other mouse and human tryptases in the inclusion of a unique 5' untranslated region in its mRNA. Because the gene that encodes mMCP-7 underwent a point mutation at the region of the gene that corresponds to the exon 1/intron 1 splice site of the mMCP-6 gene, the 5' untranslated region (UTR) of mMCP-7 mRNA is unique in its length and sequence (McNeill et al., Proc. Natl. Acad. Sci. USA 1992; 89:11174–11178). The subsequent report that the Mongolian gerbil homolog of mMCP-7 has a similar 5'UTR (Murakumo et al., Biochem. J. 1995; 309:921–926) documents that this property of the mMCP-7 transcript is not unique to the mouse and suggests to us a structural and functional similarity of mMCP-7 and its gerbil homolog.

According to yet another aspect of the invention, compositions and methods for producing a serine protease in active form and in large quantities are provided. The compositions include a nucleic acid (e.g., a DNA) encoding a serine protease comprising a polynuclecotide encoding, from its 5' to 3' direction (N- to C-terminal direction in the encoded protease): (a) a "pre" sequence of a serine protease or other secreted protein; (b) a "pro" peptide sequence of the same or a different serine protease; ( c) an endopeptidase (e.g., enterokinase) cleavage domain; and (d) the mature serine protease with or without the FLAG peptide. Preferably, the pro peptide sequence is the endogenous pro sequence of the zymogen from which the mature serine protein is derived.

The tryptase-7 proteins of the invention are "zymogens" in that the protein is initially synthesized as an inactive precursor possessing: (1) a signal peptide which targets the remaining portion of the protein to be translocated across a membrane and (2) a "pro-peptide" that intervenes between the signal peptide and the mature protein. In general, a hydrophobic signal (or pre) peptide is necessary to express any protein in an insect cell because it faciliates transport of the initially translated protein from the cytosol into the lumen of the endoplasmic reticulum. In the expression construct described in the Example, the endogenous signal peptide of mMCP-7 was used. Nevertheless, the signal peptide of nearly any secretory protein could have been used in place of the endogenous signal peptide to faciliate transport into the lumen of the endoplasmic reticulum. For example, many constructs that have been generated for expressing mammalian proteins in insect cells use the signal peptide of a honey bee protein.

A typical signal or pre sequence consists of about 18 residues and possesses a large number of hydrophobic amino acids (e.g., Leu, Val) that anchor the signal peptide across the membrane lipid bi-layer during transport of the nascent polypeptide. Following initiation, the pre sequence typically is cleaved within the lumen of the endoplasmic reticulum by cellular enzymes known as signal peptidases. The potential cleavage sites of the pre sequence generally follow the rule known as the "(−3, −1) rule". A typical pre sequence includes a small, neutral amino acid residues in positions −1 and −3 and lacks protein residues in this region. The signal peptidase will cleave such a signal peptide between the −1 and +1 amino acids. Thus the portion the DNA encoding the pre sequence is cleaved from the amino terminus of the protein early during the post-translational modification of the protein. In the varied serine proteases, the pre-peptide generally consists of 18 or 19 residues.

The pro-peptide sequences which are useful in accordance with the methods of the invention are the naturally occurring pro-peptide sequences for the serine proteases, preferably for the trypsin-like serine proteases that are isolated from mast cells. In the mast cell tryptase family, the pro-peptide contains 10 residues. A comparison of the human and mouse tryptase pro peptide sequences is shown in the tables, below. The pro-peptide of the mast cell tryptase family is quite different from the 2-residue pro-peptide in the chymase family of serine proteases. The genes that encode the mast cell chymases (mMCP-1, GenBank Nos. X68803 and X62803, Le Trong et al., Biochem. 1989, 28:391–395, Huang et al., Eur. J. Immunol., 1991, 21:1611–1621; mMCP-2 GenBank No. J05177; mMCP-4 GenBank Nos. M55616, M55617, and M57401; and mMCP-5 GenBank Nos. M73759 and M73760; mMCP-8; and mMCP-9) reside on chromosome 14 ("chromosome 14 family of serine proteases") at the same locus that contains the genes that encode cathepsin G, and granzymes B, C, E, and F. The enterokinase expression approach described in the Example has also been used by us to obtain quite a few recombinant mast cell chymases. This was accomplished by changing the endogenous pro-peptide found in mMCP-7 to Glu-Glu which is found in these chymases.

Comparison of the Hydrophobic Signal (or Pre) Peptides of Mouse and Human Mast Cell Tryptases
Tryptase Signal peptides (starting at the Met, translation-initiation codon) mMCP-7

Met-Leu-Lys-Leu-Leu-Leu-Leu-Thr-Leu-Pro-Leu-Leu-Ser-Ser-Leu-Val-His-Ala (SEQ ID NO. 30) mMCP-6

Met-Leu-Lys-Arg-Arg-Leu-Leu-Leu-Leu-Trp-Ala-Leu-Ser-Leu-Leu-Ala-Ser-Leu-Val-Try-Ser (SEQ ID NO. 31) h tryptase α

Met-Leu-Ser-Leu-Leu-Leu-Leu-Ala-Leu-Pro-Val-Leu-Ala-Ser-Arg-Ala-Try-Ala-Ala-Pro (SEQ ID NO. 32) h tryptase I Met-Leu-Asn-Leu-Leu-Leu-Leu-Ala-Leu-Pro-Val-Leu-Ala-Ser-Arg-Ala-Tyr-Ala-Ala-Pro (SEQ ID NO. 33) h tryptase II/β

Met-Leu-Asn-Leu-Leu-Leu-Leu-Ala-Leu-Pro-Val-Leu-Ala-Ser-Arg-Ala-Tyr-Ala-Ala-Pro (SEQ ID NO. 33) tryptase III Met-Leu-Asn-Leu-Leu-Leu-Leu-Ala-Leu-Pro-Val-Leu-Ala-Ser-Arg-Ala-Tyr-Ala-Ala-Pro (SEQ ID NO. 33)

In the case of the varied mast cell proteases, it appears that the pro-peptides are cleaved off in the mast cell's granule after the proteases ionically bind to serglycin proteoglycans. The putative pro-peptides of mMCP-6 and mMCP-7 consist of 10 amino acids each, are 60% identical, begin with an Ala-Pro sequence, and end with a Gly residue (see the tables, above). Thus, the pro-peptides of the mouse tryptases are quite different from the Gly-Glu or Glu-Glu pro-peptides of mouse and human mast cell chymases. The signal and pro-peptides for human tryptase I, II/β, and III reportedly are 100% identical, suggesting that these three tryptases are encoded by different alleles of the same gene. When compared to the other human tryptases, the pro-peptide of human tryptase α is different in 3 out of the 10 residues; 1 residue in the signal peptide is also different.

In the preferred embodiments of the expression cassette, the serine protease is a trypsin-like mast cell serine protease such as the murine tryptase-7, the rat homolog of the murine tryptase-7 ("rat tryptase-7"), the gerbil homolog of the murine tryptase-7 ("gerbil tryptase-7"). the dog homolog of the murine tryptase-7 ("dog tryptase-7"), or alleles of the foregoing proteins. More preferably, the serine protease is mMCP-7 or the above-described humanized tryptase-7 protein.

The mature recombinant serine proteases generated using the expression cassettes include an N-terminal residue that is uncharged or that does not influence the active conformation of the protease and is not essential to the enzymatic activity of the protease. In the preferred embodiments, the serine protease has a N-terminal residue that preferentially is an isoleucine. Exemplary serine proteases which satisfy this criteria include all mast cell serine proteases and, in particular, include the tryptase-7 isolated from murine mast cells and homologs thereof, as well as alleles of the foregoing. In the preferred embodiments, the serine protease is a mast cell protease which is murine tryptase-7 and which has a prepro or pro sequence consisting essentially of the prepro or pro sequence of mMCP-7. In an alternative embodiment, the mast cell protease has a prepro or pro sequence consisting essentially of the prepro or pro sequence of the rat, gerbil or dog homologs of mMCP-7.

The invention also embraces an expression cassette in which the nucleic acid molecule encodes a mature serine protease that contains one, two, or three conservative amino acid substitutions in its active site region. The invention also Comparison of the Pro-peptides of Mouse and Human Mast Cell Tryptases

| Tryptase | Propeptide (and residue number) | |
|---|---|---|
| | -10                   -3    -1    +1 | |
| mMCP-7 | Ala-Pro-Gly-Pro-Ala-Met-Thr-Arg-Glu-Gly----Mature enzyme | (SEQ ID NO. 34) |
| mMCP-6 | Ala-Pro-Arg-Pro-Ala-Asn-Gln-Arg-Val-Gly----Mature enzyme | (SEQ ID NO. 35) |
| htryptase α | Ala-Pro-Val-Gln-Ala-Leu-Gln-Gln-Ala-Gly----Mature enzyme | (SEQ ID NO. 36) |
| htryptase I | Ala-Pro-Gly-Gln-Ala-Leu-Gln-Arg-Val-Gly----Mature enzyme | (SEQ ID NO. 37) |
| htryptase II/β | Ala-Pro-Gly-Gln-Ala-Leu-Gln-Arg-Val-Gly----Mature enzyme | (SEQ ID NO. 37) |
| htryptase III | Ala-Pro-Gly-Gln-Ala-Leu-Gln-Arg-Val-Gly----Mature enzyme | (SEQ ID NO. 37) | embraces the foregoing nucleic acid molecules that encode a serine protease wherein the prepro or pro sequence contains one, two or three conservative amino acid substitutions. As used herein, "conservative amino acid substitution" refers to an amino acid substitution which does not alter the relative charge or size characteristics of the peptide in which the amino acid substitution is made. Conservative substitutions of amino acids include substitutions made amongst amino acids within the following groups: (a) MILV; (b) FYW; (c) KRH; (d) AG; (e) ST; (f) QN; and (g) ED. Serine proteases which include conservative amino acid substitutions retain enzymatic activity.

The cassettes of the invention are useful for expressing a broad spectrum of serine proteases. When the expression cassettes of the invention are used, the serine proteases are produced as "pseudo-zymogens", i.e., a serine protease zymogen that further includes a cleavage domain (e.g., an enterokinase susceptibility domain) positioned between the pro-peptide and the mature protein. Thus, the pseudo-zymogens contain: (1) a signal peptide and (2) a "pseudo-pro-peptide" (i.e., a peptide containing a pro-peptide followed by a cleavage domain).

Exemplary serine proteases that can be produced in accordance with the methods of the invention include: mMCP-7 and mMCP-6. In addition, the expression cassette can be used to obtain recombinant mast cell tryptases from all species. As noted above, the modified expression construct containing the Glu-Glu pro-peptide can be used for expressing any member of the chromosome 14 family of serine proteases (e.g., granzyme B, GenBank Accession No. M28879). The Example illustrates the use of an expression cassette of the invention to prepare large quantities of enzymatically active mMCP-7. The construction of the mMCP-7 cassette is illustrative only and is not intended to limit the invention in any way. As would be appreciated by one of skill in the art, an important feature of the invention is that it provides a generalized nucleic acid construct and procedures that can be used to facilitate recombinant production of any serine protease.

The proteolytic cleavage site must be sufficiently small so that insertion of the cleavage site between the nucleic acids encoding the pro sequence and the mature portion of the serine protease does not adversely affect the folding of the mature protein into a catalytically active enzyme following its release from the pseudo-zymogen. In addition, cleavage of the proteolytic cleavage site preferably results in an isoleucine residue at the N-terminal residue of the mature protease. Selection of cleavage sites which satisfy these criteria can be made by referring to the literature which defines the cleavage site specifically for well known endopeptidase. In general, the proteolytic cleavage sites that are useful in the expression cassettes of the invention include about five amino acids.

An enterokinase susceptibility domain is preferred. As used herein, "enterokinase susceptibility domain" refers to the particular amino acid sequences that are selectively cleaved (enzymatically removed) by an enterokinase (see, e.g., Intl. Appln. No. PCT/US94/00616 having publication no. WO 94/16083 and claiming priority to U.S. Ser. No. 08/005,944 (filed Jan. 15, 1993)). The enterokinase susceptibility domain for the enterokinase selectively cleaves the Lys-Ile peptide bond in the amino acid sequence: Asp-Asp-Asp-Asp-Lys-Ile (SEQ ID NO. 24). As would be immediately apparent to one of ordinary skill in the art, variations of this cleavage sequence which include conservative amino acid substitutions, such as the substitution of a Glu for an Asp, also are selectively cleaved by the enterokinase. Accordingly, as used herein, enterokinase susceptibility domain includes such sequences which contain conservative amino acid substitutions, provided that the peptides containing such substitutions are selectively cleaved by the enterokinase. (See, also, Light et al., Anal. Biochem. 106:199 (1980).

The expression cassette is useful for producing an isolated, enzymatically active serine protease, such as a mast cell serine protease. The resultant serine protease can be expressed at high levels in a host cell such as a SF9 insect cell and can be collected from culture media without the need for lysis of the host cell. The method for producing the serine protease involves the following steps: (1) culturing a host cell which expresses the above-described nucleic acid in a medium under conditions to promote expression and secretion of the serine protease; (2) purifying the inactive zymogen; (3) enzymatically removing the pseudo-propeptide; and (4) collecting the mature serine protease. Optionally, the method further involves the step of activating the serine protease, for example, by increasing the pH from about pH 5.0 to about pH 7.0. In the preferred embodiments, the host cell is an insect cell such as that described in the Example. Other exemplary host cells include yeast, bacteria and mammalian cells such as the RBL-1 cell.

Most transfected mammalian cells are cultured in media containing 5 to 15% fetal calf serum. One of the major advantages of an insect cell expression system is the ability to culture the expressing cells in serum-free media, thereby minimizing the problems inherent to removing large quantities of contaminating proteins. In the Example, approximately 10 to 50% of the proteins found in the insect cell conditioned media were recombinant proteins. Nevertheless, one or two purification steps must be performed to remove the contaminating proteins. To further improve the process for purifying large quantities of enzymatically active serine proteases, a second modified construct was developed and is described herein in the Example. The second construct encodes a pseudo-zymogen form of mMCP-7 and has, in addition, a FLAG peptide attached to its C-terminus. Attachment of the FLAG peptide did not adversely influence the enzymatic activity of recombinant mMCP-6 or mMCP-7 and enabled the purification of a substantially pure preparation (i.e., $\geq 90\%$) of the recombinant tryptase in a single affinity chromatography step using an anti-FLAG Ig column.

In summary, various expression cassettes for obtaining large quantities of enzymatically active proteases are disclosed herein. In addition to the particular mMCP-7 expressing cassette that is described in the Example, modified expression cassettes that are useful for generating other recombinant serine proteases in insect cells are provided. The first modified expression cassette encodes a pseudo-zymogen that has a FLAG peptide at its C-terminus. The second encodes a pseudo-zymogen that has a Glu-Glu pro-peptide instead of the 10 residue pro-peptide of mMCP-7. The third encodes a pseudo-zymogen that has both the Glu-Glu pro-peptide and the FLAG peptide at its C-terminus. As will be apparent to one of ordinary skill in the art, other such modifications can be made without departing from the spirit and scope of the invention.

The invention is based on the discovery that a cleavage domain can be inserted between the prepro or pro sequence and the mature portion of a serine protease without adversely affecting the folding of the protease into an enzymatically active protein after the mature portion is released from the prepro or pro sequence following cleavage of the endopeptidase cleavage domain. This procedure is superior to existing techniques for preparing enzymatically active serine proteases in general, and mast cell serine proteases in particular, because a mast cell serine protease can be prepared at the level of several µg/ml in an enzymatically inactive form that subsequently can be activated when needed. In contrast, the prior art methods for preparing and isolating mast cell serine proteases have been hampered by poor expression efficiency and by the expression of inactive and/or degraded protease.

In the preferred embodiments, the enterokinase susceptibility domain is removed by incubating the host cell expression product with an enterokinase at a pH from about pH 4.0 to about pH 6.0, preferably, about pH 5.2. Preferably, the recombinant protease is purified from the conditioned media before it is activated with enterokinase and used in vitro or in vivo. For recombinant mMCP-7 that lacks the FLAG peptide, the general purification procedure involves dialyzing the insect cell conditioned media 24 to 48 hours using dialysis tubing that has a 5 to kDa cutoff. Since the recombinant pseudo-zymogen is 30 kDa it will not go through the dialysis tubing. This step removes the majority of the low molecular weight peptides and amino acids in the cell conditioned media. The resulting dialyzate is applied to a heparin-Sepharose CL-2B column that has been equilibrated in a low salt pH 5 buffer (Matsumoto et al., J. Biol. Chem. 1995; 270:19524–19531). The recombinant pseudo-zymogen binds to the column at this pH and is eluted from the affinity column by gradually raising the salt concentration or pH of the elution buffer. Finally, the material is applied to a Sephadex gel filtration column. If extremely pure pseudo-zymogen is needed for crystallographic analysis or the like, this material can be subjected to an additional HPLC purification step. For pseudo-zymogens that possess the FLAG peptide at their C-terminus, the conditioned media is passed through an immunoaffinity column that contains anti-FLAG-Ig. This column is commercially available. The pseudo-zymogen is further processed to the desired level of purity using the conditions described above for the FLAG-less material. Following purification, the isolated serine protease is placed in a neutral pH buffer and converted to enzymatically active protease by a brief exposure to enterokinase.

To obtain the recombinant serine protease, the expression cassette is provided in an expression vector. As used herein, a "vector" may be any of a number of nucleic acids into which the expression cassette may be inserted by restriction and ligation for transport between different genetic environments or for expression in the preferred host cells. Vectors typically are composed of DNA and include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The precise nature of the regulatory sequences needed for gene expression may vary between species or cell types, but shall in general include, as necessary, 5' non-transcribing and 5' non-translating sequences involved with the initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See Sambrook et al., *Molecular Cloning: A Laboratory Manual*, Second Edition, Cold Spring Harbor Laboratory Press, 1989. Cells are genetically engineered by the introduction into the cells of heterologous DNA encoding the tryptase-7 protein or fragment or variant thereof. That heterologous DNA is placed under operable control of transcriptional elements to permit the expression of the heterologous DNA in the host cell. In still another aspect of the invention, a defective mast cell or precursor thereof is treated with DNA in a manner to promote via homologous recombination intra cellularly the correction of a defective tryptase-7 gene.

A variety of systems for expression of proteins in bacterial, yeast, mammalian, or insect cells have been described and are commercially available. Preferred systems include the baculovirus expression system such as that described in the Example. Standard protocols exist (c.f. O'Reilly et al., Baculovirus Expression Vectors: A Laboratory Manual, IRL/Oxford University Press, 1992) and vectors, cells, and reagents are commercially available. Preferred systems for mRNA expression in cultured mammalian cells are those such as pRc/CMV (available from Invitrogen, San Diego, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element.

It should be understood that the preceding is merely a detailed description of preferred embodiments. It therefore should be apparent to those of ordinary skill in the art that various modifications and equivalents can be made without departing from the spirit and scope of the invention. All references, patents and patent publications that are identified in this application are incorporated in their entirety herein by reference. The specific Example presented below is illustra-

EXAMPLE

Experimental Procedures

Identification of the Plasma Protein in the V3 Mastocytosis Mouse that Undergoes Rapid Degradation During Passive Systemic Anaphylaxis V3 mastocytosis mice were created and systematically sensitized intraperitoneally with ~200 μg anti-trinitrophenol IgE, as described (Gurish, M. F. et al., Immunity 1995, 3:175–186.; Ghildyal et al., J. Exp. Med. 1996, 184:1061–1073). Approximately 24 h later, ~300 μl of Hank's Balanced Salt Solution alone or containing 10 to 1000 μg of trinitrophenol-bovine serum albumin was injected intraperitoneally into each mouse. Twenty minutes after antigen administration, 100 to 500 μl of blood was obtained from the retroorbital plexus with a Pasteur pipette pretreated with an anticoagulant [either 25 USP units of heparin glycosaminoglycan (Elkins-Sinn, Cherry Hill, N.C.) or 10 mM EDTA]. Samples were centrifuged for 3 to 5 min at ~10,000 g at 4° C. and then subjected to SDS-PAGE. The four prominent ~34-to 55-kDa peptides that preferentially appeared after the sensitization and antigen challenge were transferred to Immobilon-P membranes (Millipore, Bedford, Mass.) and subjected to N-terminal amino acid analysis.

Expression of Pro-EK-mMCP-7 and pro-EK-mMCP-7-FLAG in Insect Cells

Using a polymerase chain reaction (PCR) approach, an oligonucleotide (~5'-GACGACGATGACAAG-3', SEQ ID NO. 38) encoding the EK-susceptible peptide Asp-Asp-Asp-Asp-Lys (amino acids 1–5 of SEQ ID NO. 24) was inserted into the mMCP-7 cDNA (McNeil et al., 1992) between the domain that encodes the pro-peptide and the N-terminus of the mature tryptase. EK is a highly specific enzyme that cleaves the Lys-Ile bond in its Asp-Asp-Asp-Lys-Ile (amino acids 2–6 of SEQ ID NO. 24) recognition motif (Light and Janska, 1989). Because Ile is the essential N-terminal amino acid of mature mMCP-7 and because EK is a relatively stable enzyme at pH 5.0, it was anticipated that the secreted recombinant pseudozymogen could be activated under conditions where the generated mMCP would have very little enzymatic activity until the pH is raised to 7.0. The FLAG peptide (Asp-Tyr-Lys-Asp-Asp-Asp-Lys, SEQ ID NO. 23), which consists of the EK-cleavage sequence C-terminal of a 3-residue linker, has been used by many to epitope tag the N or C terminus of recombinant proteins (Hopp, T. P. et al., Biotechnology 1988 6:1204–1210.). To facilitate the purification of the recombinant pseudozymogen with an anti-FLAG IgG antibody (Prickett, et al., Biotechniques 1989, 7:580–589.; Brizzard, B. L. et al., Biotechniques 1994, 16:730–735), a second construct (pro-EK-mMCP-7-FLAG) was created that also contained the 8-residue FLAG peptide at its C terminus. These two cDNAs were inserted in the correct orientation into the multiple cloning site of pVL1393 (PharMingen, San Diego, Calif.) downstream of the promoter of the polyhedrin gene, as described for the expression of recombinant pro-mMCP-7 (Matsumoto, R. et al., J. Biol. Chem. 1995, 270:19524–19531).

In each instance, purified plasmid DNA (~5 μg) was mixed with 0.5 μg of linearized BaculoGold™ DNA (PharMingen) and calcium phosphate. The resulting DNA solution was added to 3×10⁶ adherent *Spodoptera frugiperda* 9 insect cells (Invitrogen, San Diego, Calif.) that were in their log phase of growth, and infected cells were cultured for 7 days at 27° C. in medium (Invitrogen) supplemented with 10% heat-inactivated (56° C., 30 min) fetal calf serum (Sigma, St. Louis, Mo.). Recombinant virus particles ($\leq 3\times 10^7$) were added to a culture dish containing 6×10⁶ *Trichoplusia ni* High Five™ insect cells (Invitrogen) in their log phase of growth, and the infected cells were cultured in serum-free, Xpress medium (BioWhittaker, Walkersville, Md.). Four days later, the conditioned medium was centrifuged at 1500 g for 15-min at room temperature. Under these conditions, recombinant pro-EK-mMCP-7 and pro-EK-mCP-7-FLAG were recovered in the supernatants as soluble proteins.

Purification of pro-EK-mMCP-7 and pro-EK-mMCP-7-FLAG from Insect Cell-Conditioned Medium, and EK Activation of the Recombinant Pseudozymogens Recombinant pro-EK-mMCP-7 and pro-EK-mMCP-7-FLAG were purified by heparin-Sepharose chromatography, as described (Matsumoto, R. et al., J. Biol. Chem. 1995, 270:19524–19531). Alternatively, recombinant pro-EK-mMCP-7-FLAG was purified with a 2-ml column containing the mouse anti-FLAG M2 monoclonal antibody (International Biotechnol., New Haven, Conn.). This anti-FLAG IgG affinity column was washed with 10 ml of 0.1M glycine, pH 3.5, followed by 50 ml of 50 mM Tris-HCl and 150 mM NaCl, pH 7.4. After ~200 ml of insect cell-conditioned medium was passed through the affinity column, the resin was washed with 50 ml of the same pH 7.4 buffer. Bound pro-EK-mMCP-7-FLAG was eluted by washing the column with 0.1M glycine, pH 3.5. The eluate was collected into tubes that contained 0.1M Tris-HCl, pH 7.0, to minimize acid-mediated denaturation of the recombinant proteins. The final concentration of each recombinant protein was estimated by measuring the absorbance at 280 nm.

Purified pro-EK-mMCP-7 and pro-EK-mMCP-7-FLAG (~100 μg) was separately suspended in ~100 μl of 50 mM sodium acetate and 5 mM calcium chloride, pH 5.2. One μl of a solution containing 422 U of calf intestine EK (1 μg=131 U; Biozyme Lab., San Diego, Calif.) was added to each, and the mixture was incubated at 37° C. for ~3 hr to allow EK to activate the zymogen. In one set of experiments, the EK-activation step was carried out in the presence of 10% glycerol. The spectrophotometric method of Svendsen (Svendsen, L. et al., Throm. Res. 1972, 1:267–278) was used to determine whether or not recombinant mMCP-7 and mMCP-7-FLAG were enzymatically active. A 1-μl sample of each activation mixture was placed in 1 ml of assay buffer [25 mM sodium phosphate, 1 mM EDTA, and 50 μg/ml tosyl-Gly-Pro-Lys-p-nitroanilide (Sigma), pH 7.4]. The change in optical density at 405 nm was determined after a 3 to 5 min incubation at room temperature. The ability of recombinant mMCP-7 to cleave the trypsin-susceptible substrates tosyl-Gly-Pro-Arg-p-nitroanilide, benzoyl-Ile-Glu-Gly-Arg-p-nitroanilide, benzoyl-Phe-Val-Arg-p-nitroanilide, benzoyl-Pro-Phe-Arg-p-nitroanilide, acetyl-Ile-Glu-Ala-Arg-p-nitroanilide, and D-Ile-Phe-Lys-p-nitroanilide (Sigma) was also evaluated.

SDS-PAGE/Immunoblotting and N-terminal Amino Acid Analysis

Insect cell-conditioned medium (~20 μl) containing recombinant pro-mMCP-7, pro-EK-mMCP-7, pro-EK-mMCP-7-FLAG, or purified EK-activated mMCP-7 (~1 μl) was diluted in SDS-PAGE buffer (1% SDS, 5% p-mercaptoethanol, 0.1% bromophenol blue, and 500 mM Tris-HCl, pH 6.8) and boiled for 5 min before being loaded into 12% polyacrylamide gels. After electrophoresis, the gels were stained with Coomassie Blue or were placed in a BIO-RAD (Richmond, Calif.) immunoblotting apparatus, and the resolved proteins were transferred for 2 to 4 hr at 200 mA to Immobilon-P membranes in a solution consisting of 20% methanol and 80% 20 mM Tris-HCl, 150 mM glycine, pH 8.3. For analysis of the resulting protein blots, each membrane was incubated for 1 hr in 5% non-fat milk and then for 1 hr with a 1:500 dilution of affinity-purified rabbit anti-mMCP-7 Ig (Ghildyal et al., 1994) in Tris-buffered saline with 0.01% Tween 20 (TBST buffer). After 3 washes in TBST buffer, the blots were incubated for 1 hr in a 1:1000 dilution of anti-rabbit IgG alkaline phosphatase conjugate (~1 ng/ml final concentration) in TBST buffer. Immunoreactive proteins were visualized with nitroblue tetrazolium (0.2 mg/ml) and 5-bromo-4-chloro-3-indolyl phosphate (0.1 mg/ml) as substrates. For N-terminal amino acid analysis, SDS-PAGE-resolved proteins were electroblotted onto membranes and briefly stained with 0.5% Ponceau S red (Sigma), and the relevant proteins/peptides were subjected to automated Edman degradation by the Harvard Microchemistry Facility (Harvard Biological Laboratories, Cambridge, Mass.).

Generation and Screening of a Phase Display Peptide Library that is Tryptase Specific The N terminus of the protein encoded geneIII (pIII) extends out from the surface of the body of the filamentous phage. By taking advantage of the fact that pIII is protease-resistant and exhibits low valency, a phage display peptide library specific for tryptases was generated that encodes an altered pIII which contains at its N-terminus the FLAG peptide followed by an 8-residue hypervariable peptide. The FLAG peptide was selected as the "tether" ligand so that those phage producing an altered pIII could be readily isolated with the monoclonal anti-FLAG M1 antibody. To create the tryptase-specific library, two complementary single-stranded oligonucleotides [5'-CGGCCGACTACA-AGGACGACGATGACAAGNNNNNNNNNNNA(A/G)GNNNNNNNNNGC-3'(SEQ ID NO. 39), and 5'GGCCGCNNNNNNNNNC(T/C)TNNNNNNNNNNN-NCTTGTCATCGTCGTCCTTGTAGTCGGCCGGCT-3'(SEQ ID NO. 40), where "N" indicates a random nucleotide] were synthesized such that they could be annealed to one another in vitro to form short double-stranded DNAs that each contained SfiI and NotI restriction sites at their 5' and 3' ends, respectively. Because it was found that recombinant mMCP-7 cleaves tosyl-Gly-Pro-Lys-nitroanilide, the library was created such that the fifth residue in the hypervariable domain would be either Arg or Lys. The single-stranded oligonucleotides were mixed in approximately equal concentrations, heated to 94° C. for 1 min, and cooled to room temperature. The resulting double-stranded oligonucleotides were ligated into SfiI/NotI-digested phagemid vector pCANTAB-5E (International Biotechnol.). E. coli (strain TG1), transformed by electroporation with the resulting constructs, were incubated for 1 hr at 37° C. in 2× YT medium [0.09M NaCl containing 1.7% Bacto-tryptone (Difco Lab., Detroit, Mich.), and 1% Bacto-yeast extract (Difco Lab.), pH 7.0] and 2% glucose. Ampicillin (50 μg/ml) and the M13 helper phage K (~10 phage/ bacteria) were added, and the bacteria were incubated at 37° C. for another 1 hr to induce the formation of recombinant phage. After the mixture was centrifuged at 2,000 g for 20 min, the pellet was resuspended in 20 ml of 2× YT medium containing 50 μg/ml ampicillin and 50 μg/ml kanamycin. Infected bacteria were incubated overnight at 37° C. and then were subjected to a 20-min centrifugation at 2,000 g to obtain the phage-enriched supernatant.

The resulting library was screened with bovine pancreatic trypsin to determine its suitability for substrate specificity studies. Because phage clones were obtained after two rounds of trypsin treatment that possessed different peptide sequences in the random portion of the pIII fusion protein, the library was screened with recombinant mMCP-7-FLAG. To purify the recombinant phage, 10 ml of the phage-enriched supernatant was added to 2 ml of 20% polyethylene glycol (8 kDa; Sigma) and 2.5M NaCl and the mixture was incubated at 4° C. for 30 min. After a 30-min centrifugation of the mixture at 10,000 g, the recombinant phage in the pellet were resuspended in 2 ml of 150 mM NaCl, 1 mM $CaCl_2$, and 10 mM sodium phosphate, pH 7.0, and applied to a 1 ml affinity column containing the anti-FLAG M1 monoclonal antibody. The column was washed 3 times with 10 ml of the same pH 7.0 buffer to remove unbound phage. Recombinant mMCP-7-FLAG or bovine pancreatic trypsin (~50 μl of the pH 7.0 buffer) were added, and the column was sealed and incubated at room temperature for 90 min. After treatment with protease, the column was washed with 2 ml of the pH 7.0 buffer to recover those phage that possessed protease-susceptible pIII fusion proteins. Log-phase E. coli were infected with the obtained phage to produce phagemid. Bacteria were again grown in 2× YT medium containing 2% glucose and the phagemid in the bacteria were converted to phage with the addition of helper phage. The selection procedure was repeated one to three additional times to isolate those phage that possessed the most protease susceptible pIII fusion proteins.

E. coli were infected with phage that were susceptible to either trypsin or mMCP-7-FLAG to generate phagemids. The infected bacteria were seeded onto a plate containing 1.5% agar, 2% Bacto-tryptone, 0.5% Bacto-yeast extract, 2% glucose, 90 mM NaCl, 10 mM $MgCl_2$, and 50 μg/ml ampicillin. Individual clones were isolated and grown overnight at 37° C. in 2 ml of 2× YT medium containing 2% glucose with μg/ml ampicillin. Samples (50 μl) of the overnight cultures were centrifuged at 12,000 g for 5 min. The bacteria in the pellets were resuspended in 50 μl water, boiled for 10 min, and again centrifuged. Each PCR was carried out on 2-μl samples of the supernatant with sense (5'-CCCAGCCGGCCGACTACAAGGACG-3', SEQ ID NO. 41) and antisense (5'-TGTTCCTTTCTATGCGGCCCAGC-3', SEQ ID NO. 42) primers. Each of the 35 cycles of the PCR consisted of a 1-min denaturing step at 94° C., a 1-min annealing step at 60° C., and a 1-min extension step at 72° C. The PCR products were subjected to electrophoresis on a 1% agarose gel, and the nucleotide sequences that encode the 8-mer, protease-susceptible peptide domains in the pIII fusion proteins were determined.

Comparative Protein Modeling of the Substrate-Binding Pocket of mMCP-7

A 3D model of the interaction of mMCP-7 with its favored peptide substrate was calculated by the program MODELLER-4, which implements comparative protein modeling by satisfaction of spatial restraints (Šali and Blundell, J. Biol. Chem. 1993, 268:9023–9034; Šali, A. et al., Proteins 1995, 23:318–326). MODELLER is available on Internet at URL http://guitar.rockefeller.edu and also as part of QUANTA and InsightII (MSI, San Diego, Calif., USA; E-mail: blp@msi.com). It was assumed that the interaction between the mMCP-7 and its substrate is similar to the interaction of trypsin with inhibitors of the BPTI class (Perona, J. J. et al., J. Mol. Biol. 1993, 230:919–933). Thus, the crystallographic structures of the complex of bovine trypsin with BPTI (Brookhaven Protein Databank Code 2PTC, SEQ ID NO. 43) and of the complex of a mutant form of a rat trypsin with human amyloid β-protein precursor inhibitor (Brookhaven Protein Databank Code 1BRC, SEQ ID NO. 44) were used as the main template structures for modeling. In addition, these main templates were supplemented in several loop regions in the vicinity of the putative substrate-binding site by loops from kallikrein (Brookhaven Protein Databank Code 2PKA, SEQ ID NO. 45; residues 141 to 152), human neutrophil elastase (Brookhaven Protein Databank Code 1HNE, SEQ ID NO. 46; residues 55 to 68), and rat mast cell protease II (Brookhaven Protein Databank Code 3RP2, SEQ ID NO. 47; residues 30 to 46). These supplementary template loops were selected because they were more similar in length to the corresponding loops in mMCP-7 than the trypsin loops (Topham, C. M. et al., J. Mol. Biol. 1993, 229:194–220).

The alignment between mMCP-7 and the templates was first obtained by the ALIGN2D command of MODELLER and was subsequently edited manually to position gaps in reasonable structural contexts. Next, the standard automated modeling procedure was followed to obtain an ensemble of 3D modles of the mMCP-7/peptide substrate complex. This included an extensive conformational search of the putative substrate-binding loops that do not have equivalent regions in any of the template structures (residues 19 to 28, 46 to 55, and 160 to 178 of mMCP-7, SEQ ID NO. 3) and of the segment with three Pro residues (residues 150 to 154 of mMCP-7, SEQ ID NO. 3). In addition to the restraints derived automatically from the alignment, the a helix starting at position 157 in mMCP-7 was extended to Gly$^{165}$ because this latter residue was predicted from the local sequence pattern to be the C-capping residue of the Schellman motif (Aurora, R., et al., Science 1994, 264:1126–1130). The resulting models were evaluated by PROCHECK (Laskowski, R. L. et al., J. Appl. Cryst. 1993, 26:283–291) which checks the stereochemistry of the model, and by ProsaII which checks the fold of the model. Several cycles of alignment and modeling were done in order to improve the ProsaII profiles of the models. In the end, the model with the lowest value of the MODELLER objective function among the final ensemble of models was picked as the representative model. The full alignment and the 3D model are available from Dr. Andrej Šali (E-mail: sali@rockvax.rockefeller.edu).

Degradation of Mouse Fibrinogen by Recombinant mMCP-7

Samples (5 μg) of purified mouse fibrinogen (Sigma) were each suspended in 1 mM EDTA and 25 mM sodium phosphate, pH 7.4, containing ~0.5 μg recombinant mnMCP-7-FLAG (activated with 0.01 U EK), ~0.5 μg recombinant pro-EK-mMCP-7-FLAG, or 0.01 U EK and incubated for various time periods. The resulting digests were subjected to SDS-PAGE. In three experiments, the N-terminal amino acid sequences of the major fibrinogen fragments in the digests were determined.

A standard fibrinogenolysis assay (Brown, B., Coagulation, In Hematology: Principles and Procedures, 5th ed., Lea and Febiger, Philadelphia, 1988, pp. 210–222.) was used to detect mMCP-7 anti-coagulant activity in vitro. Sodium citrate-treated, normal mouse plasma (100 μl/assay) was incubated for 1 hr at 37° C. in the absence or presence of either ~4 μg of EK-activated mMCP-7-FLAG or 10 USP units of heparin (~100 μg of the glycosaminoglycan). The time required for thrombin to clot the sample was then determined with a fibrometer. The plasma concentration of fibrinogen is ~3 mg/ml. Thus, even if 100% of the recombinant pseudozymogen was converted to active enzyme by EK treatment, there is ~75-fold more fibrinogen than mMCP-7 in the assay on a weight basis.

Results

Identification of the Major Plasma Protein in the V3 Mastocytosis Mouse that Undergoes Rapid Degradation During Passive Systemic Anaphylaxis Relative to V3 mastocytosis mice sensitized with IgE but not challenged with antigen, the plasma from IgE/antigen-treated V3 mastocytosis mice contained large amounts of ~34-, 40-, and 55-kDa peptides, and lesser amounts of a ~42-kDa peptide. The ~34-, 40-, and 42-kDa peptides possessed the same N-terminal amino acid sequence of Thr-Asp-Thr-Glu-Asp-Lys-Gly-Glu-Phe-Leu-Ser-Glu-Gly-Gly-Gly-Val-Arg-Gly-Pro-Arg-Val-Val-Gu-Arg (SEQ ID NO. 48). In contrast, the ~55-kDa peptide possessed an N-terminal amino acid sequence of Try-Val-Ala-Thr-Arg-Asp-Asn-Cys-Cys-Ile-Leu-Asp-Glu (SEQ ID NO. 49).

Generation of pro-enterokinase (EK)-mMCP-7 and pro-EK-mMCP-7-FLAG in Insect Cells, and EK Conversion of the Recombinant Pseudozymogens to Active Tryptases Insect cells infected with the relevant baculovirus construct secreted substantial amounts of pro-EK-mMCP-7 and pro-EK-mMCP-7-FLAG into the conditioned medium. These recombinant proteins could be purified from contaminating insect proteins by affinity column chromatography with anti-FLAG Ig or heparin-Sepharose. Both recombinant proteins bound to a heparin-Sepharose column that had been equilibrated in 100 mM NaCl/10 mM sodium phosphate, pH 5.5. Because they dissociated from the column when the NaCl concentration of the buffer was raised to ~300 mM, analogous to properly folded recombinant pro-mMCP-7, insect cell-derived pro-EK-mMCP-7 and pro-EK-mMCP-7-FLAG appear to be properly folded. As assessed by SDS-polyacrylamide gel electrophoresis (PAGE), both recombinant pseudo-zymogens decreased in size by -2 kDa after treatment with EK. Amino acid sequence analysis revealed that, after treatment with EK, both recombinant proteins possessed an N-terminal sequence of Ile-Val-Gly-Gly-Gln-X-Ala-X-Gly-Asn-Lys (SEQ ID NO. 50), which is identical to that of mature mMCP-7 deduced from its cDNA.

Recombinant mMCP-7 and mMCP-7-FLAG readily cleaved tosyl-Gly-Pro-Lys-p-nitroanilide and tosyl-Gly-Pro-Arg-p-nitroanilide. However, unlike pancreatic trypsin, neither effectively cleaved benzoyl-Ile-Glu-Gly-Arg-p-nitroanilide, benzoyl-Phe-Val-Arg-p-nitroanilide, benzoyl-Pro-Phe-Arg-p-nitroanilide, acetyl-Ile-Glu-Ala-Arg-p-nitroanilide, or D-Ile-Phe-Lys-p-nitroanilide. The amount of tryptase activity was not increased substantially if heparin glycosaminoglycan was present during the EK activation step or during the incubation with the peptide substrates. Recombinant mMCP-7 and mMCP-7-FLAG possessed optimal enzymatic activity at ~pH 7.4. Although they retained much of their enzymatic activities even after a 5 hr incubation at 37° C. in the standard activation buffer, their activities were ~3 fold greater if glycerol was present during the EK treatment step. Moreover, glycerol inhibited the time-dependent inactivation of the recombinant proteases.

Recombinant mMCP-7-FLAG was used in subsequent studies because it could be purified more easily with the anti-FLAG Ig column, it could be activated without heparin glycosamino-glycan, and its physical and biological properties were similar to those of mMCP-7. When the peptide display library was subjected to 4 rounds of treatment with mMCP-7-FLAG, the only clone obtained had a peptide domain within the pIII fusion protein that consisted of Ser-Leu-Ser-Ser-Arg-Gln-Ser-Pro (SEQ ID NO. 54, See Table 1). When the library was subjected to only 2 rounds of treatment with mMCP-7-FLAG and 28 of the clones were arbitrarily sequenced, the peptide domains of 8 of the isolated clones possessed the same conserved sequence as that obtained after 4 rounds of treatment with mMCP-7-FLAG. Of the 20 remaining clones, 15 had at least one Ser or Thr residue. Ser and Thr were the favored residues at the P2 site. Moreover, 19 of the 28 clones had a Ser or Thr residue in either the putative P1' or P2' site. Although the preferred mMCP-7-susceptible peptide was found when the library was treated twice with bovine pancreatic trypsin, the other mMCP-7 susceptible peptides were not obtained.

consists of 9 residues. A three dimensional (3D) model of the complex between mMCP-7 and its preferred peptide substrate, Ser-Leu-Ser-Ser-Arg-Gln-Ser-Pro (SEQ ID NO. 54) is similar to the crystallographic structure of the trypsin/bovine pancreatic trypsin inhibitor (BPTI, SEQ ID NO. 43) complex. The backbone root-mean-square difference between trypsin and the mMCP-7 model is 0.2 Å. Although the model passes all stereochemical tests implemented in PROCHECK, evaluation of the model by ProsaII indicates

TABLE 1 mMCP-7-Susceptible Peptides in pIII Fusion Proteins[a]

| No. of Clones | Amino Acid Sequence of Peptide | |
|---|---|---|
| | A. Two Rounds of Treatment | |
| 8 | Ser—Leu—Ser—Ser—Arg—Gln—Ser—Pro | (SEQ ID NO. 54) |
| 1 | Cys—Thr—Ser—Ser—Arg—Pro—Ser—Gly | (SEQ ID NO. 55) |
| 1 | Ser—Gly—Phe—Gly—Arg—Leu—Ser—Asp | (SEQ ID NO. 56) |
| 1 | Arg—Ser—Gln—Thr—Arg—Lys—Ser—Lys | (SEQ ID NO. 57) |
| 1 | Lys—Lys—Gln—Gly—Arg—Asp—Ser—Thr | (SEQ ID NO. 58) |
| 1 | Arg—Lys—Gln—Lys—Arg—Arg—Thr—Glu | (SEQ ID NO. 59) |
| 1 | Pro—Pro—Ser—Phe—Arg—Arg—Ser—Ser | (SEQ ID NO. 60) |
| 1 | Leu—Pro—Tyr—Gly—Arg—Ala—Thr—Thr | (SEQ ID NO. 61) |
| 1 | Asn—Thr—Pro—Thr—Lys—Leu—Ser—Pro | (SEQ ID NO. 62) |
| 1 | Arg—Arg—Pro—Thr—Lys—Lys—Asn—Thr[b] | (SEQ ID NO. 63) |
| 1 | Arg—Gly—Glu—Lys—Arg—Ser—Lys—Ser | (SEQ ID NO. 64) |
| 1 | Met—Leu—Leu—Ile—Arg—Thr—Trp—Glu | (SEQ ID NO. 65) |
| 1 | Val—Thr—Tyr—Ala—Arg—Leu—Cys—Try | (SEQ ID NO. 66) |
| 1 | Leu—Ser—Tyr—Arg—Lys—Leu—Arg—Phe | (SEQ ID NO. 67) |
| 1 | Gly—Thr—Arg—Arg—Arg—Glu—Glu—His | (SEQ ID NO. 68) |
| 1 | Asp—Arg—Lys—Gly—Arg—Gln—Gln—Gln | (SEQ ID NO. 69) |
| 1 | Arg—Tyr—Pro—Cys—Arg—Tyr—Gly—Leu | (SEQ ID NO. 70) |
| 1 | Lys—Glu—Glu—Asn—Arg—Lys—Asn—Asn | (SEQ ID NO. 71) |
| 1 | Phe—His—Pro—Ser—Arg—His—Pro—Pro | (SEQ ID NO. 72) |
| 1 | Ile—Ala—Arg—Glu—Lys—Gly—Gln—Gln | (SEQ ID NO. 73) |
| 1 | Ile—Cys—Pro—Pro—Arg—Leu—Leu—Gln | (SEQ ID NO. 74) |
| | B. Four Rounds of Treatment | |
| 12 | Ser—Leu—Ser—Ser—Arg—Gln—Ser—Pro | (SEQ ID NO. 54) |

[a]The phage display peptide library was incubated 2(A) or 4(B) times with recombinant mMCP-7-FLAG, clones were isolated, and the deduced amino acid sequences of the protease-susceptible domains in the pIII fusion protein were deduced.
[b]In peptides such as this one with more than one Arg or Lys residue, it is not clear which is the P1 residue in the peptide.

Comparative Protein Modeling of the Substrate-Binding Pocket of mMCP-7

The amino acid alignment of mMCP-7 and bovine pancreatic trypsin shows that the sequence identity of the two serine proteases is 39%. There are 9 gaps in the optimal alignment, 5 of which are insertions in mMCP-7. The longest insertion, occurring at position 162 in mMCP-7, that 3 regions are probably modeled with backbone errors >2 Å. Of these three regions, only the 9-residue insertion is potentially in contact with the peptide substrate. Generally, the errors in a homology-derived model of a target sequence are similar to the structural differences between proteins that have the same sequence similarity as the template structure and the target sequence. Thus, most of the main chain atoms in the mMCP-7 model have a root-mean-square error of ~1.5 Å, corresponding to the 39% sequence identity of trypsin and mMCP-7.

Degradation of Mouse Fibrinogen by mMCP-7

After an exhaustive 3-hr digestion of mouse fibrinogen with mMCP-7-FLAG, five prominent peptides of ~57, 42, 40, 38, and 34 kDa were obtained. The ~34-, 40-, and 42-kDa peptides possessed the same N-terminal amino acid sequence of Thr-Asp-Thr-Glu-Asp-Lys-Gly-Glu-Phe-Leu (SEQ ID NO. 51). In contrast, the N-terminal amino acid sequence of the 38-kDa peptide was Tyr-Val-Ala-Thr-Arg-Asp-Asn-X-X-Ile-Leu-Asp-Glu (SEQ ID NO. 52) and that of the ~57-kDa peptide was Arg-Lys-Glu-Glu-Pro-[Pro]-Ser-Leu-Arg-Pro-Ala-Pro-Pro (SEQ ID NO. 53). Based on N-terminal amino acid analysis of the three chains of native mouse fibrinogen, the ~34-, 38-, 40-, 42- and 57-kDa peptides in the digest are derived from the α, γ, α, α, and β chains of mouse fibrinogen, respectively. Kinetic studies revealed that mouse fibrinogen is rapidly cleaved by mMCP-7 and that the α chain is most susceptible to the tryptase.

Despite the high concentration and diversity of protease inhibitors in mouse plasma, the fibrinogenolysis assay carried out on whole plasma confirmed the in vivo and in vitro data that mMCP-7 is a potent anticoagulant. In control experiments, thrombin induced normal mouse plasma to clot with ~15 sec. However, thrombin was not able to induce the formation of a fibrin clot within 40 sec in those plasma samples that had been pretreated for 1 hr at 37° C. with the recombinant tryptase. The anticoagulant activity of mMCP-7 in this assay was equal to or better than 10 units of heparin glycosaminoglycan.

Discussion

Mouse mast cells express various combinations of at least nine serine proteases, two of which are tryptases. Although tryptases are major granule constituents of those mast cells that reside in the skin, skeletal muscle, and spleen (Stevens, R. L. et al., Proc. Natl. Acad. Sci. USA 1994, 91:128–132; Gurish, M. F. et al., Immunity 1995, 3:175–186.; Ghildyal et al., J. Exp. Med. 1996, 184:1061–1073), their functions have not been determined. In the present study, we demonstrate that the plasma protein fibrinogen is preferentially degraded by mMCP-7. Thus, mMCP-7 functions as an anticoagulant.

Because the plasma of the V3-mastocytosis mouse contains substantial amounts of enzymatically active mMCP-7 shortly after the IgE-sensitized animal is given antigen (Ghildyal et al., J. Exp. Med. 1996, 184:1061–1073), this mouse model system was examined to determine which plasma proteins, if any, are candidate substrates for mMCP-7 in vivo. Relative to mice that are sensitized with IgE but not challenged with antigen, the plasma from IgE/antigen-treated V3 mastocytosis mice contained large amounts of four peptides ranging from ~55 kDa to ~34 kDa. The ~34-, 40- and 42-kDa peptides all possessed the same N-terminal amino acid sequence. Although the complete amino acid sequences of the three chains of mouse fibrinogen have not been deduced, the last 13 residues of these three peptides are 100% identical to residues 11 to 23 of the α chain of human fibrinogen (Rixon, M. W. et al., Biochemistry 1983, 22:3237–3244). N-terminal amino acid analysis of purified mouse fibrinogen confirmed the conclusion that they were derived from the α chain of fibrinogen. The ~55-kDa peptide in the plasma of the IgE/antigen-treated V3 mastocytosis mice possessed an N terminus that corresponds precisely with the N terminus of the γ chain of human fibrinogen (Crabtree, G. R. et al., J. Mol. Biol. 1985, 185:1–19), indicating that it, too, is derived from fibrinogen.

Fibrinogen regulates endothelial cell adhesion and platelet aggregation via the $α_v β_3$ and $α_{IIb} β_3$ integrins, respectively. In the case of human fibrinogen, the varied integrin-binding motifs reside in the last half of the α and γ chains Marguerie, G. A. et al., Eur. J. Biochem. 1984, 139:5–11; Lam, S. C-T. et al., J. Biol. Chem. 1987, 262:947–950; Cheresh, D. A. et al., Cell 1989, 58:945–953; Farrell, D. H. et al., Proc. Natl. Acad. Sci. USA 1992, 89:10729–10732; Hawiger, J. et al., Sem. Hematol.1995, 32:99–109; Thiagarajan, P. et al., Biochemistry 1996, 3: 4169–4175). The failure to detect the C-terminal peptides of the degraded α and γ chains of fibrinogen in the plasma of IgE/anigen-treated V3 mastocytosis mice suggests that they are rapidly cleared from the circulation via $α_v β_3$ and/or $α_{IIb} β_3$ integrin-mediated pathways.

Although the data from the V3 mastocytosis mice suggested that fibrinogen is the physiologic substrate of mMCP-7, the possibility could not be ruled out that this plasma protein is degraded by one or more of the chymases exocytosed from activated mast cells. Moreover, even if the degradation of fibrinogen in the V3 mastocytosis mouse is regulated by mMCP-7, it was not possible to deduce whether the tryptase effect is direct or indirect. Although the substrate preference of a mMCP can be determined with recombinant protease, we and others have been unable to express large amounts of an enzymatically active protease like mMCP-7 in insect cells. To overcome these difficulties, we used a novel bioengineering approach to induce insect cells to express and secrete large amounts of pseudozymogen forms of mMCP-7 that could be rapidly activated after their purification from conditioned medium. Insect cells infected with the relevant baculovirus construct secreted large amounts of properly folded pro-EK-mMCP-7 and pro-EK-mMCP-7-FLAG into the conditioned medium. As assessed by SDS-PAGE and N-terminal amino acid sequence analysis of the resulting products, EK selectively removed the propeptides, thereby converting the two forms of the recombinant tryptase to active enzyme.

Heparin-containing serglycin proteoglycans are required for human mast cell tryptases to exert enzymatic activity (Schwartz, L. B. et al., J. Biol. Chem. 1986, 261:7372–7379).

Since recombinant mMCP-7 readily cleaved tosyl-Gly-Pro-Lys-p-nitroanilide in the absence of heparin glycosaminoglycan, the enzymatic activity of this mouse tryptase apparently is not controlled by heparin-containing serglycin proteoglycans outside of the mast cell. It was therefore anticipated that a peptide display library containing either a Lys or Arg at the P1 site would reveal the preferred substrate sequence cleaved by mMCP-7. The peptide display library created in this study was screened with recombinant mMCP-7-FLAG rather than recombinant mMCP-7 because the former could be purified without the heparin-Sepharose chromatography step. When the library was subjected to four rounds of treatment with mMCP-7-FLAG, the only clone obtained had a peptide domain in the pIII fusion protein that consisted of Ser-Leu-Ser-Ser-Arg-Gln-Ser-Pro (SEQ ID NO. 54). Even when the number of codons that encode Ser is taken into account, the representation of this amino acid in the mMCP-7 susceptible peptide is considerably higher than by chance. Since mMCP-7 is a tryptase, the Arg residue in the obtained octamer is the P1 residue. When the library was subjected to only 2 rounds of treatment with mMCP-7-FLAG, many of the clones possessed the conserved sequence. In addition, almost all clones had at least one Ser or Thr residue at the putative P2, P1', and/or P2' sites. Val and Ile were underrepresented in the mMCP-7 susceptible peptides.

A computer search of a protein data base with the sequence of Leu-Ser-Ser-Arg-Gln-Ser (amino acids 2–7 of SEQ ID NO. 54) revealed that residues 309 to 314 in the middle of the α chain of rat fibrinogen has the nearly identical sequence of Gly-Ser-Ser-Arg-Pro-Ser (SEQ ID NO. 76). The presence of a homologous sequence in the α chain of mouse fibrinogen would explain why fibrinogen is so susceptible to degradation by recombinant mMCP-7. After an exhaustive in vitro incubation of mouse fibrinogen with mMCP-7-FLAG, five prominent peptides ranging from ~34kDa to 57 kDa were obtained. N-terminal amino acid analysis revealed that three of the peptides were derived from the α chain; the other two were derived from the β and γ chains. The discovery that three of the major peptides found in the plasma of the V3 mastocytosis mouse were the same as those generated in the in vitro study indicates that fibrinogen is the physiologic substrate of mMCP-7 in the V3 mastocytosis mouse. The subsequent kinetic study revealed that the α chain of fibrinogen is the chain most susceptible to degradation by mMCP-7. The data from the peptide display library are consistent with an mMCP-7-mediated attack at Arg/Lys resides that have Ser at the P2, P1', and/or P2' sites.

The most useful analysis of substrate specificity relies on the high-resolution X-ray crystallographic structures of the enzyme-inhibitor complexes and their mutants (Perona, J. J. et al., Protein Sci. 1995, 4:337–360). In general, the substrate-binding clefts of serine proteases are long enough to interact with 7 residues from P4 to P3'. However, contrary to the P1 preference, it is difficult to predict the specificity of the other substrate-binding sites in serine proteases because the specificities at these other positions appear to be determined by the flexibility and shape of the binding cleft, as well as by the changes in the amino acid sequence that are spatially distant from the cleft (Perona, J. J. et al., Protein Sci. 1995, 4:337–360). Nevertheless, a 3D model of the mMCP-7/substrate interaction can still be used to explain some experimental results and make testable predictions. The alignment of mMCP-7 with trypsin and the 3D model of the mMCP-7/substrate complex are both consistent with the observed tryptic activity of recombinant mMCP-7, which is defined as its strong preference for a Lys or Arg residue at position P1. All 14 residues in trypsin that are in contact with the P1 Lys of BPTI are absolutely conserved in mMCP-7. Moreover, the 3D model shows that the P1 Arg residue of the mMCP-7-susceptible peptide substrate can fit well into its S1 subsite. The conservation of the S1 subsite is in contrast to the large differences between the other subsites in mMCP-7 and trypsin. Only 6 of the 42 residues in the substrate-binding loops that do not contribute to the S1 site of mMCP-7 are conserved.

In addition to residue type differences relative to trypsin, the mMCP-7 model indicates residue insertions in three loops that are likely to form part of the substrate-binding cleft of this tryptase. The insertions in mMCP-7 consist of 4 residues in loop 1, 2 residues in loop B, and 9 residues in loop 3. Loops 1, B, and 3 contribute to pockets S1' to S3', S2 to S1', and S3, respectively. The insertions in the model protrude out of the surface and make the substrate-binding cleft of mMCP-7 deeper than in trypsin. Thus, the model suggests that the substrate specificity of mMCP-7 at positions P3 to P3' may be more restricted than that of trypsin. This is supported by the fact that recombinant mMCP-7 and mMCP-7-FLAG cleave tosyl-Gly-Pro-Lys-p-nitroanilide but not similar nitroanilide substrates which are susceptible to cleavage by trypsin. A possible exception is loop D. In trypsin, $Tyr^{151}$ in this loop contributes to the S2' subsite. This residue is replaced by Pro in mMCP-7, whose much shorter side chain is predicted not to interact with the substrate. Although trypsin possesses a relatively shallow ligand-binding cleft, the enzyme is still able to make contacts with distant residues in BPTI (i.e., residues other than P3 to P2'). Inasmuch as the model predicts that the substrate-binding cleft is deeper in mMCP-7 than in trypsin, these non-local contacts may be even more extensive during the interaction of mMCP-7 and its protein substrate. For example, the 9-residue insertion at position 172 of mMCP-7 may be contacting some remote region in fibrinogen, conferring additional substrate specificity to the tryptase.

The observations that mast cell tryptases can induce airway smooth muscle hyper-responsiveness in dogs (Sekizawa, K. et al., J. Clin. Invest. 1989, 83:175–179), reverse airway smooth muscle relaxation induced by vasoactive intestinal peptide in ferrets (Franconi, G. M. et al., J. Pharmacol. Exp. Ther. 1989, 248:947–951), and induce proliferation of fibroblasts (Ruoss, S. J. et al., J. Clin. Invest. 1991, 88:493–499) and epithelial cells (Cairnes, J. A. et al., Immunol. 1996, 156:275–283.) suggest that mast cell tryptases regulate growth factor and/or adhesion receptors on the surfaces of cells. Nevertheless, the possibility exists that one of the mouse mast cell tryptases evolved primarily to degrade proteins residing in the extracellular matrix or plasma. In a preliminary screening of our peptide display library with recombinant mMCP-6, we discovered that this tryptase has a preferred amino acid sequence distinct from that of mMCP-7. Thus, some of the confusion about the preferred substrate specificity of each tryptase is likely a consequence of the presence of multiple proteases in the previously analyzed preparations.

Fibrinogen, a plasma protein essential for blood coagulation (Doolittle, R. F., Ann. Rev. Biochem. 1984, 53:195–229), is a large sized glycoprotein consisting of two sets of three distinct polypeptide chains that are all disulfide bonded. When the $Arg^{16}$-$Gly^{17}$ bond in the α chain of a fibrinogen molecule is cleaved by thrombin, a N-terminal polymerization site is exposed, which in turn interacts with a complementary site of the γ chain of the distal portion of another fibrinogen molecule to initiate the formation of the fibrous clot. Fibrinogen also plays a critical role in the aggregation of platelets during clot formation. Why mMCP-7 evolved to preferentially degrade fibrinogen is a matter of conjecture. Mast cells, as effector cells of the immune response that reside in tissues, are one of the first participants in inflammatory responses. When activated through their high -affinity IgE receptors, mast cells immediately release their preformed granule mediators and quickly generate and release different arachidonic acid metabolites. Within 30 min after IgE/antigen treatment of the cells, activated mast cells dramatically up-regulate their production of cytokines and chemokines. This complex immune response eventually results in vasodilation and an influx of hematopoietic cells into the inflammatory site. Surprisingly, one does not find large amounts of cross-linked fibrin in tissues after mast cell-mediated inflammatory responses. Aggregated platelets are also rarely seen. By quantitating the uptake of [$^{125}$I] fibrinogen into the skin of the mouse, Mekori and Galli found that some plasma fibrinogen makes its way into the cutaneous site 2 hr after the initiation of an IgE-dependent immediate hypersensitivity reaction. However, 24 hr after the initiation of the mast cell response, very little urea-insoluble [$^{125}$I]fibrin could be detected in the inflammatory site relative to that obtained in a T-cell dependent contact sensitivity reaction at a differnet cutaneous site in the same animal. Unlike the other mMCPs, mMCP-7 quickly dissociates from the protease/ proteoglycan macromolecular complex after exocytosis. Because it diffuses away from the inflammatory site, mMCP-7 can inactivate fibrinogen before it can induce platelet aggregation and before it can be induced by thrombin to accumulate as cross-linked fibrin. Thus, mMCP-7 probably plays a critical role in hemostasis by ensuring that circulating lymphocytes and granulocytes can access inflammatory sites easily.

TABLE 2

Table 2 presented below includes references to the GenBank Accession numbers of selected sequences presented in the Sequence Listing, followed by the claims and the abstract.

| | |
|---|---|
| SEQ ID NO: 1 | is the nucleotide sequence of the mMCP-7 zymogen (GenBank No. L00653). |
| SEQ ID NO: 2 | is the nucleotide sequence of the mMCP-7 zymogen (GenBank No. L00654). |
| SEQ ID NO: 3 | is the deduced amino acid sequence of the mMCP-7 zymogen (GenBank No. L00654 or L00654). |
| SEQ ID NO: 4 | is the nucleotide sequence of a rat homolog of mMCP-7 zymogen (GenBank No. D38455, Ide et al., J. Biochem. 1995, 118:210–215). |
| SEQ ID NO: 5 | is the deduced amino acid sequence of a rat homolog of mMCP-7 zymogen (GenBank No. D38455, Ide et al., J. Biochem, 1995, 118:210–215) |
| SEQ ID NO: 6 | is the amino acid sequence of a rat homolog of mMCP-7 zymogen (Braganza and Simmons, Biochemistry 1991, 30:4997–5007). |
| SEQ ID NO: 7 | is the nucleotide sequence of a gerbil homolog of mMCP-7 zymogen (GenBank No. D31789, Murakumo et al., Biochem. J. 1995, 309:921–926). |
| SEQ ID NO: 8 | is the deduced amino acid sequence of a gerbil homolog of mMCP-7 zymogen (GenBank No. D31789, Murakumo et al., Biochem. J. 1995, 309:921–926). |
| SEQ ID NO: 9 | is the nucleotide sequence of a dog homolog of mMCP-7 zymogen (GenBank No. J02862, Vanderslice, et al., Biochemistry 1989, 28:4148–4155). |

TABLE 2-continued

Table 2 presented below includes references to the GenBank Accession numbers of selected sequences presented in the Sequence Listing, followed by the claims and the abstract.

| | |
|---|---|
| SEQ ID NO: 10 | is the deduced amino acid sequence of a dog homolog of mMCP-7 zymogen (GenBank No. J02862, Vanderslice, et al., Biochemistry 1989, 28:4148–4155). |
| SEQ ID NO: 11 | is the nucleic acid sequence of human mast cell tryptase α (GenBank No. M30038). |
| SEQ ID NO: 12 | is the deduced amino acid sequence of human mast cell tryptase α (GenBank No. M30038). |
| SEQ ID NO: 13 | is the nucleic acid sequence of human mast cell tryptase I (GenBank No. M33491). |
| SEQ ID NO: 14 | is the deduced amino acid sequence of human mast cell tryptase I (GenBank No. M33491). |
| SEQ ID NO: 15 | is the nucleic acid sequence of human mast cell tryptase II/β (GenBank No. M33492). |
| SEQ ID NO: 16 | is the deduced amino acid sequence of human mast cell tryptase II/β (GenBank No. M33492). |
| SEQ ID NO: 17 | is the nucleic acid sequence of human mast cell tryptase III (GenBank No. M33493). |
| SEQ ID NO: 18 | is the deduced amino acid sequence of human mast cell tryptase III (GenBank No. M33493). |
| SEQ ID NO: 19 | is the nucleotide sequence of mMCP-6 (GenBank No. M57625, Reynolds, et al., J. Biol. Chem. 1991, 266:3847–3853). |
| SEQ ID NO: 20 | is the nucleotide sequence of mMCP-6 (GenBank No. M57626, Reynolds, et al., J. Biol. Chem. 1991, 266:3847–3853). |
| SEQ ID NO: 21 | is the deduced amino acid sequence of the mMCP-6 zymogen (GenBank Nos. M57625 and M57626, Reynolds, et al., J. Biol. Chem. 1991, 266:3847–3853). |

I claim:

1. A nucleic acid encoding, from its 5' to 3' direction:
   a) a pro sequence of a serine protease zymogen;
   b) an enterokinase susceptibility domain; and
   c) a coding sequence for a mature serine protease, wherein the mature serine protease is derived from the serine protease zymogen.

2. The nucleic acid of claim 1, wherein the mature serine protease has an amino terminus that is leucine or isoleucine.

3. The nucleic acid of claim 1, further comprising a signal sequence of the serine protease zymogen positioned 5' to the pro sequence.

4. The nucleic acid of claim 2, wherein the mature serine protease is a mast cell protease.

5. The nucleic acid of claim 4, wherein the mast cell protease is a chymase.

6. The nucleic acid of claim 4, wherein the mast cell protease is a tryptase-7.

7. The nucleic acid of claim 6, wherein the mast cell protease is selected from the group consisting of an mMCP-7 and a humanized tryptase-7.

8. A method of producing a serine protease comprising the steps of:

1) culturing a host cell which expresses the nucleic acid of claim 1 in a medium under conditions that promote expression and secretion of the serine protease as an inactive zymogen;

2) purifying the inactive zymogen;

3) cleaving the enterokinase susceptibility domain; and 4) collecting the mature serine protease.

9. The method of claim 8, further comprising the step of activating the mature serine protease.

10. The method of claim 8, wherein the host cell comprises an insect cell.

11. The method of claim 8, wherein collecting the serine protease comprises contacting the serine protease with an immobilized antibody that selectively binds to the mature serine protease.

* * * * *